(12) United States Patent
Spirtos

(10) Patent No.: US 12,303,488 B2
(45) Date of Patent: *May 20, 2025

(54) CANNABIS BASED THERAPEUTIC AND METHOD OF USE

(71) Applicant: YUZU LV LLC, Las Vegas, NV (US)

(72) Inventor: Nicola Michael Spirtos, Las Vegas, NV (US)

(73) Assignee: YUZU LV LLC, Las Vegas, NV (US)

( * ) Notice: Subject to any disclaimer, the term of this patent is extended or adjusted under 35 U.S.C. 154(b) by 102 days.

This patent is subject to a terminal disclaimer.

(21) Appl. No.: 18/131,052

(22) Filed: Apr. 5, 2023

(65) Prior Publication Data

US 2023/0293480 A1    Sep. 21, 2023

Related U.S. Application Data

(63) Continuation of application No. 16/971,781, filed as application No. PCT/US2019/019465 on Feb. 25, 2019, now Pat. No. 11,684,604.

(60) Provisional application No. 62/634,547, filed on Feb. 23, 2018.

(51) Int. Cl.
| | |
|---|---|
| *A61K 31/352* | (2006.01) |
| *A61K 31/01* | (2006.01) |
| *A61K 31/015* | (2006.01) |
| *A61K 31/05* | (2006.01) |
| *A61K 47/10* | (2017.01) |
| *A61K 47/12* | (2006.01) |
| *A61K 47/44* | (2017.01) |
| *A61K 47/46* | (2006.01) |
| *A61P 25/36* | (2006.01) |

(52) U.S. Cl.
CPC ............ *A61K 31/352* (2013.01); *A61K 31/01* (2013.01); *A61K 31/015* (2013.01); *A61K 31/05* (2013.01); *A61K 47/10* (2013.01); *A61K 47/12* (2013.01); *A61K 47/44* (2013.01); *A61K 47/46* (2013.01); *A61P 25/36* (2018.01)

(58) Field of Classification Search
CPC .................................................. A61K 31/352
See application file for complete search history.

(56) References Cited

U.S. PATENT DOCUMENTS

| | | | |
|---|---|---|---|
| 9,375,417 | B2 | 6/2016 | Smith et al. |
| 11,684,604 | B2 * | 6/2023 | Spirtos .................. A61K 45/06 514/454 |
| 2016/0106705 | A1 | 4/2016 | Verzura |
| 2017/0273914 | A1 | 9/2017 | Knudsen |
| 2018/0169035 | A1 | 6/2018 | Eyal |
| 2018/0369191 | A1 | 12/2018 | Muscarella |
| 2020/0037638 | A1 | 2/2020 | Faraci |
| 2020/0138737 | A1 | 5/2020 | Hetherington |

FOREIGN PATENT DOCUMENTS

| | | | | |
|---|---|---|---|---|
| CN | 110575432 | B | 10/2021 | |
| WO | 201715839 | A1 | 2/2017 | |
| WO | 201791764 | A1 | 6/2017 | |
| WO | WO 2017091764 | * | 6/2017 | .......... A61K 31/352 |
| WO | WO 2017158539 | * | 9/2017 | .......... A61K 31/352 |
| WO | WO-2017158539 | A1 * | 9/2017 | ............ A61K 31/01 |
| WO | 2019034936 | A2 | 2/2019 | |
| WO | 2019165387 | A1 | 8/2019 | |
| WO | 2020006322 | A1 | 1/2020 | |
| WO | 2020009950 | A1 | 1/2020 | |
| WO | 2020021545 | A1 | 1/2020 | |
| WO | 2020214200 | A1 | 10/2020 | |

OTHER PUBLICATIONS

Russo, Frontiers in Pharmacology, Sep. 2016 | vol. 7 | Article 309, 1-19.*
Feldman, Understanding 'Evergreening': Making Minor Modifications Of Existing Medications To Extend Protections, Health Affairs Jun. 2022 41:6, 801-804.*
Dwivedi, Evergreening: A deceptive device in patent rights, Technology in Society 32 (2010) 324-330.*
Greg Miller, Could pot help solve the U.S. opioid epidemic? Science.org/content/article/could-pot-help-solve-us-opioid-epidemic, Nov. 2016, 1-9.*
Hurd, Early Phase in the Development of Cannabidiol as a Treatment for Addiction: Opioid Relapse Takes Initial Center Stage Neurotherapeutics (2015) 12:807-815.*
Reiman, Cannabis as a Substitute for Opioid-Based Pain Medication: Patient Self-Report, Cannabis and Cannabinoid Research 2017, 2.1, 160-166.*
Handbook of Pharmaceutical Excipients, American Pharmaceutical Association, 1986.
International Search Report and Written Opinion for PCT/US2021/040115, mailed Dec. 17, 2021.
Li et al: Naringenin inhibits dendritic cell maturation and has therapeutic effects in a murine model of collagen-induced arthritis, Journal of Nutritional Biochemistry, 2015, vol. 26, No. 12, p. 1467-1478.
Ruiz-Miyazawa et al.: The citrus flavanone naringenin reduces gout-induced joint pain and inflammation in mice by inhibiting the activation of NF[kappa]B and macrophage release of IL-I[beta], Journal of Functional Foods, 2018, vol. 48, pp. 106-116.
Zhao et al., Naringin Protects Against Cartilage Destruction in Osteoarthritis Through Repression of NF-[kappa]B Signaling Pathway, Inflammation, 2015, vol. 39, No. 1, p. 385-392.
Abrams Di, Couey P, Shader SB, Kelly ME, Benowitz NI. Cannabinoid-opioid Interaction in chronic pain. Clin. Pharmacol. Ther. 2011; vol. 90; pp. 844-851.
Adams Ib, Martin BR. Cannabis: pharmacology and toxicology in animals and humans. Addiction. 1996; vol. 91; pp. 1585-1614.

(Continued)

*Primary Examiner* — Nizal S Chandrakumar
(74) *Attorney, Agent, or Firm* — Greenberg Traurig, LLP

(57) ABSTRACT

The present disclosure relates to cannabinoid-based therapeutics, and their use in treating pain, e.g., chronic pain. The present disclosure also relates to cannabinoid-based therapeutics, and their use in treating opioid addiction.

5 Claims, 2 Drawing Sheets

(56) References Cited

OTHER PUBLICATIONS

Appendino G, Chianese G, Taglialatela-Scafati O. Cannabinoids: occurrence and medicinal chemistry. Curr Med Chem. 2011; vol. 18; pp. 1085-1099.
Bachhuber MA, Saloner B, Cunningham CO, Barry CL. Medicinal cannabis laws and opioid analgesic overdose mortality in the United States, 1999-2010. JAMA Intern. Med. 2014, vol. 174; pp. 1668-1673.
Bellnier T, Brown GW, Ortega TR. Preliminary evaluation of the efficacy, safety, and costs associated with the treatment of chronic pain with medical cannabis. Ment Health Clin [Internet]. 2018; vol. 8(3); pp. 110-115.
Boehnke KF, Litinas E and Clauw DJ. Medical cannabis use is associated with decreased opiate medication use in a retrospective cross-sectional survey of patients with chronic pain. J Pain. 2016; vol. 17(6); pp. 739-744.
Breivogel CS, Childers SR. The functional neuroanatomy of brain cannabinoid receptors. Neurobiol Dis. Dec. 1998; vol. 5(6 Pt B):417-431.
Centers for Disease Control and Prevention, National Center for Injury and Prevention Control, Division of Unintentional Injury Prevention. Atlanta, Georgia. U.S. Department of Health and Human Services. "Calculating Total Daily Doses of Opioids for Safer Dosage". www.cdc.gov/drugoverdose/ prescribing/guideline.html. Atlanta, Georgia 2017. (pp. 1-2).
Chiarotti M, Costamagna L. Analysis of 11-nor-9-carboxy-delta (9)-tetrahydrocannabinol in biological samples by gas chromatography tandem mass spectrometry (GC/MS-MS). Forensic Scilnt. 2000; vol. 114; pp. 1-6.
Christensen, R et al., Efficacy and safety of the weight-loss drug rimonabant: a meta-analysis of randomized trials. Lancet. 2007; vol. 370; pp. 1706-1713.
Clinical Trials.gov, Identifier NCT01323569, 2013, 10 pages.
Costa B, Trovato AE, Comelli F, et al. The non-psychoactive cannabis constituent cannabidiol is an orally effective therapeutic agent in rat chronic inflammatory and neuropathic pain. Eur J Pharmacol. 2007; vol. 556; pp. 75-83.
DeVries M, van Rickevorsel DCM, Vissers KCP, Wilder-Smith OHG, van Goor H, Pain and Nociception Neuroscience Research Group. Clin Gastroenterol Hepatol. 2017; vol. 15(7); pp. 1079-1086.
EP Examination Report for 19710540.6 mailed Apr. 4, 2023.
Evans F. Cannabinoids:the separation of central from peripheral effects on a structural basis. Planta Med. 1991; vol. 57; S60-S67.
Gaoni Y and Micholaum R. Isolation, Structure, and Partial Synthesis of an Active Constituent of Hashish.J. Am. Chem. Soc., 1964, 86 (8), pp. 1646-1647.
Gaskin DJ. Richard P. Institute of Medicine Committee on Advancing Pain Research, Care, and Education. Relieving Pain in America: A Blueprint for Transforming Prevention, Care, Education and Research.Washington, DC: The National Academies Press; 2011. Appendix C: The economic costs of pain in the United States; pp. 301-337.
Gaskin DJ. Richard P. The Economic Costs of Pain in the United States. Journal of Pain. 2012; vol. 13(8); pp. 715-724.
Gorzalka BB, Hill MN and Hillard CJ. Regulation of endocannabinoid signaling by stress: implications for stress-related affective disorders. Neurisci Biobehav Rev. 2008; vol. 32; pp. 1152-1160.
Goulle JP, Saussereau E, Lacroix C. Delta-9-tetrahydrocannabinol pharmacokinetics. Ann Pharm Fr. 2008; vol. 66; pp. 232-244.
Grotenhermen F, Russo E. eds.: Cannabis and Cannabinoids: Pharmacology, Toxicology and Therapeutic Potential. Binghampton, NY: The Haeworth Press, 2002.
Guzman M. Cannabinoids: potential anticancer agents. Nat Rev Cancer. 2003; vol. 3(10); pp. 745-755.
Haggerty GC, Deskin R, Kurtz PJ et al. The pharmacological activity of the fatty acid conjugate 11 palmitoyxy-delta 9-tetrahydrocannabinol. Toxicol Appl Pharmacol. 1986; vol. 84; pp. 599-606.

Hall W. and Degenhardt L. Adverse health effects of non-medical cannabis use. Lancet. 2009; vol. 374; pp. 1383-1391.
Halldin MM, Andersson LK, Widman M, Hollister LE. Further urinary metabolites of delta 1-tetrahydrocannabinol in man. Arzneimittelforschung. 1982, vol. 32(9): Abstract.
Hollister LE, Gillespie HK, Ohlsson A et al. Do plasma concentrations of delta 9-tetrahydrocannabinol reflect the degree of intoxication? J Clin Pharmacol 1981; vol. 21; pp. 171-177S.
Howlett AC, Barth F, Bonner TI, Cabral G, Casellas P, Devane WA, Felder CC, Herkenham M, Mackie K, Martin BR, Mechoulam R, Pertwee RG. International Union of Pharmacology. XXVII. Classification of cannabinoid receptors. Pharmacol Rev. Jun. 2002;54(2):161-202.
Hudson BD, Hebert TE, M Kelly ME. Ligand and Heterodimer-Directed Signaling of the CB1 Cannabinoid Receptor. Molecular Pharmacology 2010; vol. 77; pp. 1-9.
Huestis MA, Cone EJ. Urinary excretion half-life of 11-nor-9-carboxy-delta-9-tetrahydrocannabinol in humans. Ther Drug Monit. 1998; vol. 20; pp. 570-576.
Huestis MA, Henningfield JE, Cone EJ. Blood cannabinoids. I. Absorption of THC and formation of 11-OH-THC and THCCOOH during and after smoking marijuana. J Anal Toxicol. 1992; vol. 16; pp. 276-282.
Huestis MA. Pharmacokinetics and metabolism of the plant cannabinoids, delta9-tetrahydrocannabinol, cannabidiol and cannabinol. Handb Exp Pharmacol 2005: pp. 657-690.
Increases in Drug and Opioid Overdose Deaths—United States, 2000-2014. MMWR Morb Mortal Wkly Rep. Jan. 1, 2016; vol. 64(50-51); pp. 1370-1388.
International Search Report and Written Opinion mailed May 29, 2019.
Verson L., Cannabis and the brain. Brain. 2003; vol. 126; pp. 1252-1270.
Izzo AA, Borrelli F, Capasso R, et al. Non-psychotropic plant cannabinoids: new therapeutic opportunities from an ancient herb. Trends Pharmacol Sci. 2009; vol. 30; pp. 515-527.
Izzo AA, Capasso R, Aviello G, et al. Inhibitory effect of cannabichromene, a major non-psychotropic cannabinoid extracted from Cannabis sativa, on inflammation-induced hypermotility in mice. Br J Pharmacol. 2012; vol. 166; pp. 1444-1460.
Johanson EK, Hollister LE, Halldin MM. Urinary elimination half-life of delta-1-tetrahydrocannabinol-7-oic acid in heavy marijuana users after smoking. Journal of Analytical Toxicology, 1989; p. 218-223.
Jones RT, Benowitz N, and Bachman J. Clinical studies of cannabis tolerance and dependence. Ann NY Acad Sci. 1976; vol. 282; pp. 221-239.
Karschner EL, Schwilke EW lowe RH et al. Implications of plasma delta-9-tetrahydrocannabinol, 11-hydroxy-THC and 11-nor-9-carboxy-THC concentrations in chronic cannabis smokers. J Anal Toxicol. 2009; vol. 33; pp. 469-477.
Kelly P, Jones RT. Metabolism of tetrahydrocannabinol in frequent and infrequent marijuana users. J Anal Toxicol. 1992; vol. 16; pp. 228-235.
Kogan NM, Mechoulam R. Cannabinoids in health and disease. Dialogues Clin Neurosci. 2007; vol. 9; pp. 413-430.
La Porta C, Bura SA, Llorente-Onaindia J, et al. Role of the endocannabinoid system in the emotional manifestations of osteoarthritis pain. Pain. 2015; vol. 156; pp. 2001-2012.
Laprairie RB, Bagher, AM, Kelly, ME Denovan-Wright, EM. Cannabidiol is a negative allosteric modulator of the cannabinoid CB1 receptor. Br J Pharmacol. Oct. 2015; 172(20): 4790-4805.
Law B, Mason PA, Moffat AC et al. Forensic aspects of the metabolism and excretion of cannabinoids following oral Ingestion of cannabis resin. J Pharm Pharmacol. 1984; vol. 36; pp. 289-294.
Lemberger L, Axelrod J, Kopin IJ. Metabolism and disposition of delta-9-tetrahydrocannabinol in man. Pharmacol Rev 1971; vol. 23; pp. 371-380.
Lemberger L, Silberstein SD, Axelrod J and Kopin IJ. Marihuana: Studies on the disposition and metabolism of delta-9-tetrahydrocannabinol in man. Science. 2014; vol. 170; pp. 1320-1322.

(56) References Cited

OTHER PUBLICATIONS

Lichtman AH, Lux EA, McQuade R, Rossetti s, Sanchez R, Sun W. Wright S, Kornyeyeva E, Fallon MT. Results of a double-blind, randomized, placebo-controlled study of Nabiximols oromucosal spray as an adjunctive therapy in advanced cancer patients with chronic uncontrolled pain. J Pain Symptom Manage. 2018; vol. 55, pp. 179-188.

Lowe Rh, Abraham TT, Darwin WD et al. Extended urinary Delta9-tetrahydrocannabinol excretion in chronic cannabis users precludes use as a biomarker of new drug exposure. Drug Alcohol Depend. 2009; vol. 105; pp. 24-32.

Lucas P and Walsh Z. Medical cannabis access, use, and substitution for prescription opioids and other substances: A survey of authorized medical cannabis patients. Int J Drug Policy. 2017; vol. 42; pp. 30-35.

Maccarrone M, Maldanado R, Casas M, Henze T, and Centonze D. Cannabinoids therapeutic use: what is our current understanding following the introduction of THC, THC:CBD oromucosal spray and others? Expert Review of Clinical Pharmacology. 2017; vol. 10, pp. 443-455.

Mackie K. Cannabinoid receptors as therapeutic targets. Ann Rev Pharmacol Toxicol. 2006; vol. 46; pp. 101-122.

Maione S, Costa B, Di Marzo V. Endocannabinoids: a unique opportunity to develop multitarget analgesics. Pain. 2013; vol. 154; S87-S93.

Maldonado R, Baños JE, Cabañero D. The endocannabinoid system and neuropathic pain. Pain. 2016; vol. 157; S23-S32.

Manno Je, Manno BR, Kemp PM et al. Temporal indications of marijuana use can be estimated from plasma and urine concentrations of delta-9-tetrahydrocannabinol, 11-hydroxy-delta9-tetrahydrocannabinol, and 11-nor-delta9- letrahydrocannabinol-9-carboxylic acid. J Anal Toxicol. 2001; vol. 25; pp. 538-549.

May MB and Glode AE. Dronabinol for chemotherapy-induced nausea and vomiting unresponsive to anti-emetics. Cancer Manag Res. 2016; 8: 49-55.

McHugh D, Hu SSJ, Rimmerman N et al. N-arachidonoyl glycine, an abundant endogenous lipid, potently drives directed cellular migration trough GPR18, the putative abnormal cannabidiol receptor. Bmc Neuroscience 2010; vol. 11; pp. 11-44.

McPartland JM, Cannabis Systematics at the Levels of Family, Genus, and Species, Cannabis and Cannabinoid Research, vol. 3.1, 2018, p. 203-212.

Mechoulam R and Shvo Y. Hasish. I. The structure of cannabidiol. Tetrahedron. Dec. 1963; 19(12): 2073-8.

Mechoulam R. Plant cannabinoids: a neglected pharmacological treasure trive. Br J Pharmacol. 2005; vol. 146; pp. 913-915.

Miller G. Pot and Pain. Hints are emerging that cannabis could be an alternative to opioid painkillers. Science. 2016, vol. 354; pp. 566-568.

Mills M. Moguls and Mexicans: The American history of cannabis legalization. The New Econom Mar. 27, 2015. theneweconomy.com.

Nahas GG, Greenwood A. The first report of the National Commission on marihuana (1972): signal of misunderstanding or exercise in ambiguity. Bull N Y Acad Med. Jan. 1974;50(1):55-75.

National Cancer Institute: Common Terminology Criteria for adverse Events (CTCAE), Version 4.0 Bethesda, MD. U.S. Department of Health and Human Services, National Institutes of Health, 2010.

National Commission on Marihuana and Drug Abuse: Marihuana: A Signal of Misunderstanding: Technical papers, Appendix, vols. 1 and 2. Washington D.C., Govt. Print. Off. 1972.

National Governors Association Policy Academy Drug Abuse Prevention. "State of Nevada Plan to Reduce Prescription Drug Abuse". Nevada 2017. (pp. 3-56).

Nicholson AN, Turner C, Stone BM, and Robson PJ. Effect of delta-9 tetrahydrocannabinol and cannabidiol on nocturnal sleeep and early morning behavior in young adults. J Clin Psychopharmacol. 2004; vol. 24; pp. 305-323.

Nutt D, King LA, Saulsbury W, and Blakemore C. Development of a rational scale to assess the harm of drugs of potential misuse. Lancet 2007; vol. 369; pp. 1047-1053.

Owens SM, McBAy AJ, Reisner HM, et al. 125I radioimmunoassay of delta-9-tetrahydrocannabinol in blood and plasma with a solid-phase second-antibody separation method. Clin Chem. 1981; vol. 27; pp. 619-624.

Paula-Freire Lig, Andersen ML, Molska GR, and Kohn DO. Evaluation of the Antinociceptive Activity of Ocimum gratissimumL. (Lamiaceae) Essential Oil and its isolated Active Principles in Mice. Phytother Res. 2013; vol. 27; pp. 1220-1224.

Perron Be, Bohnert K, Perone AK, Bonn-Miller MO and Ilgen M. Use of prescription pain medications among medical caanbis patients: comparisons of pain levels, functioning, and patterns of alcohol and other drug use. J Stud Alcohol Drugs.2015; vol. 76(3); pp. 406-413.

Price MR, Baille GL, Thomas A, Stevenson LA, Easson M, Goodwin R, McLean A, McIntosh L, Goodwin G, Walker G, Westwood P, Marrs J, Thomson F, Cowley p. Christopoulos A, Pertwee RG, and Ross RA. Allosteric modulation of the cannabinoid CB1 receptor. Mol Pharmacol. 2005; vol. 68; pp. 1484-1495.

Qin N, Neeper MP, Liu Y, et al. TRPV2 is activated by cannabidiol and mediates CGRP release in cultured rat dorsal root ganglion neurons. J Neurosci. 2008; vol. 28; pp. 6231-6238.

Reiman et al., Cannabis as a Substitute for Opioid-Based Pain Medication: Patient Self Report; Cannabis and Cannabinoid Research, 2017, vol. 2, No. 1, p. 160-166.

Reiter A, Hake J, Meissner C et al. Time of drug elimination in chronic drug abusers. Case study of 52 patients in a "low-step" detoxification ward. Forensic Scilnt. 2001; vol. 119; pp. 248-253.

Rong C, Carmona NE, Lee YL, Ragguett RM, Pan Z, Rosenblat JD, Subramaniapillai M, Shekotikhina M, Almatham F, Alageel A, Mansur R, Ho RC, Mcintyre RS. Drug-drug interactions as a result of co-administering A9-THC and CBD with other psychotropic agents. Expert Opin Drug Saf. Jan. 2018; vol. 17(1); pp. 51-54.

Russo EB. Current Therapeutic Cannabis Controversies and Clinical Trial Design Issues. Front Pharmacol. 2016; vol. 7, pp. 1-19.

Russo EB. Taming THC; potential cannabis synergy and phytocannabinoid-terpenoid entourage effects. Br J Pharmacol. Aug. 2011; 163 (7):1344-1364.

Sink K, Segovia K, Sink J, et al. Potential anxiogenic effects of cannabinoid CB1 receptor anagonists/inverse agonists In rats: Comparisons between AM4113, AM251, and the benzodiazepine inverse agonist FG-7142. Eur Neuropsychopharm. 2010; vol. 20; pp. 112-122.

Smith-Kielland A, Skuterud B, Morland J. Urinary excretion of 11-nor-9-carboxy-delta 9-tetrahydrocannabinol and cannabinoids in frequent and infrequent drug users. J Anal Toxicol. 1999; vol. 23; pp. 323-332.

Solowij N, Stephens RS, Roffman RA et al. Cognitive functioning of long-term heavy cannabis users seeking treatment. JAM. 2002; 287: 1123-31. Erratum in JAMA 2002; V287, No. 9. P1123-1131_1651.

Sutton IR, Daeninck P: Cannabinoids in the management of intractable chemotherapy-induced nausea and vomiting and cancer-related pain. J Support Oncol. 2006; vol. 4(10); pp. 531-535.

Svendsen KB, jensen TS, Bach FW. Does the cannabinoid dronabinol reduce central pain in multiple sclerosis? Randomized doubleblind placebocontrolled crossover trial. BMJmj. 2004, pp. 1-9.

Vermersch P. Sativex® (tetrahydrocannabinol + cannabidiol) and endocannabinoid system modulator: basic features and main clinical data. Expert Rev Neurother. 2011; 114 (Suppl); pp. 15-19.

Ware MA, Wang T, Shapiro S, Collet Jpand the COMPASS study team. Cannabis for the management of pain: Assessment of safety study (Compass). J Pain; Dec. 16, 2015 (12), pp. 1233-1242.

Wechsler H. Marihuana, alcohol and public policy. New Eng. J. Med. 287:515-17, 1972.

Whiting PF, Wolff RE, Deshpande S, Di Niso M, Duffy S, Hernandez AV, Keurentjes JC, Lang S, Misso K, Rider s, Schmidkofer S, Westwood M, Kleijnen J. Cannabinoids for Medical Use: A systematic review and meta-analysis. JAMA. 2015; vol. 313; pp. 2456-2473.

(56) References Cited

OTHER PUBLICATIONS

Wiese et al., Emerging Evidence for Cannabis' Role in Opioid Use Disorder; Cannabis and Cannabinoid Research, 2018, vol. 3, No. 1, p. 1-11.
Wirth PW, Watson ES, ElSohly M, et al. Anti-inflammatory properties of cannabichromene. Life Sci. 1980; vol. 26; pp. 1991-1995.
Yamamoto I, Watanabe K Narimatsu S, and Yoshimura H. Recent advances in the metabolism of cannabinoids. Int J Biochem Cell Biol. 1995; vol. 27; pp. 741-746.
Marshall, Can cannabis kill pain without getting you stoned? CU Boulder Today, Apr. 25, 2018, 3 pages.

\* cited by examiner

| | Starting | Week 1 | Week 2 | Week 3 | Week 4 |
|---|---|---|---|---|---|
| Average | 491.16 | 379.08 | 268.66 | 164.33 | 96.04 |
| Medium | 368 | 300 | 210 | 126 | 70 |
| SD (+/-) | 301.15 | 279.53 | 255.3761 | 213.33 | 141.01 |
| High | 1231 | 1080 | 1080 | 10800 | 630 |
| Low | 300 | 140 | 0 | 0 | 0 |

CANNABIS BASED THERAPEUTIC AND METHOD OF USE

CROSS-REFERENCE

This application is a continuation of U.S. application Ser. No. 16/971,781, filed Aug. 21, 2020, which is a National Stage Application of International Application No. PCT/US2019/019465, filed Feb. 25, 2019, which claims the benefit of U.S. Provisional Application No. 62/634,547, filed Feb. 23, 2018, the disclosures of which are incorporated herein by reference in their entirety.

BACKGROUND OF THE INVENTION

There is a need in the art for methods and compositions to manage pain, e.g., chronic pain. There is also a need in the art for methods and compositions for treating opioid addiction.

SUMMARY OF THE INVENTION

Disclosed herein are pharmaceutical compositions comprising: tetrahydrocannabinol (THC) and cannabidiol (CBD) in a THC:CBD ratio of from 1:1.5 to 3:1 by weight; and one or more terpenes. In some embodiments, the THC:CBD ratio is from 1.5:1 to 2:1. In some embodiments, the THC:CBD ratio is about 1.5:1.

In some embodiments, the pharmaceutical composition comprises about 15-20 mg tetrahydrocannabinol (THC) per dose. In some embodiments, the pharmaceutical composition comprises 10-12 mg cannabidiol (CBD).

In some embodiments, the one or more terpenes comprise β-myrcene, β-caryophyllene, ocimene, α-pinene, α-humulene, linalool, p-cymene, camphene, cis-nerolidol, terpinolene, isopulegol, caryophyllene oxide, δ-limonene, geraniol, guaiol, α-bisabolol, 3-carene, β-pinene, γ-terpinene, or a combination thereof. In some embodiments, rein the one or more terpenes comprise β-myrcene, β-caryophyllene, ocimene, α-pinene, and α-humulene.

In some embodiments, the one or more terpenes comprise β-myrcene, and wherein the pharmaceutical composition comprises 30-60 mg of β-myrcene per dose.

In some embodiments, the one or more terpenes comprise β-caryophyllene, and wherein the pharmaceutical composition comprises 2.5-5 mg of β-caryophyllene per dose.

In some embodiments, the one or more terpenes comprise ocimene, and wherein the pharmaceutical composition comprises 2.3-4.7 mg of ocimene per dose.

In some embodiments, the one or more terpenes comprise α-pinene, and wherein the pharmaceutical composition comprises 1.1-2.1 mg of α-pinene per dose.

In some embodiments, the one or more terpenes comprise α-humulene, and wherein the pharmaceutical composition comprises 0.8-1.6 mg of α-humulene per dose.

In some embodiments, the one or more terpenes comprise β-myrcene, β-caryophyllene, ocimene, α-pinene, and α-humulene; and wherein the pharmaceutical composition comprises about 30-60 mg of the β-mycene, about 2.5-5 mg of the β-caryophyllene, about 2.3-4.7 mg of the ocimene, about 1.1-2.1 mg of the α-pinene, and about 0.8-1.6 mg of the α-humulene per dose.

In some embodiments, the pharmaceutical composition is formulated as a liquid, a pill, a gel capsule, a vaporizable liquid, a vaporizable solid, a transdermal ointment or salve, or a transdermal patch.

In some embodiments, the pharmaceutical composition is formulated as a liquid. In some embodiments, the liquid comprises citric acid, blue agave, glycerine, one or more lorann oils, food coloring, or a combination thereof.

In some embodiments, the liquid comprises: about 1% to 7% w/w citric acid; about 40% to 49% w/w blue agave; about 40% to 49% w/w glycerin; about 0.1% to 1.5% w/w lorann oils; about 0.01 to 0.4% food coloring; or a combination thereof. In some embodiments, the liquid comprises: about 3-5% w/w citric acid; about 45-49% w/w blue agave; about 45-49% w/w glycerin; about 0.7-0.9% w/w lorann oils; and about 0.1-0.3% food coloring.

In some embodiments, the pharmaceutical composition is for use in the treatment of opioid addiction.

In some embodiments, the pharmaceutical composition is for use in the treatment of pain.

In some embodiments, the pharmaceutical composition is for use in the treatment of chemotherapy-induced nausea and vomiting.

Also disclosed herein are methods of treating opioid addition, the methods comprising administering an effective amount of a pharmaceutical composition comprising one or more cannabinoids to a subject in need thereof. The pharmaceutical composition can be any pharmaceutical composition disclosed herein.

In some embodiments, the pharmaceutical composition is administered every 1, 2, 3, 4, 5, 6, 7, 8, 9, 10, 11, 12, 13, 14, 15, 16, 17, 18, 19, 20, 21, 22, 23, or 24 hours.

In some embodiments, the pharmaceutical composition is administered every 6, 8 or 12 hours.

In some embodiments, the subjects opioid use decreases by at least 50% within 5 weeks of beginning treatment as determined by morphine equivalency of opioids used.

INCORPORATION BY REFERENCE

All publications, patents, and patent applications mentioned in this specification are herein incorporated by reference to the same extent as if each individual publication, patent, or patent application was specifically and individually indicated to be incorporated by reference. In the event that a term incorporated by reference conflicts with a term defined herein, this specification shall control.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
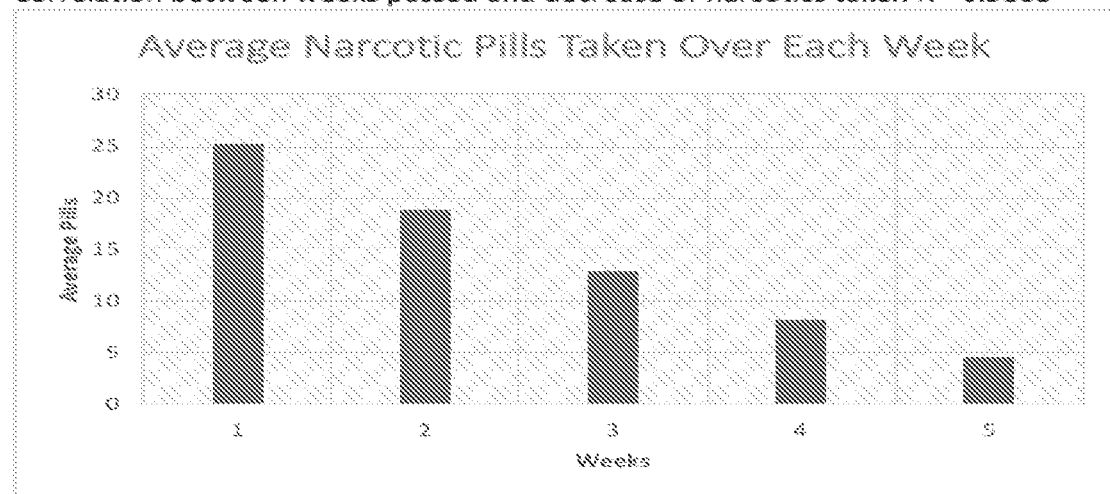
FIGS. 1a & b illustrates weekly pill counts in chart form (FIG. 1a) and graph form with regression analysis (FIG. 1b).

The present disclosure relates to therapeutics, and more especially the use of cannabinoid-based therapeutics, for use in treating those known to have chronic pain. In some cases, the chronic pain may have been treated using opiates. The present disclosure also relates to cannabinoid-based therapeutics for use in treating opioid addiction.

INTRODUCTION

In the United States the estimated total annual cost of pain-related health is approximately $600 billion and perhaps this figure is even higher for the nations in European Union (EU). This estimate includes the actual costs related to the medical care as well as the economic losses which contribute to approximately one-half of these costs. Economic losses include claimed disability, loss of productivity and lost wages. Medical care including physician time, hospitalization, surgical procedures, diagnostic testing and prescription drugs all contribute to the costs associated with the treatment of pain, as well the costs associated with the adverse effects associated with their utilization. Unfortunately, one of the adverse effects associated with prescription painkillers is death. Overdose deaths secondary to prescription opioids were five times higher in 2016 than 1999 and sales of these prescription drugs have quadrupled. That being said, the number of deaths dues to prescription opioids has remained relative stable at approximately 14,000 to 16,000 deaths per year. Much of the increase in mortality related to opioid consumption is due the rapid rise in those associated with the use of synthetic opioids. In states with either medical marijuana or both medical and retail marijuana programs in place there was a 24.8% lower mean annual opioid overdose mortality rate (95% CI, −37.5% to −9.5%: P=0.003) compared with states without medical marijuana laws.

Addressing the opiate crisis in this country has led to a number of studies being conducted using *cannabis*-based therapy as an alternative means of managing chronic and cancer-related pain. Despite Nabiximols not appearing to be statistically superior when compared to placebo in controlling pain in cancer patients, there are other randomized placebo controlled trials demonstrating the efficacy of using *cannabis* for pain control. There is also significant evidence that a *cannabis*-opioid interaction exists that results in improved pain control. All of the studies to date have either used pain scales or patient interview results to determine the success or failure of the *cannabis* intervention.

A group of physicians in Nevada, licensed to cultivate, produce and sell *cannabis*-related products and have recently undertaken a two phase II trials ran using a guava-based syrup with a THC:CBD ratio of 2:1 and at a 1:1 ratio containing only the flavored guava-based syrup. Each dose of syrup contained either 10 mg/ml of both delta-9-tetra-cannabinol (THC) and cannabidiol (CBD) or 20 mg of THC and 10 mg of CBD. As a proof of concept 25 patients in each group with a history of at least 3 years of chronic opiate use were enrolled in a single arm study with the endpoint being a 30% reduction of opiate intake determined by weekly pill count. 23 of the 25 patients reduced their opiate intake by greater than 50%. This provides an objective basis to evaluate the potential of *cannabis* to reduce the opiate consumption across the US.

The claimed beneficial medicinal effects associated with *cannabis* consumption are quite diverse and of long-standing. In 1889, some of these benefits were first described in the medical literature by Dr. E. A. Birch. Of the claims made, the most studied are in patients with multiple sclerosis, where a beneficial effect on muscle spasticity and pain are well-documented, but not necessarily as consistently as one might like. *Cannabis* has also been shown to be effective in treating seizures, anorexia, chronic pain, and nausea and vomiting that is associated with chemotherapy. There is some evidence that cannabidiols have a therapeutic effect of inflammation, chronic pain, diabetes, cancer, and neurodegenerative diseases.

To understand the underlying basis for the use of cannabinoids in the treatment of chronic pain it is imperative to understand their likely mechanisms of action. *Cannabis* contains at least 63 cannabinoids but two are best understood studied. The first, delta-9 tetrahydrocannabinol (THC), is responsible for the psychoactive effects that is widely associated with *cannabis*. The other main active component, cannabidiol (CBD), has no psychoactive effect associated with its consumption but is thought to provide anti-neoplastic, analgesic and antineuroleptic effects per the literature. Even though both cannabinoids are present in every plant, the interactions with the cerebral endocannabinoid receptor system are quite different. CBD binds as an antagonist to the cannabinoid receptor CB1 but the bond between THC and the same receptor is at least 100 times stronger. CBD also antagonizes the action on the cannabinoid G protein-coupled receptor GPR55, which is thought to be responsible the different neuromodulatory actions as the CB1 receptor. Claims of the subjective effects associated with *cannabis* ingestion include improvement in mood; relaxation; and increased sensitivity. On the other hand THC ingestion has been associated with less than desirable adverse effects such as agitation; panic disorder; depression and even psychosis.

Cannabinoids have an effect on serotonergic systems, including increasing cerebral production of 5-hydroxytryptamine (5-HT), serotonin while decreasing its uptake at the synapse level. THC has been found to have dopaminergic antagonistic actions which may contribute to its beneficial profile regarding pain control.

Other phytocannabinoids such as cannabichromene (CBC), cannabigerol (CBG) as well as a number of terpenoids likely contribute its analgesic effect. CBC and CBG have significant anti-inflamatory and analgesic effects over and beyond that associated with THC. B-caryophyllene has been shown to be a selective CB2 agonist and other terpenes such as linalool and a-Pinene have analgesic and anti-inflamatory effects respectively. Myrcene other the other hand has been shown to have analgesic effects mediated through an opioid-like action. This is an important development as it helps explain another avenue as to how *cannabis* and it component parts may prevent opiate withdrawal and allow for the use of lesser amounts of opioids while preventing the development of tolerance. Used in combination with opioid pain medications, *cannabis* can lower opioid side effects, cravings, and withdrawal severity, as well as enhance the analgesic effects of opioids, thereby allowing for lower doses and less risk of overdose.

As explained above the actions of THC, CBD, associated terpenes are potentially complementary and there is substantial evidence to suggest benefit of using together for patients with chronic pain.

Embodiments of the Disclosure

An embodiment of the present disclosure is the therapeutic compound for the use in treating chronic pain and like disorders and preferably in liquid form compromising a formulation including cannabinoids, but not limited to delta-9—tetrahydrocannabinol and cannabidiol. The compound may optionally include any terpene or terpinoid present in a *cannabis* plant. A subject suffering from chronic pain is orally administered a therapeutically effective amount of the compound so as to alleviate, cure or prevent the symptoms associated with chronic pain.

Another embodiment of the present disclosure is the therapeutic compound for the use in treating chronic pain and like disorders and preferably in a pill form comprising a formulation including cannabinoids, but not limited to delta-9-tetrahydrocannabinol and cannabidiol. The compound may optionally include any terpene or terpinoid present in a *cannabis* plant. A subject suffering from chronic pain is orally administered a therapeutically effective amount of the compound so as to alleviate, cure or prevent the symptoms associated with chronic pain Another embodiment of the present disclosure is the therapeutic compound for the use in treating chronic pain and like disorders and preferably in suppository form compromising a formulation including cannabinoids, but not limited to delta-9-tetrahydrocannabinol and cannabidiol. The compound may optionally include any terpene or terpinoid present in a *cannabis* plant. A subject suffering from chronic pain is orally administered a therapeutically effective amount of the compound so as to alleviate, cure or prevent the symptoms associated with chronic pain Another embodiment of the present disclosure is the therapeutic compound for the use in treating chronic pain and like disorders and preferably in capsule form compromising a formulation including cannabinoids, but not limited to delta-9-tetrahydrocannabinol and cannabidiol. The compound may optionally include any terpene or terpinoid present in a *cannabis* plant. A subject suffering from chronic pain is orally administered a therapeutically effective amount of the compound so as to alleviate, cure or prevent the symptoms associated with chronic pain.

Another embodiment of the present disclosure is the therapeutic compound for the use in treating chronic pain and like disorders and preferably in a transdermal form compromising a formulation including cannabinoids, but not limited to delta-9-tetrahydrocannabinol and cannabidiol. The compound may optionally include any terpene or terpinoid present in a *cannabis* plant. A subject suffering from chronic pain is transdermally administered a therapeutically effective amount of the compound so as to alleviate, cure or prevent the symptoms associated with chronic pain.

Another embodiment of the present disclosure is the therapeutic compound for the use in treating chronic pain and like disorders and preferably in an inhalable/nebulized form compromising a formulation including cannabinoids, but not limited to delta-9-tetrahydrocannabinol and cannabidiol. The compound may optionally include any terpene or terpinoid present in a *cannabis* plant. A subject suffering from chronic pain is inhaled in a therapeutically effective amount of the compound so as to alleviate, cure or prevent the symptoms associated with chronic pain It shall be noted that the cannabinoid disclosed herein may include any of the identified cannabinoids, but not limited to THC (Tetrahydrocannabinol); THCA (Tetrahydrocannabinolic acid); CBD (Cannabidiol); CBDA (Cannabidiolic Acid); CBN (Cannabinol); CBG (Cannabigerol); CBC (Cannabichromene); CBL (Cannabicyclol); CBV (Cannabivarin); THCV (Tetrahydrocannabivarin); CBDV (Cannabidivarin); CBCV (Cannabichromevarin); CBGV (Cannabigerovarin); CBGM (Cannabigerol Monomethyl Ether); CBE (Cannabielsoin); CBT (Cannabicitran); (OTHC) 10-Oxo-delta-6a-tetrahydrocannabinol; (CBCF) Cannabichromanon; (CBF) Cannabifuran; Cannabiglendol; (CBR) Cannabiripsol; (CBT)Cannbicitran; (DCBF) Dehydrocannabifuran; (cis-THC) Delta-9-cis-tetrahydrocannabinol; (triOH-THC) Tryhydroxy-delta-9-tetrahydrocannabinol; and OH-iso-HHCV.

It shall also be noted that the terpene disclosed herein may, but is not limited to, any single or combination of the terpenes listed in table 1.

TABLE 1

List of exemplary terpenes

| No. | chemical name | RI (DB1) | formula | MW |
|---|---|---|---|---|
| 1 | Fusicocca-3,5-diene | 1850 | C20H32 | 272 |
| 2 | 9-epi-Sclarene | 1896 | C20H32 | 272 |
| 3 | Laurenene | 1903 | C20H32 | 272 |
| 4 | Rimuene | 1907 | C20H32 | 272 |
| 5 | Isopimara-8,15-diene | 1922 | C20H32 | 272 |
| 6 | Cembrene | 1938 | C20H32 | 272 |
| 7 | Pimara-8,15-diene | 1942 | C20H32 | 272 |
| 8 | Sclarene | 1943 | C20H32 | 272 |
| 9 | Isohibaene | 1944 | C20H32 | 272 |
| 10 | Rosa-5,15-diene | 1945 | C20H32 | 272 |
| 11 | (E)-2,6-Dimethyl-10-(p-tolyl)-undeca-2,6-diene | 1945 | C20H30 | 270 |
| 12 | Isocembrene | 1951 | C20H32 | 272 |
| 13 | Beyerene | 1951 | C20H32 | 272 |
| 14 | Pimara-8(14),15-diene | 1955 | C20H32 | 272 |
| 15 | Cembrene A | 1962 | C20H32 | 272 |
| 16 | Labda-7,13,14-triene | 1978 | C20H32 | 272 |
| 17 | Isopimara-8(14),15-diene | 1981 | C20H32 | 272 |
| 18 | Isophyllocladene | 1982 | C20H32 | 272 |
| 19 | Dolabella-6,10,15-triene | 1984 | C20H32 | 272 |
| 20 | (Z)-Biformene | 1988 | C20H32 | 272 |
| 21 | Manool oxide | 2007 | C20H34O | 290 |
| 22 | Geranyllinalool | 2008 | C20H32 | 272 |
| 23 | Isopimara-7,15-diene | 2010 | C20H32 | 272 |
| 24 | 15-Kaurene | 2011 | C20H32 | 272 |
| 25 | Isopimara-8,15-diene | 2016 | C20H32 | 272 |
| 26 | Dolabradiene | 2017 | C20H32 | 272 |
| 27 | Trachylobane | 2022 | C20H32 | 272 |
| 28 | (E)-Biformene | 2017 | C20H32 | 272 |

TABLE 1-continued

List of exemplary terpenes

| No. | chemical name | RI (DB1) | formula | MW |
|---|---|---|---|---|
| 29 | Cembrene C | 2023 | C20H32 | 272 |
| 30 | 13-epi-Manoyl oxide | 2023 | C20H34O | 290 |
| 31 | (E)-Labda-7,12,14-triene | 2036 | C20H32 | 272 |
| 32 | Phyllocladene | 2042 | C20H32 | 272 |
| 33 | Abietatriene | 2046 | C20H30 | 270 |
| 34 | 16-Atisirene | 2051 | C20H32 | 272 |
| 35 | 16-Kaurene | 2056 | C20H32 | 272 |
| 36 | Manool | 2070 | C20H32 | 272 |
| 37 | Aphidicol-15-ene | 2073 | C20H32 | 272 |
| 38 | Valpara-2,15-diene | 2073 | C20H32 | 272 |
| 39 | Abieta-7,13-diene | 2084 | C20H32 | 272 |
| 40 | Labda-7,14-dien-13-ol | 2096 | C20H34O | 290 |
| 41 | Aphidicol-16-ene | 2102 | C20H32 | 272 |
| 42 | Isoabienol | 2124 | C20H34O | 290 |
| 43 | Abieta-8(14),13(15)-diene | 2152 | C20H32 | 272 |
| 44 | (8a,12Z)-Abienol | 2146 | C20H34O | 290 |
| 45 | Incensole | 2193 | C20H34O2 | 306 |
| 46 | Sclareol | 2231 | C20H36O2 | 308 |
| 47 | Labda-8(17),14-dien-6,13-diol | 2248 | C20H34O2 | 306 |
| 48 | Incensol acetate | 2220 | C22H36O3 | 348 |
| 49 | Verticilla-4(20),7,11-triene | 2040 | C20H32 | 272 |
| 50 | m-Camphorene | 1947 | C20H32 | 272 |
| 51 | p-Camphorene | 1980 | C20H32 | 272 |
| 52 | Cembrenol | 2131 | C20H34O | 290 |
| 53 | Sterna-13-ene | 2025 | C20H32 | 272 |
| 54 | 2-Allyl-4-methylphenol | 1262 | C10H12O | 148 |
| 55 | 8,9-Dehydrothymol acetate | 1360 | C12H14O2 | 190 |
| 56 | 3,5,5-Trimethyl-4-methylenecyclohex-2-enone | 1200 | C10H14O | 150 |
| 57 | Cabreuva oxide D | 1467 | C15H24O | 220 |
| 58 | p-Isopropylbenzaldehyd | 1220 | C10H12O | 148 |
| 59 | 3-Methyl-4-(2,6,6-trimethylcyclohex-2-enyl)-but-3-en-2-one | 1471 | C14H22O | 206 |
| 60 | 2,6,6-Trimethyl-3-oxocyclohex-1-ene-1-carbaldehyde | 1110 | C10H14O2 | 166 |
| 61 | Isophorone | 1100 | C9H14O | 138 |
| 62 | 3,5,5-Trimethylcyclohex-3-enone | 1027 | C9H14O | 138 |
| 63 | trans-Sabinyl acetate | 1278 | C12H16O2 | 192 |
| 64 | Nerol | 1210 | C10H18O | 154 |
| 65 | 3a-Hydroxy-1,8-cineol | 1217 | C10H18O2 | 170 |
| 66 | Carvone | 1214 | C10H14O | 150 |
| 67 | Thymol methyl ether | 1215 | C11H16O | 164 |
| 68 | Pulegone | 1215 | C10H16O | 152 |
| 69 | Neral | 1215 | C10H16O | 152 |
| 70 | p-Anisaldehyde | 1218 | C8H8O2 | 136 |
| 71 | Chavicol | 1219 | C9H10O | 134 |
| 72 | 2,3-Dehydro-1,4-cineol | 1219 | C10H16O | 152 |
| 73 | trans-Isopulegone | 1161 | C10H16O | 152 |
| 74 | Piperitone | 1226 | C10H16O | 152 |
| 75 | 1,4-Dimethoxy-2-methylbenzene | 1226 | C9H12O2 | 152 |
| 76 | Carvacrol methyl ether | 1226 | C11H16O | 164 |
| 77 | Isobornyl formate | 1228 | C11H18O2 | 182 |
| 78 | 2-Phenylethyl acetate | 1230 | C10H12O2 | 164 |
| 79 | (E)-Cinnamaldehyde | 1234 | C9H8O | 132 |
| 80 | 2,3-Dehydro-1,8-cineol | 993 | C10H16O | 152 |
| 81 | 2-Hydroxypinan-3-one | 1235 | C10H16O2 | 168 |
| 82 | Geraniol | 1235 | C10H18O | 154 |
| 83 | Pseudodiosphenol | 1245 | C10H16O2 | 168 |
| 84 | cis-Chrysanthenyl acetate | 1253 | C12H18O2 | 194 |
| 85 | trans-Carvone epoxide | 1243 | C10H14O2 | 166 |
| 86 | cis-Sabinene hydrat acetate | 1248 | C12H20O2 | 196 |
| 87 | cis-Ethyl chrysanthemate | 1251 | C12H20O2 | 196 |
| 88 | trans-Sabinen hydrate acetate | 1254 | C12H20O2 | 196 |
| 89 | Citronellyl formate | 1259 | C11H20O2 | 184 |
| 90 | Perilla aldehyde | 1260 | C10H14O | 150 |
| 91 | trans-Ethyl chrysanthemate | 1260 | C12H20O2 | 196 |
| 92 | trans-Anethol | 1262 | C10H12O | 148 |
| 93 | Nonanoic acid | 1263 | C9H18O2 | 158 |
| 94 | Isopulegol acetate (Isomer 1) | 1263 | C12H20O2 | 196 |
| 95 | Methyl nerolate | 1265 | C11H18O2 | 182 |
| 96 | Safrol | 1265 | C10H10O2 | 162 |
| 97 | cis-Thiorose oxide | 1265 | C10H18S | 170 |
| 98 | cis-Verbenyl acetate | 1266 | C12H18O2 | 194 |
| 99 | Thymol | 1267 | C10H14O | 150 |

TABLE 1-continued

List of exemplary terpenes

| No. | chemical name | RI (DB1) | formula | MW |
|---|---|---|---|---|
| 100 | Bornyl acetate | 1270 | C12H20O2 | 196 |
| 101 | Neomenthyl acetate | 1263 | C12H22O2 | 198 |
| 102 | Deca-2,4-dienal | 1270 | C10H16O | 152 |
| 103 | Isopulegol acetate (Isomer 2) | 1271 | C12H20O2 | 196 |
| 104 | 2-Undecanone | 1273 | C10H16O | 152 |
| 105 | 4,8-Dimethylnonanol | 1276 | C11H24O | 172 |
| 106 | Diosphenol | 1276 | C10H16O2 | 168 |
| 107 | Isobornyl acetate | 1276 | C12H20O2 | 196 |
| 108 | Carvacrol | 1278 | C10H14O | 150 |
| 109 | Thujopsadiene | 1470 | C15H22 | 202 |
| 110 | Sesamol | 1280 | C7H6O3 | 138 |
| 111 | Menthyl acetate | 1280 | C12H22O2 | 198 |
| 112 | Geranial | 1244 | C10H16O | 152 |
| 113 | Geranyl formate | 1284 | C11H18O2 | 182 |
| 114 | trans-Thiorose oxide | 1284 | C10H18S | 170 |
| 115 | 2-Undecanol | 1284 | C11H24O | 172 |
| 116 | p-Isopropylbenzyl alcohol | 1285 | C10H14O | 150 |
| 117 | Sencyunolide | 1672 | C12H16O2 | 192 |
| 118 | trans-Pinocarvyl acetate | 1287 | C12H18O2 | 194 |
| 119 | 2,3,6-Trimethylbenzaldehyde | 1287 | C10H12O | 148 |
| 120 | Terpinen-4-ol acetate | 1289 | C12H20O2 | 196 |
| 121 | Chrysanthenone epoxide | 1290 | C10H14O2 | 166 |
| 122 | (E,E)-Deca-2,4-dienal | 1291 | C10H16O | 152 |
| 123 | Puleganolide (Isomer 1) | 1292 | C10H16O2 | 168 |
| 124 | Dihydrocarveol acetate (Isomer 2) | 1295 | C12H20O2 | 196 |
| 125 | Isoascaridol | 1295 | C10H16O2 | 168 |
| 126 | Theaspirane (Isomer 1) | 1299 | C13H22O | 194 |
| 127 | cis-Pinocarvyl acetate | 1300 | C12H18O2 | 194 |
| 128 | Dihydronaginata ketone | 1300 | C10H14O2 | 166 |
| 129 | Naginata ketone alcohol | 1306 | C10H14O3 | 182 |
| 130 | Puleganolide (Isomer 2) | 1305 | C10H16O2 | 168 |
| 131 | Methyl geranate | 1306 | C11H18O2 | 182 |
| 132 | Vinylguaiacol | 1311 | C9H10O2 | 150 |
| 133 | 5-Acetoxylinalool | 1303 | C12H20O3 | 212 |
| 134 | Theaspirane (Isomer 2) | 1313 | C13H22O | 194 |
| 135 | Chavicol acetate | 1313 | C11H12O2 | 176 |
| 136 | Myrtenyl acetate | 1313 | C12H18O2 | 194 |
| 137 | Dihydrocarveol acetate (Isomer 2) | 1314 | C12H20O2 | 196 |
| 138 | Apiol | 1649 | C12H14O4 | 222 |
| 139 | trans-Carvyl acetate | 1318 | C12H18O2 | 194 |
| 140 | Thymol acetate | 1329 | C12H16O2 | 192 |
| 141 | Menthothiophene | 1330 | C10H14S | 166 |
| 142 | 2,3,4-Trimethylbenzaldehyde | 1331 | C10H12O | 148 |
| 143 | Eugenol | 1331 | C10H12O2 | 164 |
| 144 | cis-Dihydrocarvone epoxide | 1333 | C10H16O2 | 168 |
| 145 | Ethyl nerolat | 1335 | C12H20O2 | 196 |
| 146 | Fragranol | 1201 | C12H20O2 | 196 |
| 147 | 7,8-Dihydro-b-ionone | 1422 | C13H22O | 194 |
| 148 | 8-Hydroxylinalool | 1336 | C10H18O2 | 170 |
| 149 | 3,4-Dimethoxystyrene | 1337 | C10H12O2 | 164 |
| 150 | Citronellyl acetate | 1337 | C12H22O2 | 198 |
| 151 | trans-8-Mercapto-p-menthan-3-one | 1340 | C10H18OS | 186 |
| 152 | Anhydroencecalinol | 1640 | C14H16O2 | 216 |
| 153 | Neryl acetate | 1342 | C12H20O2 | 196 |
| 154 | Dihydrocarveol acetate (Isomer 2) | 1342 | C12H20O2 | 196 |
| 155 | exo-Isocamphanyl acetate | 1345 | C12H20O2 | 196 |
| 156 | cis-Carvyl acetate | 1345 | C12H18O2 | 194 |
| 157 | (Z)-Ethyl cinnamate | 1344 | C11H12O2 | 176 |
| 158 | Chavibetol (m-Eugenol) | 1346 | C10H12O2 | 164 |
| 159 | 4-Methoxyphenylethanol | 1347 | C9H12O2 | 152 |
| 160 | (E)-Anethol epoxide | 1347 | C10H12O2 | 164 |
| 161 | trans-Dihydrocarvone epoxide | 1352 | C10H16O2 | 168 |
| 162 | endo-Isocamphanyl acetate | 1352 | C12H20O2 | 196 |
| 163 | (E)-Methyl cinnamate | 1354 | C10H10O2 | 162 |
| 164 | cis-8-Mercapto-p-menthan-3-one | 1356 | C10H18OS | 186 |
| 165 | Dihydrojasmone | 1361 | C10H14O2 | 166 |
| 166 | (E)-b-Damascenone | 1363 | C13H18O | 190 |
| 167 | 3-Allyl-1,4-dimethoxybenzene | 1370 | C11H14O2 | 178 |
| 168 | (Z)-Jasmone | 1371 | C11H16O | 164 |
| 169 | Isobornyl propionate | 1375 | C13H22O2 | 210 |
| 170 | Ethyl geranate | 1377 | C12H20O2 | 196 |
| 171 | Methyl perillate | 1381 | C11H16O2 | 180 |
| 172 | (Z)-Isoeugenol | 1381 | C10H12O2 | 164 |
| 173 | Osmorhizol | 1383 | C11H14O2 | 178 |
| 174 | 2-Dodecanol | 1387 | C12H26O | 186 |

TABLE 1-continued

List of exemplary terpenes

| No. | chemical name | RI (DB1) | formula | MW |
|---|---|---|---|---|
| 175 | 1-Tetradecene | 1387 | C14H28 | 196 |
| 176 | Davanafuran | 1394 | C14H20O2 | 220 |
| 177 | Methyl 4-methoxyphenylacetate | 1398 | C10H12O3 | 180 |
| 178 | (E)-b-Damascone | 1398 | C13H20O | 192 |
| 179 | trans-Carvyl propionate | 1402 | C13H20O2 | 208 |
| 180 | 2,6-Dimethoxycymene | 1402 | C12H18O2 | 194 |
| 181 | Nerylacetone | 1412 | C13H22O | 194 |
| 182 | 2-Hydroxy-1,2-dihydrolavandulyl acetate | 1416 | C12H22O3 | 214 |
| 183 | (Z)-1,2-Dimethoxy-4-propenylbenzene | 1419 | C11H14O2 | 178 |
| 184 | (E)-Cinnamyl acetate | 1420 | C11H12O2 | 176 |
| 185 | Isobornyl isobutyrate | 1424 | C14H24O2 | 224 |
| 186 | Citronellyl propionate | 1427 | C13H24O2 | 212 |
| 187 | 3,4-Dimethoxybenzaldehyde | 1428 | C9H10O3 | 166 |
| 188 | (E)-Isoeugenol | 1429 | C10H12O2 | 164 |
| 189 | cis-Carvyl propionate | 1436 | C13H20O2 | 208 |
| 190 | Massoialactone | 1439 | C10H16O2 | 168 |
| 191 | d-Undecanolide | 1565 | C11H20O2 | 184 |
| 192 | Nordavanone | 1451 | C11H18O2 | 182 |
| 193 | 8-Dehydrothymol isobutyrate | 1458 | C14H18O2 | 218 |
| 194 | (E)-1,2-Dimethoxy-4-propenylbenzene | 1460 | C11H14O2 | 178 |
| 195 | Thymol isobutyrate | 1462 | C14H20O2 | 220 |
| 196 | Isobornyl butyrate | 1462 | C14H24O2 | 224 |
| 197 | 3,4-Dimethoxybenzyl alcohol | 1464 | C9H12O3 | 168 |
| 198 | Sarisane | 1466 | C11H12O3 | 192 |
| 199 | 2-Tridecanone | 1477 | C13H26O | 198 |
| 200 | 2-Tridecanol | 1490 | C13H28O | 200 |
| 201 | Davana ether | 1489 | C15H22O2 | 234 |
| 202 | a-Campholenyl formate | 1240 | C11H18O2 | 182 |
| 203 | Chavibetyl acetate | 1488 | C12H14O3 | 206 |
| 204 | Homovanilline alcohol | 1494 | C9H12O3 | 168 |
| 205 | Davana ether (Isomer) | 1507 | C15H22O2 | 234 |
| 206 | Isobornyl isovalerate | 1516 | C15H26O2 | 238 |
| 207 | Citronellyl butyrate | 1516 | C14H26O2 | 226 |
| 208 | Elemicine | 1522 | C12H16O3 | 208 |
| 209 | Flavesone | 1526 | C14H20O4 | 252 |
| 210 | allo-Davanone | 1539 | C15H24O2 | 236 |
| 211 | Isodavanone | 1545 | C15H24O2 | 236 |
| 212 | Eupatoriochromene | 1726 | C13H16O3 | 220 |
| 213 | cis-Davanone | 1557 | C15H24O2 | 236 |
| 214 | Geranyl crotonate | 1555 | C14H22O2 | 222 |
| 215 | Diethylphthalate | 1555 | C12H14O4 | 222 |
| 216 | cis-8-Acetylthio-p-menthan-3-one | 1559 | C12H20O2S | 228 |
| 217 | 4-Allyl-2,6-dimethoxyphenol | 1561 | C11H14O3 | 194 |
| 218 | Sandela | 1568 | C16H28O | 236 |
| 219 | trans-8-Acetylthio-p-mentan-3-one | 1570 | C12H20O2S | 228 |
| 220 | (Z)-Asarone | 1584 | C12H16O3 | 208 |
| 221 | (Z)-3-Hexenyl benzoate | 1545 | C13H16O2 | 204 |
| 222 | Geranyl 2-methylbutyrate | 1591 | C15H26O2 | 238 |
| 223 | 1,2-Diacetoxy-4-allylbenzene | 1602 | C13H14O4 | 234 |
| 224 | Leptospermone | 1611 | C15H22O4 | 266 |
| 225 | (Z)-Ethyl p-methoxycinnamate | 1614 | C12H14O3 | 206 |
| 226 | Butylphthalide | 1616 | C12H14O2 | 190 |
| 227 | (E)-Asarone | 1636 | C12H16O3 | 208 |
| 228 | (Z)-Butylidenphthalide | 1644 | C12H12O2 | 188 |
| 229 | 6-Methoxythymol isobutyrate | 1658 | C15H22O3 | 250 |
| 230 | 2-Pentadecanone | 1688 | C15H30O | 226 |
| 231 | (E)-Ethyl p-methoxycinnamate | 1711 | C12H14O3 | 206 |
| 232 | (Z)-Ligustilide | 1732 | C12H14O2 | 190 |
| 233 | Heyderiol | 2374 | C22H30O4 | 358 |
| 234 | (E)-Ligustilide | 1782 | C12H14O2 | 190 |
| 235 | 7,11-Dimethylheptadecane | 1792 | C19H40 | 268 |
| 236 | Avocadynofuran | 1796 | C17H26O | 246 |
| 237 | Galaxolide | 1838 | C18H26O | 258 |
| 238 | Traseolide | 1840 | C18H26O | 258 |
| 239 | Tonalide | 1850 | C18H26O | 258 |
| 240 | 1-Nonadecene | 1875 | C19H38 | 266 |
| 241 | Nonadecane | 1900 | C19H40 | 268 |
| 242 | Falcarinol | 2028 | C17H24O | 244 |
| 243 | Trichocoleine | 1875 | C14H18O4 | 250 |
| 244 | Ambrettolide | 1905 | C16H28O2 | 252 |
| 245 | Methyl 4-Hydroxy-3-methoxy-5-(1,1-dimethylprop-2-enyl)-benzoate | 1833 | C14H18O4 | 250 |

TABLE 1-continued

List of exemplary terpenes

| No. | chemical name | RI (DB1) | formula | MW |
|---|---|---|---|---|
| 246 | (E)-Benzyl cinnamate | 2023 | C16H14O2 | 238 |
| 247 | trans-Pinocarvyl formate | 1228 | C11H16O2 | 180 |
| 248 | Hex-5-en-1-ol | 820 | C6H12O | 100 |
| 249 | Hex-5-en-3-ol | 832 | C6H12O | 100 |
| 250 | 1-Hexanol | 837 | C6H14O | 102 |
| 251 | (Z)-Hex-3-en-1-ol | 851 | C6H12O | 100 |
| 252 | (E)-Hex-3-en-1-ol | 851 | C6H12O | 100 |
| 253 | (Z)-Hex-2-en-1-ol | 861 | C6H12O | 100 |
| 254 | 2-Heptanone | 871 | C7H14O | 114 |
| 255 | 2-Heptanol | 880 | C7H16O | 116 |
| 256 | 3-Heptanol | 877 | C7H16O | 116 |
| 257 | n-Heptanal | 882 | C7H14O | 114 |
| 258 | Santene | 884 | C9H14 | 122 |
| 259 | 2-Methyl-1-hexanol | 917 | C7H16O | 116 |
| 260 | Tricyclene | 927 | C10H16 | 136 |
| 261 | a-Pinene | 936 | C10H16 | 136 |
| 262 | Benzaldehyde | 941 | C7H6O | 106 |
| 263 | a-Fenchene | 941 | C10H16 | 136 |
| 264 | Thuja-2,4(10)-diene | 946 | C10H14 | 134 |
| 265 | 6-Methyl-2-heptanol | 950 | C8H18O | 130 |
| 266 | Camphene | 950 | C10H16 | 136 |
| 267 | 1-Octen-3-ol | 962 | C8H16O | 128 |
| 268 | 3-Octanone | 969 | C8H16O | 128 |
| 269 | 4-Octanol | 973 | C8H18O | 130 |
| 270 | 2-Octanol | 981 | C8H18O | 130 |
| 271 | 3-Octanol | 981 | C8H18O | 130 |
| 272 | 2-Pentylfuran | 981 | C9H14O | 138 |
| 273 | Yomogialcohol | 991 | C10H18O | 154 |
| 274 | 3,6-Dimethyl-3-heptanol | 990 | C9H20O | 144 |
| 275 | D 2-Carene | 1000 | C10H16 | 136 |
| 276 | a-Phellandrene | 1002 | C10H16 | 136 |
| 277 | (Z)-Hex-3-enyl acetate | 1002 | C8H14O2 | 142 |
| 278 | p-Methylanisol | 1004 | C8H10O | 122 |
| 279 | Benzyl alcohol | 1006 | C7H8O | 108 |
| 280 | D 3-Carene | 1010 | C10H16 | 136 |
| 281 | Phenylacetaldehyde | 1012 | C8H8O | 120 |
| 282 | m-Cymene | 1013 | C10H14 | 134 |
| 283 | p-Cymene | 1015 | C10H14 | 134 |
| 284 | Salicylaldehyde | 1020 | C7H6O2 | 122 |
| 285 | Limonene | 1025 | C10H16 | 136 |
| 286 | 1,8-Cineol | 1024 | C10H18O | 154 |
| 287 | (Z)-b-Ocimene | 1029 | C10H16 | 136 |
| 288 | (E)-2-Octenal | 1034 | C8H14O | 126 |
| 289 | 5,5-Dimethylbut-3-enolide | 916 | C6H8O2 | 112 |
| 290 | Methyl 3-methylfuroate | 1038 | C7H8O3 | 140 |
| 291 | (E)-b-Ocimene | 1041 | C10H16 | 136 |
| 292 | Oct-3-en-1-ol (Isomer 1) | 1044 | C8H16O | 128 |
| 293 | Artemisia ketone | 1044 | C10H16O | 152 |
| 294 | cis-Dihydroroseoxide | 1047 | C10H20O | 156 |
| 295 | d-Terpineol | 1155 | C10H16O | 152 |
| 296 | g-Terpinene | 1051 | C10H16 | 136 |
| 297 | trans-Sabinene hydrate | 1053 | C10H18O | 154 |
| 298 | Dihydromyrcenol | 1058 | C10H20O | 156 |
| 299 | Non-1-en-3-ol | 1058 | C9H18O | 142 |
| 300 | trans-Linalooloxide (furanoid) | 1058 | C10H20O2 | 172 |
| 301 | p-Mentha-3,8-diene | 1059 | C10H16 | 136 |
| 302 | Benzyl formate | 1060 | C8H8O2 | 136 |
| 303 | m-Cresol | 1061 | C7H8O | 108 |
| 304 | p-Cresol | 1062 | C7H8O | 108 |
| 305 | 1-Octanol | 1063 | C8H18O | 130 |
| 306 | Fenchone | 1069 | C10H16O | 152 |
| 307 | o-Guiacol | 1072 | C7H8O2 | 124 |
| 308 | Methyl benzoate | 1072 | C8H8O2 | 136 |
| 309 | cis-Linalool oxide (furanoid) | 1072 | C10H18O2 | 170 |
| 310 | Artemisia alcohol | 1073 | C10H18O | 154 |
| 311 | Dehydrolinalool | 1073 | C10H16O | 152 |
| 312 | trans-Dihydroroseoxide | 1075 | C10H20O | 156 |
| 313 | 4-Nonanol | 1076 | C9H20O | 144 |
| 314 | Terpinolene | 1082 | C10H16 | 136 |
| 315 | cis-Sabinene hydrate | 1082 | C10H18O | 154 |
| 316 | 2-Nonanol | 1085 | C9H20O | 144 |
| 317 | Linalool | 1086 | C10H18O | 154 |
| 318 | Photocitral B | 1086 | C10H16O | 152 |
| 319 | a-Thujone | 1089 | C10H16O | 152 |

TABLE 1-continued

List of exemplary terpenes

| No. | chemical name | RI (DB1) | formula | MW |
|---|---|---|---|---|
| 320 | 2,2',5,6-Tetramethylcyclohexanone (Isomer 1) | 1092 | C10H18O | 154 |
| 321 | 1-Oct-3-enyl acetate | 1093 | C10H18O2 | 170 |
| 322 | 4,8-Dimethyl-1,3,7-nonatriene (Isomer 1) | 1096 | C11H18 | 150 |
| 323 | a-Pinene epoxide (Isomer 1) | 1096 | C10H16O | 152 |
| 324 | a-Fenchol | 1099 | C10H18O | 154 |
| 325 | cis-Rose oxide | 1100 | C10H18O | 154 |
| 326 | Isochrysanthenone | 1086 | C10H14O | 150 |
| 327 | b-Thujone | 1103 | C10H16O | 152 |
| 328 | a-Campholenal | 1105 | C10H16O | 152 |
| 329 | 2,2',5,6-Tetramethylcyclohexanone (Isomer 2) | 1106 | C10H18O | 154 |
| 330 | 2-Methyl-5-propionylfuran | 1108 | C8H10O2 | 138 |
| 331 | cis-p-Menth-2-en-1-ol | 1108 | C10H18O | 154 |
| 332 | (Z)-Ocimenoxide | 1115 | C10H16O | 152 |
| 333 | 4,8-Dimethylnona-1,3,7-triene (Isomer 2) | 1115 | C11H18 | 150 |
| 334 | a-Pinene epoxide (Isomer 2) | 1116 | C10H16O | 152 |
| 335 | trans-Rose oxide | 1116 | C10H18O | 154 |
| 336 | Dihydrolinalool | 1118 | C10H20O | 156 |
| 337 | Ipsdienol | 1123 | C10H16O | 152 |
| 338 | Camphor | 1123 | C10H16O | 152 |
| 339 | trans-p-Menth-2-en-1-ol | 1123 | C10H18O | 154 |
| 340 | (E)-Ocimenoxide | 1125 | C10H16O | 152 |
| 341 | p-Mentha-1,5-diene-8-ol | 1127 | C10H16O | 152 |
| 342 | trans-Pinocarveol | 1126 | C10H16O | 152 |
| 343 | cis-Limonene oxide | 1126 | C10H16O | 152 |
| 344 | Photocitral A | 1127 | C10H16O | 152 |
| 345 | o-Cymenene | 1076 | C10H12 | 132 |
| 346 | (E)-Tagetone | 1128 | C10H16O | 152 |
| 347 | (Z)-Tagetone | 1136 | C10H16O | 152 |
| 348 | trans-Limonene oxide | 1130 | C10H16O | 152 |
| 349 | Isopulegol | 1132 | C10H18O | 154 |
| 350 | 1,3-Dimethoxybenzene | 1136 | C8H10O2 | 138 |
| 351 | Menthone | 1136 | C10H18O | 154 |
| 352 | Pinocarvone | 1137 | C10H14O | 150 |
| 353 | b-Terpineol | 1137 | C10H18O | 154 |
| 354 | (E)-Non-2-enal | 1139 | C9H16O | 140 |
| 355 | Isoneral | 1140 | C10H16O | 152 |
| 356 | cis-b-Terpineol | 1141 | C10H18O | 154 |
| 357 | Isoborneol | 1142 | C10H18O | 154 |
| 358 | Karahanaenone | 1142 | C10H16O | 152 |
| 359 | cis- or trans-Linalool oxide (pyranoid) | 1144 | C10H18O2 | 170 |
| 360 | Isomenthone | 1146 | C10H18O | 154 |
| 361 | cis-Chrysanthenol | 1147 | C10H16O | 152 |
| 362 | 2-Hydroxyethyl-4-methylbenzene | 1147 | C9H12O | 136 |
| 363 | 4-Isopropylcyclohexanone | 1148 | C9H16O | 140 |
| 364 | cis- or trans-Linalool oxide (pyranoid) | 1148 | C10H18O2 | 170 |
| 365 | cis-Isopulegone | 1148 | C10H16O | 152 |
| 366 | Methyl phenylacetate | 1148 | C9H10O2 | 150 |
| 367 | cis-Thujol | 1149 | C10H18O | 154 |
| 368 | b-Pinene epoxide | 1149 | C10H16O | 152 |
| 369 | Ethyl benzoate | 1150 | C9H10O2 | 150 |
| 370 | Borneol | 1150 | C10H18O | 154 |
| 371 | Lavandulol | 1150 | C10H18O | 154 |
| 372 | Umbellulone | 1152 | C10H14O | 150 |
| 373 | trans-Chrysanthemol | 1153 | C10H18O | 154 |
| 374 | Neomenthol | 1156 | C10H20O | 156 |
| 375 | Viridene | 1159 | C10H12O | 148 |
| 376 | Isogeranial | 1156 | C10H16O | 152 |
| 377 | cis-Chrysanthemol | 1157 | C10H18O | 154 |
| 378 | Benzoic acid | 1160 | C7H6O2 | 122 |
| 379 | 3-Thujene-10-al | 1158 | C10H14O | 150 |
| 380 | Cryptone | 1160 | C9H14O | 138 |
| 381 | Terpinen-4-ol | 1164 | C10H18O | 154 |
| 382 | b-Pinene epoxide (Isomer) | 1170 | C10H16O | 152 |
| 383 | Nona-2,4-dienal | 1170 | C9H14O | 138 |
| 384 | Methyl salicylate | 1171 | C8H8O3 | 152 |
| 385 | 2-Methyl-2-borneol | 1175 | C11H20O | 168 |
| 386 | 2-Allylphenol | 1174 | C9H10O | 134 |
| 387 | Thujopsa-3-one | 1645 | C15H24O | 220 |
| 388 | 7-Hydroxyhotrienol | 1177 | C10H18O2 | 170 |

TABLE 1-continued

List of exemplary terpenes

| No. | chemical name | RI (DB1) | formula | MW |
|---|---|---|---|---|
| 389 | Myrtenol | 1178 | C10H16O | 152 |
| 390 | cis-Piperitol | 1181 | C10H18O | 154 |
| 391 | Safranal | 1182 | C10H14O | 150 |
| 392 | Estragol (Methylchavicol) | 1175 | C10H12O | 148 |
| 393 | 2-Decanol | 1188 | C10H22O | 158 |
| 394 | g-Terpineol | 1188 | C10H18O | 154 |
| 395 | (E,E)-Nona-2,4-dienal | 1188 | C9H14O | 138 |
| 396 | Methyl a-cyclogeranate | 1190 | C11H18O2 | 182 |
| 397 | trans-Piperitol | 1193 | C10H18O | 154 |
| 398 | Chrysanthenone | 1110 | C10H14O | 150 |
| 399 | Fenchyl acetate | 1205 | C12H20O2 | 196 |
| 400 | Benzylacetone | 1207 | C10H12O | 148 |
| 401 | 2-epi-Thujopsa-3-one | 1634 | C15H24O | 220 |
| 402 | Carvotanacetone | 1220 | C10H16O | 152 |
| 403 | Menthol | 1172 | C10H20O | 156 |
| 404 | Isomenthol | 1176 | C10H20O | 156 |
| 405 | a-Terpinyl acetate | 1335 | C10H16 | 136 |
| 406 | Octyl acetate | 1188 | C10H20O2 | 172 |
| 407 | Dillether | 1170 | C10H16O | 152 |
| 408 | (E)-Ethyl cinnamate | 1439 | C11H12O2 | 176 |
| 409 | b-Ionone | 1468 | C13H20O | 192 |
| 410 | Piperonal | 1294 | C8H6O3 | 150 |
| 411 | Vanilline | 1355 | C8H8O3 | 152 |
| 412 | Coumarin | 1392 | C9H6O2 | 146 |
| 413 | (Z)-2-Hexylcinnamic aldehyde | 1725 | C15H20O | 216 |
| 414 | 1-Phenylethyl acetate | 1166 | C10H12O2 | 164 |
| 415 | (Z)-2-Pentylcinnamaldehyde | 1632 | C14H18O | 202 |
| 416 | Benzyl salicylate | 1847 | C14H12O3 | 228 |
| 417 | Menthofuran | 1150 | C10H14O | 150 |
| 418 | a-Campholenol | 1190 | C10H18O | 154 |
| 419 | Methyl jasmonate | 1611 | C13H20O3 | 224 |
| 420 | Isophytol | 1949 | C20H40O | 296 |
| 421 | Phytol | 2114 | C20H40O | 296 |
| 422 | (E)-Anyl 2-methylbutyrate | 1651 | C14H18O2 | 218 |
| 423 | (E)-4-4Propenylphenol tiglate | 1765 | C14H16O2 | 216 |
| 424 | trans-Epoxypseudoisoeugenyl-2-methylbutyrate | 1871 | C15H20O4 | 264 |
| 425 | (E)-Pseudoisoeugenyl tiglate | 1895 | C15H18O3 | 246 |
| 426 | trans-Epoxypseudoisoeugenol tiglate | 1942 | C15H18O4 | 262 |
| 427 | Dictyotene | 1155 | C11H18 | 150 |
| 428 | Desmarestene | 1168 | C11H14 | 146 |
| 429 | Dictyopterene A | 1099 | C11H18 | 150 |
| 430 | Ectocarpene | 1136 | C11H16 | 148 |
| 431 | (E)-Ectocarpene | 1147 | C11H16 | 148 |
| 432 | cis-Hormosirene | 1152 | C11H16 | 148 |
| 433 | trans-Hormosirene | 1160 | C11H16 | 148 |
| 434 | (Z)-Multifidene | 1040 | C11H16 | 148 |
| 435 | (E)-Multifidene | 1047 | C11H16 | 148 |
| 436 | (E)-Aucantene | 1062 | C11H16 | 148 |
| 437 | (E)-Aucantene | 1077 | C11H16 | 148 |
| 438 | cis-Dihydromultifidene | 1052 | C11H18 | 150 |
| 439 | trans-Dihydromultifidene | 1058 | C11H18 | 150 |
| 440 | Neothujol | 1136 | C10H16O | 152 |
| 441 | (Z)-Methyl cinnamate | 1270 | C10H10O2 | 162 |
| 442 | Isothujol | 1121 | C10H16O | 152 |
| 443 | Neoisothujol | 1132 | C10H16O | 152 |
| 444 | Citronellal | 1129 | C10H18O | 154 |
| 445 | 2-Methyl-2-pentanol | 944 | C6H14O | 102 |
| 446 | 6-Acetoxy-p-mentha-1(7),8-diene (Isomer 1) | 1312 | C12H18O2 | 194 |
| 447 | n-Nonanal | 1076 | C9H18O | 142 |
| 448 | 5,7-Dimethylocta-1,6-diene | 911 | C10H18 | 138 |
| 449 | Dec-9-en-1-ol | 1240 | C10H20O | 156 |
| 450 | Elsholtzia ketone | 1175 | C10H14O2 | 166 |
| 451 | a-Dehydroelsholtzia ketone | 1188 | C10H12O2 | 164 |
| 452 | Dehydroelsholtzia ketone | 1277 | C10H12O2 | 164 |
| 453 | 4-Methyl-3-heptanol | 956 | C8H18O | 130 |
| 454 | 6-Methylhept-5-en-2-ol (Sulcatol) | 981 | C8H16O | 128 |
| 455 | b-Helmiscapene | 1446 | C15H24 | 204 |
| 456 | 2,2-Dimethyl-4-oxocyclohexane-1-carbaldehyde | 1132 | C9H14O2 | 154 |
| 457 | Menth-1-en-9-ol | 1283 | C10H18O | 154 |
| 458 | cis-Dihydrocarvone | 1172 | C10H16O | 152 |
| 459 | trans-Dihydrocarvone | 1177 | C10H16O | 152 |
| 460 | Limonen-10-ol | 1272 | C10H16O | 152 |

TABLE 1-continued

List of exemplary terpenes

| No. | chemical name | RI (DB1) | formula | MW |
|---|---|---|---|---|
| 461 | Tuberolactone | 1437 | C10H14O2 | 166 |
| 462 | trans-Carveol | 1200 | C10H16O | 152 |
| 463 | Dihydrocarveol (Isomer 1) | 1176 | C10H18O | 154 |
| 464 | Dihydrocarveol (Isomer 2) | 1193 | C10H18O | 154 |
| 465 | Dihydrocarveol (Isomer 3) | 1205 | C10H18O | 154 |
| 466 | cis-Carveol | 1210 | C10H16O | 152 |
| 467 | 4-Methoxyphenylacetone | 1343 | C10H12O2 | 164 |
| 468 | 4-Methoxypropiophenone | 1415 | C10H12O2 | 164 |
| 469 | Grandisol | 1200 | C10H18O | 154 |
| 470 | Hotrienol | 1083 | C10H16O | 152 |
| 471 | Isopinocampheol | 1168 | C10H16O | 152 |
| 472 | (E)-Pseudoisoeugenyl-2-methyl butyrate | 1823 | C15H20O3 | 248 |
| 473 | Falcarinone | 1990 | C17H22O | 242 |
| 474 | Ethyl salicylate | 1245 | C9H10O3 | 166 |
| 475 | 1,2-Dihydro-1,1,6-trimethyl-naphthalene | 1339 | C13H16 | 172 |
| 476 | g-Hexanolide | 1006 | C6H10O2 | 114 |
| 477 | g-Heptanolide | 1103 | C7H12O2 | 128 |
| 478 | g-Octanolide | 1208 | C8H14O2 | 142 |
| 479 | g-Nonanolide | 1318 | C9H16O2 | 156 |
| 480 | g-Decanolide | 1433 | C10H18O2 | 170 |
| 481 | g-Undecanolide | 1547 | C11H20O2 | 184 |
| 482 | g-Dodecanolide | 1656 | C12H22O2 | 198 |
| 483 | g-Tetradecanolide | 1866 | C14H26O2 | 226 |
| 484 | d-Nonanolide | 1348 | C9H16O2 | 156 |
| 485 | d-Octanolide | 1240 | C8H14O2 | 142 |
| 486 | d-Heptanolide | 1156 | C7H12O2 | 128 |
| 487 | d-Decanolide | 1461 | C10H18O2 | 170 |
| 488 | (E)-a-Damascone | 1375 | C13H20O | 192 |
| 489 | 4-Methyl-3-heptanone | 918 | C8H16O | 128 |
| 490 | a-Ionone | 1409 | C13H20O | 192 |
| 491 | p-Methylacetophenone | 1156 | C9H10O | 134 |
| 492 | b-Cyclocitral | 1195 | C10H16O | 152 |
| 493 | cis-a-Irone | 1520 | C14H22O | 206 |
| 494 | cis-g-Irone | 1525 | C14H22O | 206 |
| 495 | Dodecanal | 1389 | C12H24O | 184 |
| 496 | Methyl linolenate | 2102 | C19H32O2 | 292 |
| 497 | Geranylacetone | 1430 | C13H22O | 194 |
| 498 | trans-Isolimonene | 975 | C10H16 | 136 |
| 499 | cis-Myrtanol | 1238 | C10H18O | 154 |
| 500 | n-Octanal | 981 | C8H16O | 128 |
| 501 | p-Menth-1-ene | 1017 | C15H18 | 198 |
| 502 | (E)-Jasmone | 1356 | C11H16O | 164 |
| 503 | trans-Myrtanol | 1240 | C10H18O | 154 |
| 504 | allo-Ocimene | 1113 | C10H16 | 136 |
| 505 | (4E,6Z)-allo-Ocimene | 1126 | C10H16 | 136 |
| 506 | Dodecanol | 1472 | C12H26O | 186 |
| 507 | 6-Acetoxy-p-menta-1,8-diene | 1341 | C12H18O2 | 194 |
| 508 | b-Citronellene | 943 | C15H18 | 198 |
| 509 | n-Nonanol | 1149 | C9H20O | 144 |
| 510 | trans-Sabinol | 1120 | C10H16O | 152 |
| 511 | 3,5-Dimethoxytoluene | 1231 | C9H12O2 | 152 |
| 512 | Phantolide | 1712 | C17H24O | 244 |
| 513 | Perilla alcohol | 1280 | C10H16O | 152 |
| 514 | b-Phellandrene | 1023 | C10H16 | 136 |
| 515 | b-Phenylethanol | 1085 | C8H10O | 122 |
| 516 | Citronellol | 1213 | C10H20O | 156 |
| 517 | Methyleugenol | 1369 | C11H14O2 | 178 |
| 518 | 2-Nonanone | 1074 | C9H18O | 142 |
| 519 | 2-Decanone | 1176 | C10H20O | 156 |
| 520 | 2-Dodecanone | 1381 | C12H24O | 184 |
| 521 | 4-Isopropylcyclohexanol (Isomer 2) | 1130 | C9H18O | 142 |
| 522 | Moskachane B | 1794 | C13H16O3 | 220 |
| 523 | Moskachane D | 2001 | C15H20O3 | 248 |
| 524 | cis-Verbenol | 1132 | C10H16O | 152 |
| 525 | (Z)-Salvene | 849 | C9H16 | 124 |
| 526 | (E)-Salvene | 859 | C9H16 | 124 |
| 527 | Santolinatriene | 909 | C10H16 | 136 |
| 528 | a-Thujene | 932 | C10H16 | 136 |
| 529 | Sabinene | 973 | C10H16 | 136 |
| 530 | a-Terpinene | 1013 | C10H16 | 136 |
| 531 | trans-Verbenol | 1136 | C10H14O | 150 |
| 532 | Verbenone | 1183 | C10H14O | 150 |
| 533 | Z-Cinnamaldehyde | 1185 | C9H8O | 132 |

TABLE 1-continued

List of exemplary terpenes

| No. | chemical name | RI (DB1) | formula | MW |
|---|---|---|---|---|
| 534 | 3-Phenylpropanol | 1201 | C9H12O | 136 |
| 535 | (E)-Cinnamyl alcohol | 1275 | C9H10O | 134 |
| 536 | b-Irone | 1566 | C14H22O | 206 |
| 537 | Benzyl acetate | 1134 | C9H10O2 | 150 |
| 538 | Indole | 1257 | C8H7N | 117 |
| 539 | d-Jasmolactone | 1450 | C10H16O2 | 168 |
| 540 | N-Acetyl methyl anthranilate | 1565 | C10H11O3N | 193 |
| 541 | Benzyl benzoate | 1730 | C14H12O2 | 212 |
| 542 | 6-Methylhept-5-en-2-one | 978 | C8H14O | 126 |
| 543 | Rosefuran | 1091 | C10H14O | 150 |
| 544 | Rosefuran epoxide | 1161 | C10H14O2 | 166 |
| 545 | b-Pinene | 978 | C10H16 | 136 |
| 546 | Myrcene | 987 | C10H16 | 136 |
| 547 | Oct-3-en-1-ol (Isomer 2) | 1049 | C8H16O | 128 |
| 548 | 6-Acetoxy-p-mentha-1(7),8-diene (Isomer 2) | 1343 | C12H18O2 | 194 |
| 549 | (E)-4-Propenylphenol angelate | 1751 | C14H16O2 | 216 |
| 550 | cis-Epoxypseudoisoeugenyl-2-methyl butyrate | 1870 | C15H20O4 | 264 |
| 551 | Myrtenal | 1172 | C10H14O | 150 |
| 552 | (E)-Ocimenone | 1219 | C10H14O | 150 |
| 553 | (Z)-Ocimenone | 1209 | C10H14O | 150 |
| 554 | Isomenthyl acetate | 1298 | C12H22O2 | 198 |
| 555 | Thymoquinone | 1215 | C10H12O2 | 164 |
| 556 | Cymen-9-ol | 1157 | C10H14O | 150 |
| 557 | 8,9-Dehydrothymol | 1190 | C10H12O | 148 |
| 558 | (Z)-Methyl p-hydroxycinnamate | 1603 | C10H10O3 | 178 |
| 559 | b-Thujaplicine | 1449 | C10H12O2 | 164 |
| 560 | n-Undecane | 1100 | C11H24 | 156 |
| 561 | n-Nonane | 906 | C9H20 | 128 |
| 562 | Pinocamphone | 1139 | C10H16O | 152 |
| 563 | Isopinocamphone | 1151 | C10H16O | 152 |
| 564 | Methyl 2-methylbutyrate | 954 | C6H12O2 | 116 |
| 565 | 6-Methylhept-5-enal | 985 | C8H14O | 126 |
| 566 | Furomyrcenol | 1256 | C10H14O2 | 166 |
| 567 | a-Ionone epoxide (Isomer 1) | 1516 | C13H20O2 | 208 |
| 568 | o-Cresol | 1037 | C7H8O | 108 |
| 569 | (E)-2-Hexenal | 832 | C6H10O | 98 |
| 570 | Ethyl 2-methylbutyrate | 843 | C7H14O2 | 130 |
| 571 | p-Mentha-2,4(8)-diene | 1077 | C10H16 | 136 |
| 572 | p-Mentha-1,3,8-triene | 1101 | C10H16 | 136 |
| 573 | Neroloxide | 1137 | C10H16O | 152 |
| 574 | Neoisopulegol | 1150 | C10H18O | 154 |
| 575 | (E,E)-Nona-3,6-dien-1-ol | 1145 | C9H16O | 140 |
| 576 | n-Pentylbenzene | 1150 | C11H16 | 148 |
| 577 | (Z)-Ethyl oct-5-enoate | 1174 | C10H18O2 | 170 |
| 578 | a-Terpineol | 1176 | C10H18O | 154 |
| 579 | 2a-Hydroxy-1,8-cineol | 1196 | C10H18O2 | 170 |
| 580 | cis-Pulegol | 1215 | C10H18O | 154 |
| 581 | 3b-Hydroxy-1,8-cineol | 1229 | C10H18O2 | 170 |
| 582 | Linalyl acetate | 1239 | C12H20O2 | 196 |
| 583 | Isopiperitenone | 1240 | C10H14O | 150 |
| 584 | Piperitenone | 1318 | C10H14O | 150 |
| 585 | Piperitenone oxide | 1335 | C10H14O2 | 166 |
| 586 | Geranyl acetate | 1362 | C12H20O2 | 196 |
| 587 | 2-Methylbutyl benzoate | 1419 | C12H16O2 | 192 |
| 588 | Myristicine | 1489 | C11H12O3 | 192 |
| 589 | Acetophenone | 1036 | C8H8O | 120 |
| 590 | Dihydrotagetone | 1047 | C10H18O | 154 |
| 591 | p-Cymenene | 1075 | C10H12 | 132 |
| 592 | Piperiton epoxid | 1232 | C10H16O2 | 168 |
| 593 | Nepetalacton (Isomer 2) | 1360 | C10H14O2 | 166 |
| 594 | 3,4-Dimethyl-5-pentyl-5H-furan-2-one | 1481 | C11H18O2 | 182 |
| 595 | Methyl p-methoxybenzoate | 1338 | C9H10O3 | 166 |
| 596 | (E)-o-Methoxycinnamyl alcohol | 1488 | C10H12O2 | 164 |
| 597 | (E)-m-Methoxycinnamyl alcohol | 1511 | C10H12O2 | 164 |
| 598 | (E)-p-Methoxycinnamyl alcohol | 1523 | C10H12O2 | 164 |
| 599 | Perillene | 1090 | C10H14O | 150 |
| 600 | Methyl anthranilate | 1308 | C8H9O2N | 151 |
| 601 | 1-(3-Methoxyphenyl)-2-phenylethane | 1735 | C15H16O | 212 |
| 602 | 1-Phenyl-2-(3,5-dimethoxyphenyl)-ethane | 1962 | C16H18O2 | 242 |

TABLE 1-continued

List of exemplary terpenes

| No. | chemical name | RI (DB1) | formula | MW |
|---|---|---|---|---|
| 603 | 1-(3-Methoxyphenyl)-2-(4-methoxyphenyl)-ethane | 1988 | C16H18O2 | 242 |
| 604 | Neryl isobutyrate | 1468 | C14H24O2 | 224 |
| 605 | Zingiberenol | 1596 | C14H24O | 208 |
| 606 | Encecalin | 1813 | C14H16O3 | 232 |
| 607 | Ethyl p-methoxybenzoate | 1415 | C10H12O3 | 180 |
| 608 | Albanone | 1389 | C12H18O | 178 |
| 609 | 7,10-Anhydro-11,12-dihydrochiloscypholone | 1449 | C15H24O | 220 |
| 610 | 1(11)-Africanen-8-ol | 1486 | C15H24O | 220 |
| 611 | Atractylone | 1497 | C15H20O | 216 |
| 612 | Conocephalenol | 1497 | C15H26O | 222 |
| 613 | Cubebol | 1514 | C15H26O | 222 |
| 614 | Photosantalol | 1511 | C15H24O | 220 |
| 615 | Cyperene epoxide | 1524 | C15H24O | 220 |
| 616 | Isoafricanol | 1529 | C15H26O | 222 |
| 617 | cis-Cadina-4,6-dien-11-ol | 1531 | C15H24O | 220 |
| 618 | Elema-1,3-dien-7-ol | 1531 | C15H24O | 220 |
| 619 | Tamariscol | 1535 | C15H26O | 222 |
| 620 | Pacifigorgiol | 1539 | C15H26O | 222 |
| 621 | (E,E)-Methyl 10-oxofarnesoate | 1896 | C16H26O3 | 266 |
| 622 | b-Caryophyllene oxide | 1546 | C15H24O | 220 |
| 623 | Africanone | 1547 | C15H22O | 218 |
| 624 | 1,8-Oxidocadin-4-ene | 1551 | C15H24O | 220 |
| 625 | 4bH,5aH-cis-Eudesm-6-en-11-ol | 1555 | C15H26O | 222 |
| 626 | Dactylol | 1556 | C15H26O | 222 |
| 627 | cis-Sesquisabinenhydrate | 1558 | C15H26O | 222 |
| 628 | 11,12-Dihydrochiloscyphone | 1558 | C15H24O | 220 |
| 629 | Aromadendran-5-ol | 1562 | C15H26O | 222 |
| 630 | Oxidohimachalene | 1557 | C15H22O | 218 |
| 631 | (+)-Marsupellol | 1564 | C15H24O | 220 |
| 632 | b-Himachalol | 1638 | C15H26O | 222 |
| 633 | Maaliol | 1565 | C15H26O | 222 |
| 634 | Deoxopinguisone | 1563 | C15H22O | 218 |
| 635 | Palustrol | 1569 | C15H26O | 222 |
| 636 | 4a-Hydroxygermacra-1(10),5-diene | 1571 | C15H26O | 222 |
| 637 | Spathulenol | 1572 | C15H24O | 220 |
| 638 | 4-Dehydroviridiflorol | 1572 | C15H24O | 220 |
| 639 | Caryophyllene oxide | 1578 | C15H24O | 220 |
| 640 | 7-Acetoxyelema-1,3,8-triene | 1584 | C17H26O2 | 262 |
| 641 | Globulol | 1589 | C15H26O | 222 |
| 642 | Cubeban-11-ol | 1591 | C15H26O | 222 |
| 643 | Salvial-4(14)-en-1-one | 1592 | C15H24O | 220 |
| 644 | Bisabola-2,10-diene 1,9-oxide | 1592 | C15H24O | 220 |
| 645 | b-Oplopenone | 1595 | C15H24O | 220 |
| 646 | Longiborneol | 1597 | C15H26O | 222 |
| 647 | Rosifoliol | 1599 | C15H26O | 222 |
| 648 | Ledol | 1600 | C15H26O | 222 |
| 649 | 2-Methyl-1-(octahydro-7,7a-dimethyl-1H-inden-1-yl)-propan-1-one | 1601 | C15H26O | 222 |
| 650 | Eudesm-4-en-7-ol | 1604 | C15H26O | 222 |
| 651 | Rearrangement product from Grimaldone | 1608 | C15H22O | 218 |
| 652 | Maalian-5-ol | 1607 | C15H26O | 222 |
| 653 | 10-epi-g-Eudesmol | 1609 | C15H26O | 222 |
| 654 | ar-Curcumen-7-ol | 1610 | C15H22O | 218 |
| 655 | Amorpha-4,7-dien-11-ol | 1610 | C15H24O | 220 |
| 656 | 5-Guaiene-11-ol | 1619 | C15H26O | 222 |
| 657 | g-Eudesmol | 1618 | C15H26O | 222 |
| 658 | Alismol | 1619 | C15H24O | 220 |
| 659 | Gymnomitrone | 1620 | C15H22O | 218 |
| 660 | Isospathulenol | 1625 | C15H24O | 220 |
| 661 | Isogymnomitrol | 1625 | C15H24O | 220 |
| 662 | Furanoeudesm-1,3-diene | 1630 | C15H18O | 214 |
| 663 | Amorpha-4-en-7-ol | 1629 | C15H26O | 222 |
| 664 | Eudesm-3,11-dien-5-ol | 1632 | C15H24O | 220 |
| 665 | Hinesol | 1632 | C15H26O | 222 |
| 666 | T-Muurolol | 1633 | C15H26O | 222 |
| 667 | (E,E)-Germacradiene-11-ol | 1633 | C15H26O | 222 |
| 668 | T-Cadinol | 1633 | C15H26O | 222 |
| 669 | Gymnomitr-3(15)-en-4-one | 1635 | C15H22O | 218 |
| 670 | 1(10)-Spirovetivene-7b-ol | 1636 | C15H26O | 222 |
| 671 | Muurola-3,7(11)-dien-1-ol | 1637 | C15H24O | 220 |
| 672 | 6-Himachalen-9b-ol | 1638 | C15H26O | 222 |

TABLE 1-continued

List of exemplary terpenes

| No. | chemical name | RI (DB1) | formula | MW |
|---|---|---|---|---|
| 673 | Gymnomitran-4-one | 1639 | C15H24O | 220 |
| 674 | b-Eudesmol | 1641 | C15H26O | 222 |
| 675 | Furanoeremophilene | 1642 | C15H22O | 218 |
| 676 | 2-Himachalen-7b-ol | 1642 | C15H26O | 222 |
| 677 | a-Cadinol | 1643 | C15H26O | 222 |
| 678 | Eudesm-4(15)-en-7-ol | 1643 | C15H24O | 220 |
| 679 | 2-Methyl-1-(octahydro-7,7a-dimethyl-1H-inden-1-yl)-propan-1-ol | 1645 | C15H28O | 224 |
| 680 | Eudesm-11-en-4a-ol | 1649 | C15H26O | 222 |
| 681 | 1(10)-Valencen-7b-ol | 1646 | C15H26O | 222 |
| 682 | Valerianol | 1647 | C15H26O | 222 |
| 683 | Eudesm-3-en-7-ol | 1650 | C15H26O | 222 |
| 684 | 10-epi-trans-Dracunculifoliol | 1591 | C15H26O | 222 |
| 685 | 7-epi-a-Eudesmol | 1653 | C15H26O | 222 |
| 686 | Acorenol B | 1654 | C15H26O | 222 |
| 687 | Bisabolol oxide B | 1654 | C15H26O2 | 238 |
| 688 | Aromadendran-12-ol | 1654 | C15H24O | 220 |
| 689 | Grimaldone | 1656 | C15H22O | 218 |
| 690 | Gymnomitrol | 1657 | C15H24O | 220 |
| 691 | Eudesm-4(15)-en-6-ol | 1656 | C15H26O | 222 |
| 692 | Saccogynol | 1660 | C15H22O | 218 |
| 693 | Valeranone | 1664 | C15H26O | 222 |
| 694 | 4-epi-Acorenone | 1664 | C15H24O | 220 |
| 695 | Gymnomitr-3(15)-en-4a-ol | 1665 | C15H24O | 220 |
| 696 | Acorenol | 1667 | C15H26O | 222 |
| 697 | epi-Cyclosantalal | 1668 | C15H24O | 220 |
| 698 | (Z)-g-Atlantone | 1669 | C15H22O | 218 |
| 699 | a-Alasken-6-ol | 1674 | C15H24O | 220 |
| 700 | Bisabolone oxide A | 1675 | C15H24O2 | 236 |
| 701 | Amorpha-4,7(11)-dien-8-one | 1679 | C15H22O | 218 |
| 702 | Amorpha-4,9-dien-2-ol | 1679 | C15H24O | 220 |
| 703 | Amorpha-4,9-dien-14-al | 1685 | C15H22O | 218 |
| 704 | Eudesm-3-en-6-ol | 1679 | C15H26O | 222 |
| 705 | Khusiol | 1680 | C15H26O | 222 |
| 706 | (E)-g-Atlantone | 1681 | C15H22O | 218 |
| 707 | Acorenone | 1681 | C15H24O | 220 |
| 708 | Cadina-1(10),4-dien-8a-ol | 1682 | C15H24O | 220 |
| 709 | Bicyclogermacren-14-al | 1684 | C15H22O | 218 |
| 710 | Cyperotundone | 1684 | C15H22O | 218 |
| 711 | (Z)-a-Atlantone | 1689 | C15H22O | 218 |
| 712 | Lanceol oxide | 1695 | C15H24O | 220 |
| 713 | Farnesol (Isomer 1) | 1694 | C15H26O | 222 |
| 714 | 6a-Hydroxygermacra-1(10),4-diene | 1687 | C15H26O | 222 |
| 715 | Acora-7(11),9-dien-2-one | 1706 | C15H22O | 218 |
| 716 | Valerenal | 1706 | C15H22O | 218 |
| 717 | a-Herbertenol | 1711 | C15H22O | 218 |
| 718 | Dihydrochiloscypholone | 1711 | C15H26O2 | 238 |
| 719 | Italicen-4-one | 1717 | C15H22O | 218 |
| 720 | Farnesol (Isomer 2) | 1718 | C15H26O | 222 |
| 721 | 10-epi-1,8-Oxidocadina-4-ene | 1539 | C15H24O | 220 |
| 722 | Neopetasone | 1733 | C15H22O | 218 |
| 723 | 7,14-Anhydroamorpha-4,9-diene | 1733 | C15H22O | 218 |
| 724 | Lepidozenal | 1744 | C15H22O | 218 |
| 725 | 7-Acetoxyelema-1,3-dien-8-ol | 1793 | C17H28O3 | 280 |
| 726 | Naviculol | 1734 | C15H26O | 222 |
| 727 | Bisabolol oxide A | 1740 | C15H26O2 | 238 |
| 728 | a-Cyperone | 1741 | C15H22O | 218 |
| 729 | Cyclocolorenone | 1745 | C15H22O | 218 |
| 730 | Gymnomitrol acetate | 1751 | C17H26O2 | 262 |
| 731 | b-Herbertenol | 1751 | C15H22O | 218 |
| 732 | (E)-a-Atlantone | 1754 | C15H22O | 218 |
| 733 | (Z)-Lanceol | 1755 | C15H24O | 220 |
| 734 | Cuparophenol | 1763 | C15H22O | 218 |
| 735 | Cedryl acetate | 1764 | C17H28O2 | 264 |
| 736 | 14-Oxocalamenene | 1768 | C15H20O | 216 |
| 737 | Isovalencenol | 1779 | C15H24O | 220 |
| 738 | Drimenol | 1750 | C15H26O | 222 |
| 739 | cis-5-Hydroxycalamenene | 1790 | C15H22O | 218 |
| 740 | Khusienol acetate | 1789 | C17H26O2 | 262 |
| 741 | Fukinanolide | 1798 | C15H22O2 | 234 |
| 742 | Bisabola-2,7(Z),10(Z)-triene-13-ol | 1806 | C15H24O | 220 |
| 743 | Cyperadione | 1820 | C15H24O2 | 236 |
| 744 | cis-Spiroether | 1850 | C13H12O2 | 200 |
| 745 | trans-Spiroether | 1853 | C13H12O2 | 200 |

TABLE 1-continued

List of exemplary terpenes

| No. | chemical name | RI (DB1) | formula | MW |
|---|---|---|---|---|
| 746 | trans-4,8a-Dimethyl-4a,5-epoxydecaline | 1350 | C12H20O | 180 |
| 747 | Peculiaroxide | 1416 | C15H26O | 222 |
| 748 | Furanoelemene | 1485 | C15H20O | 216 |
| 749 | Guaioxide | 1487 | C15H26O | 222 |
| 750 | Elemol | 1541 | C15H26O | 222 |
| 751 | Lemnalol | 1579 | C15H24O | 220 |
| 752 | Fokienol | 1582 | C15H24O | 220 |
| 753 | Thujopsane-2b-ol | 1593 | C15H26O | 222 |
| 754 | a-Alasken-8-ol | 1600 | C15H24O | 220 |
| 755 | 6-epi-Cubenol | 1602 | C15H26O | 222 |
| 756 | Widdrol | 1601 | C15H26O | 222 |
| 757 | Marsupellone | 1604 | C15H22O | 218 |
| 758 | Axinyssene | 1860 | C20H32 | 272 |
| 759 | Selina-1,3,7(11)-trien-8-one | 1616 | C15H20O | 216 |
| 760 | Myliol | 1617 | C15H22O | 218 |
| 761 | a-Acorenol | 1623 | C15H26O | 222 |
| 762 | Furanogermacrene | 1624 | C15H20O | 216 |
| 763 | Acora-3,7(11)-dien-6-ol | 1626 | C15H24O | 220 |
| 764 | b-Acorenol | 1626 | C15H26O | 222 |
| 765 | a-Alaskene-8-ol | 1632 | C15H24O | 220 |
| 766 | Microbiotol | 1632 | C15H26O | 222 |
| 767 | Isopinguisanine | 1638 | C15H20O2 | 232 |
| 768 | Gymnomitr-3(15)-en-4b-ol | 1653 | C15H24O | 220 |
| 769 | a-Eudesmol | 1653 | C15H26O | 222 |
| 770 | Isorotundenol | 1659 | C15H26O | 222 |
| 771 | Bulnesol | 1665 | C15H26O | 222 |
| 772 | Bicyclohumulenone | 1668 | C15H24O | 220 |
| 773 | Selina-4(15),11-dien-8-ol | 1670 | C15H24O | 220 |
| 774 | Smyrnicordifuran | 1673 | C15H18O2 | 230 |
| 775 | b-Sinensal | 1675 | C15H22O | 218 |
| 776 | Isocyperol | 1676 | C15H24O | 220 |
| 777 | a-Cuparenone | 1681 | C15H20O | 216 |
| 778 | Cyperol | 1681 | C15H24O | 220 |
| 779 | Gymnomitr-3-en-15-ol | 1688 | C15H24O | 220 |
| 780 | Pinguisanine | 1706 | C15H20O2 | 232 |
| 781 | Acora-3,7(11)-dien-8-one | 1709 | C15H22O | 218 |
| 782 | Vetiselinol | 1709 | C15H24O | 220 |
| 783 | 10,11-Dihydro-a-cuparenone | 1712 | C15H22O | 218 |
| 784 | Oxidoselina-1,3,7(11)-trien-8-one | 1725 | C15H20O2 | 232 |
| 785 | a-Sinensal | 1726 | C15H22O | 218 |
| 786 | Plagiochilide | 1729 | C15H20O2 | 232 |
| 787 | (E,E)-Methyl 10,11-epoxyfarnesoate | 1875 | C16H26O3 | 266 |
| 788 | Eudesma-3,11-dien-2-one | 1776 | C15H22O | 218 |
| 789 | Zizaenic acid | 1791 | C15H22O2 | 234 |
| 790 | Acutifolene B | 1806 | C15H20O3 | 248 |
| 791 | a-Vetivone | 1821 | C15H22O | 218 |
| 792 | (E,E)-Farnesylacetate | 1822 | C17H28O2 | 264 |
| 793 | Acutifolene A | 1833 | C16H22O3 | 262 |
| 794 | Furanoeremophilone | 1855 | C15H20O2 | 232 |
| 795 | 2-Acetoxyfuranoelemene | 1876 | C17H22O3 | 274 |
| 796 | Guaia-3,10(14)-dien-6,12-olide | 1938 | C15H20O2 | 232 |
| 797 | Guaia-3,7(11),10(14)-trien-6,12-olide | 1950 | C15H18O2 | 230 |
| 798 | 1b-Acetoxyfurano-4(15)-eudesmene | 1964 | C17H22O3 | 274 |
| 799 | 1b-Acetoxyfurano-3-eudesmene | 1978 | C17H22O3 | 274 |
| 800 | Maalioxide | 1508 | C15H26O | 222 |
| 801 | Kessane | 1533 | C15H26O | 222 |
| 802 | Humulene epoxide 3 | 1626 | C15H24O | 220 |
| 803 | 8-Hydroxybicyclogermacrene | 1661 | C15H24O | 220 |
| 804 | Lactarovioline | 2068 | C15H14O | 210 |
| 805 | 5-epi-Pinguisenol | 1764 | C15H26O | 222 |
| 806 | b-Santalol acetate | 1800 | C17H26O2 | 262 |
| 807 | Bisacumol (Isomer 1) | 1596 | C15H22O | 218 |
| 808 | Bisacumol (Isomer 2) | 1619 | C15H22O | 218 |
| 809 | Bisabola-1,3(15),10-trien-9-ol (Isomer 1) | 1666 | C15H24O | 220 |
| 810 | Bisabola-1,3(15),10-trien-9-ol (Isomer 2) | 1678 | C15H24O | 220 |
| 811 | trans-Sesquisabinen hydrate | 1564 | C15H26O | 222 |
| 812 | 1bH-Presilphiperfolane-9a-ol | 1510 | C15H26O | 222 |
| 813 | 1aH-Presilphiperfolan-9b-ol | 1499 | C15H26O | 222 |
| 814 | Presilphiperfolane-9a-ol | 1519 | C15H26O | 222 |
| 815 | ar-Curcumen-15-al | 1681 | C15H20O | 216 |
| 816 | Sesquicineol | 1507 | C15H26O | 222 |

TABLE 1-continued

List of exemplary terpenes

| No. | chemical name | RI (DB1) | formula | MW |
|---|---|---|---|---|
| 817 | Italicen-13-al | 1671 | C15H22O | 218 |
| 818 | a-Copaen-8-ol | 1551 | C15H24O | 220 |
| 819 | Khusimol | 1720 | C15H24O | 220 |
| 820 | Zizanol | 1656 | C15H24O | 220 |
| 821 | Oxidocadalene | 1644 | C15H18O | 214 |
| 822 | Eremoligenol | 1614 | C15H26O | 222 |
| 823 | Isohumbertiol D (Isomer 2) | 1519 | C15H24O | 220 |
| 824 | Isohumbertiol D (Isomer 1) | 1490 | C15H24O | 220 |
| 825 | Brachylaenalone B | 1824 | C15H20O2 | 232 |
| 826 | Khusien-12-al | 1580 | C15H22O | 218 |
| 827 | Eudesma-4(15),7(11)-dien-8-one | 1713 | C15H22O | 218 |
| 828 | Elemenone | 1589 | C15H22O | 218 |
| 829 | b-Cedrene epoxide | 1610 | C15H24O | 220 |
| 830 | b-Panasinsen-5a-ol | 1621 | C15H24O | 220 |
| 831 | Eudesm-7(11)-en-4a-ol | 1676 | C15H26O | 222 |
| 832 | 5,8-Cyclocaryophyllan-4-ol | 1514 | C15H26O | 222 |
| 833 | Khusol | 1769 | C15H24O | 220 |
| 834 | cis-10-Hydroxycalamenene | 1643 | C15H22O | 218 |
| 835 | trans-10-Hydroxycalamenene | 1635 | C15H22O | 218 |
| 836 | Bryopterine A | 1735 | C16H20O3 | 260 |
| 837 | Isoitalicene epoxide | 1501 | C15H24O | 220 |
| 838 | Italicene epoxide | 1535 | C15H24O | 220 |
| 839 | a-Agarofuran | 1537 | C15H24O | 220 |
| 840 | Longipin-3-en-10-ol | 1560 | C15H24O | 220 |
| 841 | Dihydrosesquicineol | 1467 | C15H28O | 224 |
| 842 | Dehydrosesquicineol | 1466 | C15H24O | 220 |
| 843 | Longicamphenilone | 1549 | C14H22O | 206 |
| 844 | Longicamphenilol | 1578 | C14H24O | 208 |
| 845 | Isobutyl angelate | 1027 | C9H16O2 | 156 |
| 846 | Isoacorone | 1774 | C15H24O2 | 236 |
| 847 | Dehydrosesquicineyl-12-ol | 1707 | C15H24O2 | 236 |
| 848 | Dihydrobryopterine A | 1763 | C16H22O3 | 262 |
| 849 | (E)-Nuciferal | 1705 | C15H20O | 216 |
| 850 | (Z)-Nuciferal | 1695 | C15H20O | 216 |
| 851 | Pinguisanene | 1544 | C15H20O | 216 |
| 852 | (E)-Methyl 10-hydroxy-3,7,11-trimethyldodeca-2,6,11-trienoate | 1930 | C16H26O3 | 266 |
| 853 | Dihydroagarofuran | 1500 | C15H26O | 222 |
| 854 | Isolongifolol | 1717 | C15H26O | 222 |
| 855 | (Z)-Nerolidol | 1522 | C15H26O | 222 |
| 856 | (E)-Nerolidol | 1553 | C15H26O | 222 |
| 857 | a-Cedrene oxide | 1571 | C15H24O | 220 |
| 858 | Caryolan-1-ol | 1567 | C15H26O | 222 |
| 859 | Thujopsan-2a-ol | 1584 | C15H26O | 222 |
| 860 | Curcerenone | 1588 | C15H18O2 | 230 |
| 861 | a-Guaiol | 1593 | C15H26O | 222 |
| 862 | Viridiflorol | 1592 | C15H26O | 222 |
| 863 | Epicurcerenone | 1593 | C15H18O2 | 230 |
| 864 | Carotol | 1594 | C15H26O | 222 |
| 865 | Cedrol | 1603 | C15H26O | 222 |
| 866 | 12-epi-Cedrol | 1620 | C15H26O | 222 |
| 867 | 1-epi-Cubenol | 1623 | C15H26O | 222 |
| 868 | ar-Turmerone | 1643 | C15H20O | 216 |
| 869 | 3(15)-Cedren-4-ol | 1647 | C15H24O | 220 |
| 870 | a-Turmerone | 1649 | C15H22O | 218 |
| 871 | Patchouli alcohol | 1661 | C15H26O | 222 |
| 872 | (Z)-a-Santalol | 1669 | C14H22O | 206 |
| 873 | a-Bisabolol | 1673 | C15H26O | 222 |
| 874 | Acorenone B | 1679 | C15H24O | 220 |
| 875 | Germacrone | 1684 | C15H22O | 218 |
| 876 | Curcuphenol | 1693 | C15H22O | 218 |
| 877 | 2-Butylfuran | 869 | C8H12O | 124 |
| 878 | Pinguisone | 1705 | C15H20O2 | 232 |
| 879 | (Z)-b-Santalol | 1702 | C15H24O | 220 |
| 880 | Xanthorhizol | 1732 | C15H22O | 218 |
| 881 | cis-2-Hydroxycalamenene | 1762 | C15H22O | 218 |
| 882 | Furanogermenone | 1770 | C15H20O2 | 232 |
| 883 | Alantolactone | 1873 | C15H20O2 | 232 |
| 884 | Dihydroisoalantolactone | 1875 | C15H22O2 | 234 |
| 885 | Frullanolide | 1900 | C15H20O2 | 232 |
| 886 | Isoalantolactone | 1912 | C15H20O2 | 232 |
| 887 | ent-Diplophyllolide | 1937 | C15H20O2 | 232 |
| 888 | Guaia-6,9-dien-4b-ol | 1565 | C15H24O | 220 |
| 889 | Guaia-6,10(14)-diene-4b-ol | 1610 | C15H24O | 220 |
| 890 | Cedrenone | 1722 | C15H22O | 218 |

TABLE 1-continued

List of exemplary terpenes

| No. | chemical name | RI (DB1) | formula | MW |
|---|---|---|---|---|
| 891 | 8bH-Cedran-9-one | 1608 | C15H24O | 220 |
| 892 | Deodarone | 1676 | C15H24O2 | 236 |
| 893 | Pogostol | 1647 | C15H26O | 222 |
| 894 | Dihydro-ar-turmerone | 1570 | C15H22O | 218 |
| 895 | Norpatchoulenol | 1551 | C14H22O | 206 |
| 896 | Caryophyllan-2,6-a-oxide | 1412 | C15H26O | 222 |
| 897 | Caryophyllen-2,6-b-oxide | 1422 | C15H26O | 222 |
| 898 | b-Atlantol (Isomer 1) | 1436 | C15H24O | 220 |
| 899 | b-Atlantol (Isomer 2) | 1443 | C15H24O | 220 |
| 900 | 1,11-Oxidocalamenene | 1474 | C15H20O | 216 |
| 901 | Furopelargone A | 1517 | C15H22O2 | 234 |
| 902 | Isohumbertiol B | 1522 | C15H24O | 220 |
| 903 | Silphiperfolene-5-ol | 1549 | C15H24O | 220 |
| 904 | b-Funebrene epoxide | 1591 | C15H24O | 220 |
| 905 | b-Himachalene epoxide | 1594 | C15H24O | 220 |
| 906 | Copaborneol | 1595 | C15H26O | 222 |
| 907 | 10-epi-Italicen-4-one | 1615 | C15H22O | 218 |
| 908 | ar-Bisabolol | 1619 | C15H22O | 218 |
| 909 | allo-Aromadendrene epoxide | 1623 | C15H24O | 220 |
| 910 | Amorph-4-en-10a-ol | 1634 | C15H26O | 222 |
| 911 | alio-Himachalol | 1648 | C15H26O | 222 |
| 912 | Farnesal (Isomer 1) | 1655 | C15H24O | 220 |
| 913 | b-Sesquiphellandrone | 1677 | C15H22O | 218 |
| 914 | Aromadendran-14-ol | 1679 | C15H26O | 222 |
| 915 | Farnesal (Isomer 2) | 1683 | C15H24O | 220 |
| 916 | Farnesal (Isomer 3) | 1707 | C15H24O | 220 |
| 917 | Longifolol | 1707 | C15H26O | 222 |
| 918 | Sesquichamaenol | 1744 | C15H22O2 | 234 |
| 919 | (E,E)-Methyl farnesoate | 1765 | C16H26O2 | 250 |
| 920 | trans-2-Hydroxycalamenene | 1753 | C15H22O | 218 |
| 921 | a-Santalol acetate | 1756 | C17H26O2 | 262 |
| 922 | 8-Acetoxyelemol | 1759 | C17H26O2 | 262 |
| 923 | Nootkatone | 1782 | C15H22O | 218 |
| 924 | Striatol | 1550 | C15H26O | 222 |
| 925 | Eremophila-1(10),11-dien-9b-ol | 1552 | C15H24O | 220 |
| 926 | Longipinanol | 1559 | C15H26O | 222 |
| 927 | Brachyl oxide | 1599 | C15H24O | 220 |
| 928 | Humulene epoxide 2 | 1602 | C15H24O | 220 |
| 929 | Copaen-15-ol | 1661 | C15H24O | 220 |
| 930 | Isonaviculol | 1743 | C15H26O | 222 |
| 931 | Cyperenal | 1741 | C15H22O | 218 |
| 932 | g-Curcumen-15-al | 1744 | C15H22O | 218 |
| 933 | Brachylaenalone A | 1802 | C15H20O2 | 232 |
| 934 | Muurola-4,10(14)-dien-8a-ol | 1594 | C15H24O | 220 |
| 935 | Cadina-1(10),4-dien-8a-ol | 1637 | C15H24O | 220 |
| 936 | Hexyl acetate | 1006 | C8H16O2 | 144 |
| 937 | Muurola-4,10(14)-dien-8b-ol | 1675 | C15H24O | 220 |
| 938 | (Z)-Nuciferol | 1695 | C15H22O | 218 |
| 939 | (Z)-g-Curcumen-12-ol | 1701 | C15H24O | 220 |
| 940 | (E)-Nuciferol | 1715 | C15H22O | 218 |
| 941 | (Z)-g-Curcumyl acetate | 1767 | C17H26O2 | 262 |
| 942 | (Z)-Nuciferyl acetate | 1793 | C17H24O2 | 260 |
| 943 | (Z)-Nuciferyl isobutyrate | 1916 | C19H28O2 | 288 |
| 944 | (Z)-g-Curcumenyl isobutyrate | 1920 | C19H30O2 | 290 |
| 945 | (Z)-Nuciferyl 2-methylbutyrate | 2003 | C20H30O2 | 302 |
| 946 | (Z)-g-Curcumyl 2-methylbutyrate | 2011 | C20H32O2 | 304 |
| 947 | Drim-8-en-7-one | 1778 | C15H24O | 220 |
| 948 | 1-Oxo-a-longipinene | 1639 | C15H22O | 218 |
| 949 | g-Bicyclohomofarnesal | 1784 | C16H26O | 234 |
| 950 | Geosmin | 1392 | C12H22O | 182 |
| 951 | Muurol-4-en-6a-ol | 1609 | C15H26O | 222 |
| 952 | Veticadine oxide | 1482 | C15H24O | 220 |
| 953 | Cubenol | 1630 | C15H26O | 222 |
| 954 | 4-epi-Cubebol | 1490 | C15H26O | 222 |
| 955 | Muurol-4-en-3,8-dione | 1753 | C15H22O2 | 234 |
| 956 | 3-Acetoxyamorpha-4,7(11)-dien-8-one | 1950 | C17H24O3 | 276 |
| 957 | (E)-4,8-Dimethylnona-1,3,7-triene | 1103 | C11H18 | 150 |
| 958 | Geijerene | 1139 | C12H18 | 162 |
| 959 | Albene | 1154 | C12H18 | 162 |
| 960 | Trinoranastreptene | 1197 | C12H16 | 160 |
| 961 | 1,4a-Dimethyl-1,2,3,4,4a,5,6,7-octahydro-naphthalene | 1233 | C12H20 | 164 |

TABLE 1-continued

List of exemplary terpenes

| No. | chemical name | RI (DB1) | formula | MW |
|---|---|---|---|---|
| 962 | Pregeijerene | 1288 | C12H18 | 162 |
| 963 | (Z)-2,6,10-Trimethylundeca-2,6-diene | 1305 | C14H26 | 194 |
| 964 | Isocyclobazzanene | 1319 | C15H24 | 204 |
| 965 | 8,9-Didehydrocycloisolongifolene | 1320 | C15H22 | 202 |
| 966 | (E)-2,6,10-Trimethylundeca-2,6-diene | 1321 | C14H26 | 194 |
| 967 | Cyprotene | 1322 | C14H24 | 192 |
| 968 | Presilphiperfol-1-ene | 1325 | C15H24 | 204 |
| 969 | 7aH-Silphiperfol-5-ene | 1329 | C15H24 | 204 |
| 970 | Brasila-5,10-diene | 1335 | C15H24 | 204 |
| 971 | Bicycloax-4(15)-ene | 1336 | C15H24 | 204 |
| 972 | Bicycloelemene | 1338 | C15H24 | 204 |
| 973 | d-Elemene | 1340 | C15H24 | 204 |
| 974 | 3,10-Dihydro-1,4-dimethylazulene | 1342 | C12H14 | 158 |
| 975 | Presilphiperfol-7-ene | 1342 | C15H24 | 204 |
| 976 | Pentalenene | 1343 | C15H24 | 204 |
| 977 | African-5-ene | 1350 | C15H24 | 204 |
| 978 | African-2(6)-ene | 1350 | C15H24 | 204 |
| 979 | Maali-1,3-diene | 1347 | C15H22 | 202 |
| 980 | Silphin-1-ene | 1350 | C15H24 | 204 |
| 981 | 7bH-Silphiperfol-5-ene | 1352 | C15H24 | 204 |
| 982 | a-Cubebene | 1355 | C15H24 | 204 |
| 983 | Tamariscene | 1355 | C15H24 | 204 |
| 984 | Africa-1,5-diene | 1355 | C15H22 | 202 |
| 985 | African-1-ene | 1356 | C15H24 | 204 |
| 986 | Bicycloax-3-ene | 1357 | C15H24 | 204 |
| 987 | Silphiperfola-5,7(14)-diene | 1360 | C15H22 | 202 |
| 988 | a-Longipinene | 1360 | C15H24 | 204 |
| 989 | Clovene | 1365 | C15H24 | 204 |
| 990 | Cyperadiene | 1365 | C15H22 | 202 |
| 991 | Cyclomyltaylane | 1366 | C15H24 | 204 |
| 992 | 1-epi-a-Pinguisene | 1367 | C15H24 | 204 |
| 993 | Brasila-5(10),6-diene | 1370 | C15H24 | 204 |
| 994 | Anastreptene | 1373 | C15H22 | 202 |
| 995 | Capnell-9(12)-ene | 1372 | C15H24 | 204 |
| 996 | a-Ylangene | 1376 | C15H24 | 204 |
| 997 | Isopatchoula-3,5-diene | 1377 | C15H22 | 202 |
| 998 | Cyclosativene | 1378 | C15H24 | 204 |
| 999 | Hirsutene | 1378 | C15H24 | 204 |
| 1000 | a-Copaene | 1379 | C15H24 | 204 |
| 1001 | a-Bourbonene | 1378 | C15H24 | 204 |
| 1002 | Daucene | 1380 | C15H24 | 204 |
| 1003 | Silphiperfol-6-ene | 1378 | C15H24 | 204 |
| 1004 | Bourbon-7-ene | 1381 | C15H24 | 204 |
| 1005 | a-Elemene | 1381 | C15H24 | 204 |
| 1006 | Isodauca-4,7(14)-diene | 1381 | C15H24 | 204 |
| 1007 | Isoledene | 1382 | C15H24 | 204 |
| 1008 | Protoillud-6-ene | 1382 | C15H24 | 204 |
| 1009 | Longicyclene | 1382 | C15H24 | 204 |
| 1010 | Modhephene | 1383 | C15H24 | 204 |
| 1011 | Pacifigorgia-1(9),10-diene | 1384 | C15H24 | 204 |
| 1012 | 3-epi-African-5-ene | 1384 | C15H24 | 204 |
| 1013 | 10-epi-Italicene | 1384 | C15H24 | 204 |
| 1014 | Asterisca-3(15),6-diene | 1385 | C15H24 | 204 |
| 1015 | a-Funebrene | 1385 | C15H24 | 204 |
| 1016 | b-Panasinsene | 1385 | C15H24 | 204 |
| 1017 | Bicycloopposit-4-ene | 1386 | C15H24 | 204 |
| 1018 | b-Bourbonene | 1386 | C15H24 | 204 |
| 1019 | Isodauca-4,6-diene | 1385 | C15H24 | 204 |
| 1020 | African-2-ene | 1387 | C15H24 | 204 |
| 1021 | 7-epi-Sesquithujene | 1387 | C15H24 | 204 |
| 1022 | b-Patchoulene | 1388 | C15H24 | 204 |
| 1023 | a-Duprezianene | 1388 | C15H24 | 204 |
| 1024 | b-Elemene | 1389 | C15H24 | 204 |
| 1025 | a-Isocomene | 1389 | C15H24 | 204 |
| 1026 | 1,5-di-epi-a-Bourbonene | 1389 | C15H24 | 204 |
| 1027 | b-Cubebene | 1390 | C15H24 | 204 |
| 1028 | 1,5-di-epi-b-Bourbonene | 1390 | C15H24 | 204 |
| 1029 | African-3-ene | 1391 | C15H24 | 204 |
| 1030 | Bicyclo-4(15)-oppositene | 1391 | C15H24 | 204 |
| 1031 | Isolongifolene | 1393 | C15H24 | 204 |
| 1032 | Isodauca-6,9-diene | 1393 | C15H24 | 204 |
| 1033 | Sativene | 1394 | C15H24 | 204 |
| 1034 | Pacifigorgia-1,10-diene | 1400 | C15H24 | 204 |

TABLE 1-continued

List of exemplary terpenes

| No. | chemical name | RI (DB1) | formula | MW |
|---|---|---|---|---|
| 1035 | Petasitene | 1398 | C15H24 | 204 |
| 1036 | Sesquithujene | 1399 | C15H24 | 204 |
| 1037 | African-3(15)-ene | 1400 | C15H24 | 204 |
| 1038 | Cyperene | 1402 | C15H24 | 204 |
| 1039 | b-Longipinene | 1403 | C15H24 | 204 |
| 1040 | 7-epi-a-Cedrene | 1404 | C15H24 | 204 |
| 1041 | Helifolene | 1406 | C15H24 | 204 |
| 1042 | 7-epi-Helifolene | 1406 | C15H24 | 204 |
| 1043 | Italicene | 1408 | C15H24 | 204 |
| 1044 | Isocaryophyllene | 1409 | C15H24 | 204 |
| 1045 | b-Isocomene | 1411 | C15H24 | 204 |
| 1046 | Longifolene | 1411 | C15H24 | 204 |
| 1047 | Ylanga-2,4(15)-diene | 1411 | C15H22 | 202 |
| 1048 | cis-a-Bergamotene | 1411 | C15H24 | 204 |
| 1049 | allo-Isolongifolene | 1412 | C15H24 | 204 |
| 1050 | Cycloseychellene | 1413 | C15H24 | 204 |
| 1051 | a-Gurjunene | 1413 | C15H24 | 204 |
| 1052 | a-Barbatene | 1414 | C15H24 | 204 |
| 1053 | b-Funebrene | 1418 | C15H24 | 204 |
| 1054 | b-Maaliene | 1414 | C15H24 | 204 |
| 1055 | Pacifigorgia-1(6),10-diene | 1414 | C15H24 | 204 |
| 1056 | Cascarilladiene | 1416 | C15H24 | 204 |
| 1057 | Isosativene | 1416 | C15H24 | 204 |
| 1058 | Tritomarene | 1416 | C15H24 | 204 |
| 1059 | a-Microbiotene | 1414 | C15H24 | 204 |
| 1060 | Aristolene | 1423 | C15H24 | 204 |
| 1061 | a-Cedrene | 1418 | C15H24 | 204 |
| 1062 | Pacifigorgia-2,10-diene | 1422 | C15H24 | 204 |
| 1063 | b-Ylangene | 1420 | C15H24 | 204 |
| 1064 | (Z)-b-Farnesene | 1420 | C15H24 | 204 |
| 1065 | Acora-3,5-diene | 1421 | C15H24 | 204 |
| 1066 | (E)-b-Caryophyllene | 1421 | C15H24 | 204 |
| 1067 | a-Santalene | 1422 | C15H24 | 204 |
| 1068 | Spirovetiva-1(10),6-diene | 1422 | C15H24 | 204 |
| 1069 | b-Duprezianene | 1423 | C15H24 | 204 |
| 1070 | Opposita-4(15),7-diene | 1423 | C15H24 | 204 |
| 1071 | b-Cedrene | 1424 | C15H24 | 204 |
| 1072 | Opposita-4(15),11-diene | 1424 | C15H24 | 204 |
| 1073 | Selina-3,6-diene | 1424 | C15H24 | 204 |
| 1074 | Bourbon-11-ene | 1424 | C15H24 | 204 |
| 1075 | Dauca-3,8-diene | 1428 | C15H24 | 204 |
| 1076 | Elema-1,3,7(11),8-tetraene | 1428 | C15H22 | 202 |
| 1077 | g-Elemene | 1429 | C15H24 | 204 |
| 1078 | Isobarbatene | 1428 | C15H24 | 204 |
| 1079 | g-Maaliene | 1428 | C15H24 | 204 |
| 1080 | Aristola-1(10),8-diene | 1429 | C15H22 | 202 |
| 1081 | Chenopodene | 1430 | C15H24 | 204 |
| 1082 | b-Copaene | 1430 | C15H24 | 204 |
| 1083 | Thujopsene | 1434 | C15H24 | 204 |
| 1084 | Selina-4(15),5-diene | 1433 | C15H24 | 204 |
| 1085 | Pacifigorgia-2(10),11-diene | 1435 | C15H24 | 204 |
| 1086 | trans-a-Bergamotene | 1434 | C15H24 | 204 |
| 1087 | a-Pinguisene | 1436 | C15H24 | 204 |
| 1088 | b-Sesquifenchene | 1437 | C15H24 | 204 |
| 1089 | Sesquisabinene A | 1435 | C15H24 | 204 |
| 1090 | Calarene | 1437 | C15H24 | 204 |
| 1091 | Cubeb-11-ene | 1445 | C15H24 | 204 |
| 1092 | b-Gorgonene | 1440 | C15H24 | 204 |
| 1093 | a-Maalinene | 1440 | C15H24 | 204 |
| 1094 | Cyclofarnesa-5(14),8,10-triene | 1441 | C15H24 | 204 |
| 1095 | a-Guaiene | 1440 | C15H24 | 204 |
| 1096 | Acora-3,9-diene | 1442 | C15H24 | 204 |
| 1097 | Aromadendrene | 1443 | C15H24 | 204 |
| 1098 | Brasila-1(6),5(10)-diene | 1442 | C15H24 | 204 |
| 1099 | Isobazzanene | 1442 | C15H24 | 204 |
| 1100 | Guaia-6,9-diene | 1443 | C15H24 | 204 |
| 1101 | Nardosina-7,9,11-triene | 1444 | C15H22 | 202 |
| 1102 | 4aH,10aH-Guaia-1(5),6-diene | 1445 | C15H24 | 204 |
| 1103 | Isogermacrene D | 1445 | C15H24 | 204 |
| 1104 | Selina-5,11-diene | 1444 | C15H24 | 204 |
| 1105 | Eremophila-1(10),6-diene | 1445 | C15H24 | 204 |
| 1106 | b-Barbatene | 1445 | C15H24 | 204 |
| 1107 | Cadina-4,11-diene | 1458 | C15H24 | 204 |
| 1108 | Erythrodiene | 1446 | C15H24 | 204 |
| 1109 | epi-b-Santalene | 1446 | C15H24 | 204 |

TABLE 1-continued

List of exemplary terpenes

| No. | chemical name | RI (DB1) | formula | MW |
|---|---|---|---|---|
| 1110 | Sesquisabinene B | 1446 | C15H24 | 204 |
| 1111 | Seychellene | 1447 | C15H24 | 204 |
| 1112 | Cadina-3,5-diene | 1448 | C15H24 | 204 |
| 1113 | (E)-b-Farnesene | 1446 | C15H24 | 204 |
| 1114 | 4bH,10aH-Guaia-1(5),6-diene | 1448 | C15H24 | 204 |
| 1115 | Selina-4(15),6-diene | 1450 | C15H24 | 204 |
| 1116 | a-Himachalene | 1450 | C15H24 | 204 |
| 1117 | Prezizaene | 1452 | C15H24 | 204 |
| 1118 | Bourbon-7(11)-ene | 1454 | C15H24 | 204 |
| 1119 | a-Humulene | 1455 | C15H24 | 204 |
| 1120 | e-Muurolene | 1455 | C15H24 | 204 |
| 1121 | a-Panasinsene | 1455 | C15H24 | 204 |
| 1122 | Zizaene | 1456 | C15H24 | 204 |
| 1123 | a-Neoclovene | 1456 | C15H24 | 204 |
| 1124 | Valerena-4,7(11)-diene | 1456 | C15H24 | 204 |
| 1125 | Acora-3,10(14)-diene | 1457 | C15H24 | 204 |
| 1126 | Selina-4(15),7-diene | 1457 | C15H24 | 204 |
| 1127 | b-Spathulene | 1457 | C15H22 | 202 |
| 1128 | Muurola-4,11-diene | 1458 | C15H24 | 204 |
| 1129 | Selina-2,4-diene | 1462 | C15H24 | 204 |
| 1130 | (Z,Z)-a-Farnesene | 1460 | C15H24 | 204 |
| 1131 | b-Santalene | 1460 | C15H24 | 204 |
| 1132 | 7bH,10bH-Cadina-1(6),4-diene | 1460 | C15H24 | 204 |
| 1133 | Rotundene | 1461 | C15H24 | 204 |
| 1134 | Selina-3,7-diene | 1460 | C15H24 | 204 |
| 1135 | Striatene | 1458 | C15H24 | 204 |
| 1136 | allo-Aromadendrene | 1462 | C15H24 | 204 |
| 1137 | Aromadendr-9-ene | 1463 | C15H24 | 204 |
| 1138 | a-Patchoulene | 1467 | C15H24 | 204 |
| 1139 | a-Acoradiene | 1464 | C15H24 | 204 |
| 1140 | Carota-5,8-diene | 1465 | C15H24 | 204 |
| 1141 | b-Acoradiene | 1465 | C15H24 | 204 |
| 1142 | 4,5-di-epi-Aristolochene | 1470 | C15H24 | 204 |
| 1143 | Selina-4,7-diene | 1469 | C15H24 | 204 |
| 1144 | 2-epi-(E)-b-Caryophyllene | 1467 | C15H24 | 204 |
| 1145 | g-Muurolene | 1474 | C15H24 | 204 |
| 1146 | Amorpha-4,11-diene | 1472 | C15H24 | 204 |
| 1147 | 7aH,10bH-Cadina-1(6),4-diene | 1472 | C15H24 | 204 |
| 1148 | ar-Curcumene | 1473 | C15H22 | 202 |
| 1149 | Eudesma-1,4(15),11-triene | 1472 | C15H22 | 202 |
| 1150 | Eudesma-2,4,11-triene | 1471 | C15H22 | 202 |
| 1151 | g-Gurjunene | 1472 | C15H24 | 204 |
| 1152 | Ishwarane | 1468 | C15H24 | 204 |
| 1153 | Valenca-2,9,11-trIene | 1473 | C15H22 | 202 |
| 1154 | b-Chamigrene | 1474 | C15H24 | 204 |
| 1155 | (3E,6Z)-a-Farnesene | 1475 | C15H24 | 204 |
| 1156 | Selina-4,11-diene | 1475 | C15H24 | 204 |
| 1157 | b-Microbiotene | 1473 | C15H24 | 204 |
| 1158 | a-Amorphene | 1477 | C15H24 | 204 |
| 1159 | g-Curcumene | 1475 | C15H24 | 204 |
| 1160 | Herbertene | 1476 | C15H22 | 202 |
| 1161 | Zierene | 1476 | C15H22 | 202 |
| 1162 | a-Neocallitropsene | 1475 | C15H24 | 204 |
| 1163 | Amorpha-4,7(11)-diene | 1476 | C15H24 | 204 |
| 1164 | 5-epi-Aristolochene | 1477 | C15H24 | 204 |
| 1165 | Isobicyclogermacrene | 1477 | C15H24 | 204 |
| 1166 | b-Neoclovene | 1475 | C15H24 | 204 |
| 1167 | trans-b-Bergamotene | 1480 | C15H24 | 204 |
| 1168 | g-Himachalene | 1479 | C15H24 | 204 |
| 1169 | Laurene | 1483 | C15H20 | 200 |
| 1170 | Germacrene D | 1479 | C15H24 | 204 |
| 1171 | (3Z,6E)-a-Farnesene | 1480 | C15H24 | 204 |
| 1172 | a-Vetispirene | 1481 | C15H22 | 202 |
| 1173 | e-Cadinene | 1483 | C15H24 | 204 |
| 1174 | g-Humulene | 1483 | C15H24 | 204 |
| 1175 | Isolepidozene | 1483 | C15H24 | 204 |
| 1176 | cis-Eudesma-6,11-diene | 1484 | C15H24 | 204 |
| 1177 | Nardosina-9,11-diene | 1484 | C15H24 | 204 |
| 1178 | Nardosina-1(10),11-diene | 1484 | C15H24 | 204 |
| 1179 | Eudesma-3,5,11-triene | 1485 | C15H22 | 202 |
| 1180 | Aristolochene | 1486 | C15H24 | 204 |
| 1181 | Eremophilene | 1486 | C15H24 | 204 |
| 1182 | d-Selinene | 1490 | C15H24 | 204 |
| 1183 | b-Vetispirene | 1486 | C15H22 | 202 |
| 1184 | Bicyclosesquiphellandrene | 1487 | C15H24 | 204 |

TABLE 1-continued

List of exemplary terpenes

| No. | chemical name | RI (DB1) | formula | MW |
|---|---|---|---|---|
| 1185 | b-Selinene | 1486 | C15H24 | 204 |
| 1186 | g-Amorphene | 1492 | C15H24 | 204 |
| 1187 | allo-Aromadendr-9-ene | 1489 | C15H24 | 204 |
| 1188 | Eremophila-1(10),7-diene | 1488 | C15H24 | 204 |
| 1189 | Selina-3,5-diene | 1486 | C15H24 | 204 |
| 1190 | Zingiberene | 1489 | C15H24 | 204 |
| 1191 | b-Alaskene | 1495 | C15H24 | 204 |
| 1192 | Ledene | 1491 | C15H24 | 204 |
| 1193 | Drim-8(12)-ene | 1497 | C15H26 | 206 |
| 1194 | Valencene | 1494 | C15H24 | 204 |
| 1195 | epi-Zonarene | 1494 | C15H24 | 204 |
| 1196 | (Z)-a-Bisabolene | 1494 | C15H24 | 204 |
| 1197 | a-Selinene | 1494 | C15H24 | 204 |
| 1198 | Bicyclogermacrene | 1494 | C15H24 | 204 |
| 1199 | Caparratriene | 1493 | C15H26 | 206 |
| 1200 | Eudesma-2,4(15),11-triene | 1495 | C15H22 | 202 |
| 1201 | Hinesene | 1495 | C15H24 | 204 |
| 1202 | a-Muurolene | 1496 | C15H24 | 204 |
| 1203 | Aciphyllene | 1495 | C15H24 | 204 |
| 1204 | a-Cuprenene | 1497 | C15H24 | 204 |
| 1205 | Cuparene | 1498 | C15H22 | 202 |
| 1206 | g-Patchoulene | 1497 | C15H24 | 204 |
| 1207 | e-Amorphene | 1498 | C15H24 | 204 |
| 1208 | g-Guaiene | 1499 | C15H24 | 204 |
| 1209 | b-Pinguisene | 1500 | C15H24 | 204 |
| 1210 | d-Amorphene | 1499 | C15H24 | 204 |
| 1211 | (E,E)-a-Farnesene | 1498 | C15H24 | 204 |
| 1212 | 1aH,10aH-Guaia-4,6-diene | 1500 | C15H24 | 204 |
| 1213 | b-Himachalene | 1500 | C15H24 | 204 |
| 1214 | D7(14)-ar-Himachalene | 1501 | C15H20 | 200 |
| 1215 | b-Bisabolene | 1503 | C15H24 | 204 |
| 1216 | a-Chamigrene | 1503 | C15H24 | 204 |
| 1217 | Eremophila-1(10),8,11-triene | 1504 | C15H22 | 202 |
| 1218 | Germacrene A | 1503 | C15H24 | 204 |
| 1219 | Isorotundene | 1503 | C15H24 | 204 |
| 1220 | a-Bulnesene | 1503 | C15H24 | 204 |
| 1221 | b-Curcumene | 1503 | C15H24 | 204 |
| 1222 | Drimenene | 1503 | C15H24 | 204 |
| 1223 | Pseudowiddrene | 1503 | C15H24 | 204 |
| 1224 | a-Alaskene | 1512 | C15H24 | 204 |
| 1225 | (Z)-g-Bisabolene | 1505 | C15H24 | 204 |
| 1226 | g-Cadinene | 1507 | C15H24 | 204 |
| 1227 | Nootkatene | 1512 | C15H22 | 202 |
| 1228 | Cyclobazzanene | 1514 | C15H24 | 204 |
| 1229 | cis-Calamenene | 1517 | C15H22 | 202 |
| 1230 | b-Sesquiphellandrene | 1516 | C15H24 | 204 |
| 1231 | D7,8-ar-Himachalene | 1518 | C15H20 | 200 |
| 1232 | 7-epi-a-Selinene | 1519 | C15H24 | 204 |
| 1233 | b-Bazzanene | 1519 | C15H24 | 204 |
| 1234 | d-Cadinene | 1520 | C15H24 | 204 |
| 1235 | (E)-g-Bisabolene | 1521 | C15H24 | 204 |
| 1236 | trans-Calamenene | 1517 | C15H22 | 202 |
| 1237 | Zonarene | 1521 | C15H24 | 204 |
| 1238 | b-Cadinene | 1526 | C15H24 | 204 |
| 1239 | g-Cuprenene | 1523 | C15H24 | 204 |
| 1240 | Spirovetiva-1(10),7(11)-diene | 1523 | C15H24 | 204 |
| 1241 | g-Vetivenene | 1525 | C15H22 | 202 |
| 1242 | Cadina-1,4-diene | 1523 | C15H24 | 204 |
| 1243 | w-Cadinene | 1526 | C15H24 | 204 |
| 1244 | a-Calacorene | 1527 | C15H20 | 200 |
| 1245 | Eremophila-1(10),7(11)-diene | 1527 | C15H24 | 204 |
| 1246 | ar-Himachalene | 1528 | C15H22 | 202 |
| 1247 | (E)-a-Bisabolene | 1530 | C15H24 | 204 |
| 1248 | 5-epi-Laurene | 1531 | C15H20 | 200 |
| 1249 | 1,4-Dimethylazulene | 1532 | C12H12 | 156 |
| 1250 | Selina-4(15),7(11)-diene | 1534 | C15H24 | 204 |
| 1251 | a-Cadinene | 1534 | C15H24 | 204 |
| 1252 | w-Amorphene | 1540 | C15H24 | 204 |
| 1253 | d-Cuprenene | 1546 | C15H24 | 204 |
| 1254 | (1(10)E,4Z)-Germacrene B | 1543 | C15H24 | 204 |
| 1255 | Selina-3,7(11)-diene | 1542 | C15H24 | 204 |
| 1256 | Germacrene B | 1552 | C15H24 | 204 |
| 1257 | b-Vetivenene | 1552 | C15H22 | 202 |
| 1258 | g-Calacorene | 1554 | C15H20 | 200 |

TABLE 1-continued

List of exemplary terpenes

| No. | chemical name | RI (DB1) | formula | MW |
|---|---|---|---|---|
| 1259 | (3E,7E)-4,8,12-Trimethyltrideca-1,3,7,11-tetraene | 1565 | C16H26 | 218 |
| 1260 | Cadalene | 1659 | C15H18 | 198 |
| 1261 | Daucalene | 1671 | C15H18 | 198 |
| 1262 | Chamazulene | 1719 | C14H16 | 184 |
| 1263 | Guaiazulene | 1761 | C15H18 | 198 |
| 1264 | 6-epi-b-Cubebene | 1449 | C15H24 | 204 |
| 1265 | e-Cuprenene | 1524 | C15H24 | 204 |
| 1266 | Gymnomitra-3(15),4-diene | 1413 | C15H22 | 202 |
| 1267 | Tenuifolene | 1570 | C15H22 | 202 |
| 1268 | ar-Tenuifolene | 1528 | C15H20 | 200 |
| 1269 | trans-Eudesma-3,5-diene | 1490 | C15H24 | 204 |
| 1270 | Pethybrene | 1440 | C15H24 | 204 |
| 1271 | Premnaspirodiene | 1516 | C15H24 | 204 |
| 1272 | Spirolepechinene | 1450 | C15H24 | 204 |
| 1273 | trans-Dauca-4(11),7-diene | 1554 | C15H24 | 204 |
| 1274 | trans-Dauca-4(11),8-diene | 1529 | C15H24 | 204 |
| 1275 | Cadina-1(10),3,7(11)-triene | 1575 | C15H22 | 202 |
| 1276 | 7,8-Dehydro-a-acoradiene | 1450 | C15H22 | 202 |
| 1277 | cis-Muurola-4(15),5-diene | 1462 | C15H24 | 204 |
| 1278 | Patchoula-2,4(15)-diene | 1434 | C15H22 | 202 |
| 1279 | Norrotundene | 1421 | C14H22 | 190 |
| 1280 | cis-b-Guaiene | 1488 | C15H24 | 204 |
| 1281 | Bisaboia-1,3,5,11-tetraene | 1461 | C15H24 | 204 |
| 1282 | 4-epi-b-Patchoulene | 1376 | C15H24 | 204 |
| 1283 | d-Patchoulene | 1466 | C15H24 | 204 |
| 1284 | e-Patchoulene | 1473 | C15H24 | 204 |
| 1285 | 10-epi-Muurola-4,11-diene | 1458 | C15H24 | 204 |
| 1286 | Dauca-8,11-diene | 1431 | C15H24 | 204 |
| 1287 | Neotrifaradiene | 1365 | C15H24 | 204 |
| 1288 | Sandvicene | 1399 | C15H24 | 204 |
| 1289 | Trifara-9,14-diene | 1403 | C15H24 | 204 |
| 1290 | cis-Muurola-3,5-diene | 1447 | C15H24 | 204 |
| 1291 | Pacifigorgia-6,10-diene | 1429 | C15H24 | 204 |
| 1292 | b-Bulnesene | 1558 | C15H24 | 204 |
| 1293 | Isocalamenene | 1527 | C15H22 | 202 |
| 1294 | Myltayl-4(12)-ene | 1452 | C15H24 | 204 |
| 1295 | 3,7-di-epi-Trifara-9,14-diene | 1399 | C15H24 | 204 |
| 1296 | 6-epi-a-Cubebene | 1418 | C15H24 | 204 |
| 1297 | 2-Sterpurene | 1351 | C15H24 | 204 |
| 1298 | a-Corocalen | 1602 | C15H20 | 200 |
| 1299 | Lactarazulene | 1796 | C15H16 | 196 |
| 1300 | Prenyllimonene (Isomer 1) | 1436 | C15H24 | 204 |
| 1301 | Prenyllimonene (Isomer 2) | 1450 | C15H24 | 204 |
| 1302 | Cadina-1(10),7(11)-diene | 1538 | C15H24 | 204 |
| 1303 | Elema-1,3,7-triene | 1346 | C15H24 | 204 |
| 1304 | 7-epi-Cadina-1(10),11-diene | 1525 | C15H24 | 204 |
| 1305 | Cadina-1(10),11-diene | 1480 | C15H24 | 204 |
| 1306 | Vetivazulene | 1790 | C15H18 | 198 |
| 1307 | Mintsulphide | 1734 | C15H24S | 236 |
| 1308 | Brasila-1,10-diene | 1307 | C15H24 | 204 |
| 1309 | Drim-8-ene | 1442 | C15H26 | 206 |
| 1310 | Selina-4(15),7,11-triene | 1469 | C15H22 | 202 |
| 1311 | 5,6-Dehydroalaskene | 1371 | C15H22 | 202 |
| 1312 | (all-Z)-6,9,12,15-Heneicosatetraene | 2048 | C21H36 | 288 |
| 1313 | Isoperillene | 1073 | C10H14O | 150 |
| 1314 | (E)-Cinnamyl isovalerate | 1641 | C14H18O2 | 218 |
| 1315 | (E)-Cinnamyl isobutyrate | 1543 | C13H16O2 | 204 |
| 1316 | (E)-Cinnamyl propionate | 1500 | C12H14O2 | 190 |
| 1317 | (Z)-Isobutyl cinnamate | 1593 | C13H16O2 | 204 |
| 1318 | Phenylethyl tiglate | 1547 | C13H16O2 | 204 |
| 1319 | 7-epi-Eremophila-1(10),8,11-triene | 1508 | C15H22 | 202 |
| 1320 | 5-Hydroxymarsupellyl acetate | 1814 | C17H26O3 | 278 |
| 1321 | Marsupellyl acetate | 1681 | C17H26O2 | 262 |
| 1322 | 4-epi-Marsupellyl acetate | 1733 | C17H26O2 | 262 |
| 1323 | (E)-Methyl p-methoxycinnamate | 1625 | C11H12O3 | 192 |
| 1324 | (Z)-Methyl p-methoxycinnamate | 1543 | C11H12O3 | 192 |
| 1325 | 4-epi-Marsupellol | 1614 | C15H24O | 220 |
| 1326 | (Z)-Cinnamyl propionate | 1552 | C12H14O2 | 190 |
| 1327 | (E)-Isobutyl cinnamate | 1633 | C13H16O2 | 204 |
| 1328 | Methyl 4-methoxymandelate | 1511 | C10H12O4 | 196 |
| 1329 | (E)-Isoamyl cinnamate | 1697 | C14H18O2 | 218 |
| 1330 | Pentadecanoic acid | 1823 | C15H30O2 | 242 |
| 1331 | Methyl o-methoxybenzoate | 1300 | C9H10O3 | 166 |
| 1332 | Patchenol | 1305 | C11H18O | 166 |

TABLE 1-continued

List of exemplary terpenes

| No. | chemical name | RI (DB1) | formula | MW |
|---|---|---|---|---|
| 1333 | Syringa aldehyde | 1599 | C9H10O4 | 182 |
| 1334 | Methyl 3-methylorsellinate | 1674 | C10H12O4 | 196 |
| 1335 | Dihydroactinidiolide | 1487 | C11H16O2 | 180 |
| 1336 | b-Ionone epoxide | 1460 | C13H20O2 | 208 |
| 1337 | Oxoisophorone | 1111 | C9H12O2 | 152 |
| 1338 | Sabina ketone | 1132 | C9H14O | 138 |
| 1339 | 2,6-Di-tert-butyl-4-methylphenol | 1492 | C15H24O | 220 |
| 1340 | Cadin-1(10)-ene 5,11-oxide | 1574 | C15H24O | 220 |
| 1341 | 6,11-Epoxyisodaucane | 1463 | C15H26O | 222 |
| 1342 | 3-Acetoxy-b-ionone | 1752 | C15H22O3 | 250 |
| 1343 | Nardosina-7,9-dien-11-ol | 1596 | C15H24O | 220 |
| 1344 | Porosadienol | 1627 | C15H24O | 220 |
| 1345 | a-Ionone epoxide (Isomer 2) | 1512 | C13H20O2 | 208 |
| 1346 | Cabreuva oxide A | 1437 | C15H24O | 220 |
| 1347 | Cabreuva oxide B | 1452 | C15H24O | 220 |
| 1348 | Cabreuva oxide C | 1456 | C15H24O | 220 |
| 1349 | (E)-o-Methoxycinnamaldehyde | 1477 | C10H10O2 | 162 |
| 1350 | (Z)-o-Methoxycinnamaldehyde | 1408 | C10H10O2 | 162 |
| 1351 | Hydrocinnamyl acetate | 1336 | C11H14O2 | 178 |
| 1352 | N-Methyl methyl anthranilate | 1372 | C9H11O2N | 165 |
| 1353 | Abietal | 2261 | C20H30O | 286 |
| 1354 | trans-Totarol | 2241 | C20H30O | 286 |
| 1355 | Dehydrogeosmin | 1362 | C12H20O | 180 |
| 1356 | 1bH,5aH,7bH-Guaia-3,10(14)-dien-11-ol | 1646 | C15H24O | 220 |
| 1357 | 9a,11-Epoxy-1bH,5aH,7bH,9bH-guaia-3,10(14)-diene | 1587 | C15H22O | 218 |
| 1358 | 4-(4-Hydroxyphenyl)-2-butanone | 1508 | C10H12O2 | 164 |
| 1359 | 15-Norlabdan-8-ol | 1943 | C19H36O | 280 |
| 1360 | Oxoisoambrox | 1819 | C16H26O2 | 250 |
| 1361 | Sclareolide | 2022 | C16H24O3 | 264 |
| 1362 | 1-Decanol | 1264 | C10H22O | 158 |
| 1363 | Amberone | 1810 | C17H26O | 246 |
| 1364 | Methyl arachidonate | 2217 | C21H34O2 | 318 |
| 1365 | Cyclomytaylan-15-ol | 1641 | C15H24O | 220 |
| 1366 | Tridenson | 1633 | C15H26O | 222 |
| 1367 | Tridensenal | 1617 | C15H26O | 222 |
| 1368 | 6b-Acetoxyeudesm-4(15)-en-7b-ol | 1898 | C18H30O2 | 278 |
| 1369 | Tridensenone | 1815 | C15H20O | 216 |
| 1370 | 2,6,6-Trimethylcyclohexanone | 1023 | C9H16O | 140 |
| 1371 | 2,6,6-Trimethylcyclohex-2-enone | 1045 | C9H14O | 138 |
| 1372 | Acetoxycedren-13-ol | 1782 | C17H26O2 | 262 |
| 1373 | 4-Isopropylcyclohexanol (Isomer 1) | 1126 | C9H18O | 142 |
| 1374 | 3-Hydroxy-4-methoxybenzyl alcohol | 1421 | C8H10O3 | 154 |
| 1375 | a-Ambrinol (Isomer 1) | 1382 | C13H22O | 194 |
| 1376 | a-Ambrinol (Isomer 2) | 1410 | C13H22O | 194 |
| 1377 | Thymohydroquinone | 1509 | C10H14O2 | 166 |
| 1378 | Oreodaphnenol | 1484 | C15H24O | 220 |
| 1379 | Ambrox | 1747 | C16H28O | 236 |
| 1380 | 4-Isopropylphenol | 1201 | C9H12O | 136 |
| 1381 | Scopoletine | 1888 | C10H8O4 | 192 |
| 1382 | 2,5-Dimethoxy-4-isopropyltoluene | 1400 | C12H18O2 | 194 |
| 1383 | Silphiperfol-5-en-3-one | 1533 | C15H22O | 218 |
| 1384 | Clovenol | 1575 | C15H24O | 220 |
| 1385 | trans-6-Hydroxyisocalamenene | 1782 | C15H22O | 218 |
| 1386 | 1,4-trans-6-Methoxyisocalamenene | 1722 | C16H24O | 232 |
| 1387 | Non-1-ene | 837 | C9H18 | 126 |
| 1388 | Mintoxide | 1565 | C15H24O | 220 |
| 1389 | 6-Methylheptan-2,4-dione | 975 | C8H14O2 | 142 |
| 1390 | 5-Methylheptan-2,4-dione | 966 | C8H14O2 | 142 |
| 1391 | 2,2-Dimethyl-7-isobutyl-2H,5H-pyrano[4.3-b]pyran-5-one | 1770 | C14H18O3 | 234 |
| 1392 | 2,2-Dimethyl-7-secbutyl-2H,5H-pyrano[4.3-b]pyran-5-one | 1764 | C14H18O3 | 234 |
| 1393 | Cyclo-b-ionone | 1329 | C13H20O | 192 |
| 1394 | Germacra-4(15),5,10(14)-trien-1a-ol | 1680 | C15H24O | 220 |
| 1395 | Eudesma-4(15),7-dien-1b-ol | 1671 | C15H24O | 220 |
| 1396 | Cadina-4,10(14)-dien-1a-ol | 1662 | C15H24O | 220 |
| 1397 | b-Calacorene | 1541 | C15H20 | 200 |
| 1398 | 1a,10a-Epoxyamorph-4-ene | 1569 | C15H24O | 220 |
| 1399 | Muurola-4,10(14)-dien-1-ol | 1626 | C15H24O | 220 |
| 1400 | Caryophylla-3(15),7(14)-dien-6-ol | 1635 | C15H24O | 220 |
| 1401 | 4(15)-Dehydroglobulol | 1597 | C15H24O | 220 |
| 1402 | trans-Bisabola-1(6),10-dien-2,3-diol | 1758 | C15H26O2 | 238 |

TABLE 1-continued

List of exemplary terpenes

| No. | chemical name | RI (DB1) | formula | MW |
|---|---|---|---|---|
| 1403 | 6,10-Epoxybisabol-2-en-12-al | 1664 | C15H24O2 | 236 |
| 1404 | 6,10-Epoxybisabol-3-en-12-al | 1677 | C15H24O2 | 236 |
| 1405 | 11-epi-6,10-Epoxybisabol-3-en-12-al | 1649 | C15H24O2 | 236 |
| 1406 | Acora-3,5-dien-11-ol | 1574 | C15H24O | 220 |
| 1407 | Acora-2,4(15)-dien-11-ol | 1616 | C15H24O | 220 |
| 1408 | 7-epi-Bisabol-1-one | 1718 | C15H24O | 220 |
| 1409 | (E)-trans-a-Bergamota-2,10-dien-12-al | 1679 | C15H22O | 218 |
| 1410 | Helifolen-12-al (syn-syn-syn) | 1611 | C16H24O | 232 |
| 1411 | Italicene ether | 1531 | C15H24O | 220 |
| 1412 | 7-epi-b-Bisabolol | 1657 | C15H26O | 222 |
| 1413 | Bisabol-1-one | 1712 | C15H24O | 220 |
| 1414 | Humulene epoxide 1 | 1593 | C14H22O | 206 |
| 1415 | 10-epi-Italicene ether | 1511 | C15H24O | 220 |
| 1416 | 3-Hydroxybisabola-1(6),10-dien-2-one | 1748 | C15H24O2 | 236 |
| 1417 | b-Bisabolol | 1659 | C15H26O | 222 |
| 1418 | 10-epi-Junenol | 1581 | C15H26O | 222 |
| 1419 | Junenol | 1617 | C15H26O | 222 |
| 1420 | 1,10-di-epi-Cubenol | 1615 | C15H26O | 222 |
| 1421 | Carquejyl acetate | 1284 | C12H16O2 | 192 |
| 1422 | (E)-Dendrolasin | 1566 | C15H22O | 218 |
| 1423 | Artemisyl acetate | 1164 | C12H20O2 | 196 |
| 1424 | Artedouglasia oxide C | 1507 | C15H22O3 | 250 |
| 1425 | Artedouglasia oxide A | 1517 | C15H22O3 | 250 |
| 1426 | 1-Undecanol | 1363 | C11H24O | 172 |
| 1427 | Laciniata furanone H | 1530 | C15H22O3 | 250 |
| 1428 | Lanciniata furanone F | 1514 | C15H22O3 | 250 |
| 1429 | Artedouglasia oxide B | 1561 | C15H22O3 | 250 |
| 1430 | Artedouglasia oxide D | 1542 | C15H22O3 | 250 |
| 1431 | Cymen-8-ol | 1169 | C10H14O | 150 |
| 1432 | 2,2,9-Trimethyl-1,6-dioxaspiro[4.4]nona-3,8-diene | 1079 | C10H14O2 | 166 |
| 1433 | Menthyl formate | 1230 | C11H20O2 | 184 |
| 1434 | Folifolone | 1090 | C10H14O | 150 |
| 1435 | Santolina alcohol | 1029 | C10H18O | 154 |
| 1436 | cis-p-Mentha-1(7),8-dien-2-ol | 1217 | C10H16O | 152 |
| 1437 | trans-p-Mentha-1(7),8-dien-2-ol | 1176 | C10H16O | 152 |
| 1438 | trans-p-Menth-2-en-1-ol | 1116 | C10H18O | 154 |
| 1439 | cis-p-Mentha-2,8-dien-1-ol | 1125 | C10H16O | 152 |
| 1440 | trans-p-Mentha-2,8-dien-1-ol | 1113 | C10H16O | 152 |
| 1441 | Dehydrosabinaketone | 1100 | C9H12O | 136 |
| 1442 | 4-Hydroxy-4-methylcyclohex-2-enone | 1089 | C7H10O2 | 126 |
| 1443 | 2-(1-Hydroxyethyl)-5-methyl-5-vinyltetrahydrofuran | 1054 | C9H16O2 | 156 |
| 1444 | trans-Arbusculone | 1036 | C9H14O2 | 154 |
| 1445 | Lavender lactone | 1006 | C7H10O2 | 126 |
| 1446 | Pulegone epoxide | 1238 | C10H16O2 | 168 |
| 1447 | 3-Methylcyclohexanone | 928 | C7H12O | 112 |
| 1448 | trans-Linalool oxide acetate | 1274 | C12H20O3 | 212 |
| 1449 | Fragranyl acetate | 1331 | C11H18O2 | 182 |
| 1450 | 6-Methyl-6-(3-methylphenyl)-2-heptanone | 1609 | C15H22O | 218 |
| 1451 | 3-exo-Acetoxybornyl acetate | 1520 | C14H22O4 | 254 |
| 1452 | 3-exo-Acetoxyborneol | 1402 | C12H20O3 | 212 |
| 1453 | 3-exo-Hydroxybornyl acetate | 1393 | C12H20O3 | 212 |
| 1454 | Lavandulyl acetate | 1275 | C12H20O2 | 196 |
| 1455 | 5-Hydroxymarsupellol | 1776 | C15H24O2 | 236 |
| 1456 | b-Isolongibornene | 1440 | C15H24 | 204 |
| 1457 | Geranyl propionate | 1486 | C13H22O2 | 210 |
| 1458 | (E)-Isosafrol | 1356 | C10H10O2 | 162 |
| 1459 | 2,3-Dihydrofarnesol | 1674 | C15H28O | 224 |
| 1460 | Methyl 4-hydroxymandelate | 1572 | C9H10O4 | 182 |
| 1461 | Methyl 3-(4-methoxyphenyl)-propionate | 1494 | C11H14O3 | 194 |
| 1462 | Methyl 3,5-dimethoxyphenylacetate | 1603 | C11H14O4 | 210 |
| 1463 | 2a-Hydroxyamorpha-4,7(11)-diene | 1678 | C15H24O | 220 |
| 1464 | l-Hepten-3-one | 956 | C7H12O | 112 |
| 1465 | Ferulyl angelate | 1682 | C15H20O3 | 248 |
| 1466 | Undecanal | 1290 | C11H22O | 170 |
| 1467 | n-Hexadecanoic acid | 1951 | C16H32O2 | 256 |
| 1468 | n-Tetradecanoic acid | 1748 | C14H28O2 | 228 |
| 1469 | n-Dodecanoic acid | 1554 | C12H24O2 | 200 |

TABLE 1-continued

List of exemplary terpenes

| No. | chemical name | RI (DB1) | formula | MW |
|---|---|---|---|---|
| 1470 | n-Decanal | 1180 | C10H20O | 156 |
| 1471 | Axenol (Gleenol) | 1574 | C15H26O | 222 |
| 1472 | epi-Methyl jasmonate | 1637 | C13H20O3 | 224 |
| 1473 | 5-Ethylcyclopent-1-enecarbaldehyde | 1010 | C8H12O | 124 |
| 1474 | Methyl hexanoate | 905 | C7H14O2 | 130 |
| 1475 | Methyl undecanoate | 1400 | C12H24O2 | 200 |
| 1476 | Methyl dodecanoate | 1500 | C13H26O2 | 214 |
| 1477 | Methyl tridecanoate | 1600 | C14H28O2 | 228 |
| 1478 | Methyl myristoleate | 1683 | C15H28O2 | 240 |
| 1479 | (Z)-Methyl pentadec-10-enoate | 1786 | C16H30O2 | 254 |
| 1480 | Methyl palmitoleate | 1877 | C17H32O2 | 268 |
| 1481 | (Z)-Methyl Heptadec-10-enoate | 1978 | C18H34O2 | 282 |
| 1482 | Methyl heptadecanoate | 2001 | C17H34O2 | 270 |
| 1483 | Methyl oleate | 2082 | C19H36O2 | 296 |
| 1484 | Dihydroedulan | 1290 | C13H22O | 194 |
| 1485 | 2-Methylbenzofuran | 1149 | C9H8O | 132 |
| 1486 | (all-Z)-Methyl Docosa-4,7,10,13,16,19-hexaenoate | 2395 | C23H34O2 | 342 |
| 1487 | (Z,Z)-Methyl docosa-13,16-dienoate | 2433 | C23H42O2 | 350 |
| 1488 | Methyl erucate | 2440 | C23H44O2 | 352 |
| 1489 | Methyl behenate | 2459 | C23H46O2 | 354 |
| 1490 | Methyl tricosanoate | 2558 | C24H48O2 | 368 |
| 1491 | Methyl nervonate | 2650 | C25H48O2 | 380 |
| 1492 | (Z)-Methyl eicosa-11-enoate | 2248 | C21H40O2 | 324 |
| 1493 | Methyl lignocerate | 2695 | C25H50O2 | 382 |
| 1494 | Methyl arachidate | 2306 | C21H42O2 | 326 |
| 1495 | Methyl heneicosanoate (C-21) | 2412 | C22H44O2 | 340 |
| 1496 | Methyl stearate | 2104 | C19H38O2 | 298 |
| 1497 | (all-Z)-Methyl eicosa-11,14-dienoate | 2243 | C22H40O2 | 336 |
| 1498 | Methyl elaidate | 2084 | C19H36O2 | 296 |
| 1499 | Methyl linolenate | 2036 | C19H32O2 | 292 |
| 1500 | Methyl linoleate | 2046 | C19H34O2 | 294 |
| 1501 | Methyl palmitate | 1901 | C17H34O2 | 270 |
| 1502 | Methyl pentadecanoate | 1796 | C16H32O2 | 256 |
| 1503 | Methyl myristate | 1700 | C15H30O2 | 242 |
| 1504 | Methyl octanoate | 1100 | C91H8O2 | 158 |
| 1505 | Methyl nonanoate | 1208 | C10H20O2 | 172 |
| 1506 | Methyl decanoate | 1300 | C11H22O2 | 186 |
| 1507 | (3Z,9E)-Isoligustilide | 1824 | C12H14O2 | 190 |
| 1508 | (Z)-3-Butyliden-4,5,6,7-tetrahydrophthalide | 1697 | C12H16O2 | 192 |
| 1509 | Neophytadiene (Isomer 1) | 1807 | C20H38 | 278 |
| 1510 | Neophytadiene (Isomer 2) | 1830 | C20H38 | 278 |
| 1511 | Neophytadiene (Isomer 3) | 1849 | C20H38 | 278 |
| 1512 | Eudesm-3-ene 6,7-oxide | 1787 | C15H24O | 220 |
| 1513 | Eudesma-3,7(11)-dien-8-one | 1745 | C15H22O | 218 |
| 1514 | 5-Methylfurfural | 941 | C6H6O2 | 110 |
| 1515 | g-Costol | 1732 | C15H24O | 220 |
| 1516 | a-Costol | 1761 | C15H24O | 220 |
| 1517 | b-Costol | 1754 | C15H24O | 220 |
| 1518 | Dehydrocostunolide | 1956 | C15H18O2 | 230 |
| 1519 | Dihydrodehydrocostus lactone | 1903 | C15H20O2 | 232 |
| 1520 | Eudesma-4(15),11-dien-8-one | 1643 | C15H22O | 218 |
| 1521 | (E)-15,16-Bisnorlabda-8(17),12-dien-14-al | 2051 | C18H28O | 260 |
| 1522 | (E)-15,16-Bisnorlabda-8(17),11-dien-13-one | 1958 | C18H28O | 260 |
| 1523 | Albicanol | 1736 | C16H28O | 236 |
| 1524 | g-Bicyclofarnesal | 1656 | C15H24O | 220 |
| 1525 | trans-6,6,10-Trimethyl-2-decalone | 1505 | C13H22O | 194 |
| 1526 | Coronarin E | 2095 | C20H28O | 284 |
| 1527 | 10-Hydroxy-4-oplopanone | 1708 | C15H26O2 | 238 |
| 1528 | Valerenic acid | 1843 | C15H22O2 | 234 |
| 1529 | Vulgarone A | 1580 | C15H22O | 218 |
| 1530 | Artemisiatriene | 923 | C10H16 | 136 |
| 1531 | 2-Methylbutyl octanoate | 1427 | C13H26O2 | 214 |
| 1532 | Hexyl hexanoate | 1363 | C12H24O2 | 200 |
| 1533 | (E)-2-Decenal | 1240 | C10H18O | 154 |
| 1534 | 2-methylbutyl hexanoate | 1235 | C11H22O2 | 186 |
| 1535 | n-Hexyl 2-methylbutanoate | 1220 | C11H22O2 | 186 |
| 1536 | n-Hexyl butanoate | 1176 | C10H20O2 | 172 |
| 1537 | (E)-2-Heptenal | 942 | C7H12O | 112 |
| 1538 | Fenchyl acetate (Isomer) | 1224 | C12H20O2 | 196 |
| 1539 | 11-Nordrim-8-en-12-al | 1609 | C14H22O | 206 |
| 1540 | Undecanoic acid | 1452 | C11H22O2 | 186 |

TABLE 1-continued

List of exemplary terpenes

| No. | chemical name | RI (DB1) | formula | MW |
|---|---|---|---|---|
| 1541 | Allyl-2,4-di-acetoxybenzene | 1592 | C13H14O4 | 234 |
| 1542 | n-Decane | 993 | C10H22 | 142 |
| 1543 | n-Dodecane | 1200 | C12H26 | 170 |
| 1544 | n-Tridecane | 1300 | C13H28 | 184 |
| 1545 | n-Tetradecane | 1392 | C14H30 | 198 |
| 1546 | n-Pentadecane | 1500 | C15H32 | 212 |
| 1547 | n-Hexadecane | 1600 | C16H34 | 226 |
| 1548 | n-Heptadecane | 1700 | C17H36 | 240 |
| 1549 | n-Octadecane | 1792 | C18H38 | 254 |
| 1550 | n-Eicosane (C-20) | 2000 | C20H42 | 282 |
| 1551 | n-Heneicosane (C-21) | 2100 | C21H44 | 296 |
| 1552 | n-Docosane (C-22) | 2200 | C22H46 | 310 |
| 1553 | n-Tricosane (C-23) | 2301 | C23H48 | 324 |
| 1554 | n-Tetracosane (C-24) | 2400 | C24H50 | 338 |
| 1555 | n-Pentacosane (C-25) | 2498 | C25H52 | 352 |
| 1556 | n-Hexacosane (C-26) | 2598 | C26H54 | 366 |
| 1557 | Verbenene | 982 | C10H14 | 134 |
| 1558 | trans-Chrysanthenyl acetate | 1214 | C12H18O2 | 194 |
| 1559 | trans-Chrysanthenol | 1096 | C10H16O | 152 |
| 1560 | (Z)-2,6-Dimethylocta-1,5,7-trien-3-ol | 1048 | C10H16O | 152 |
| 1561 | (E)-2,6-Dimethylocta-1,5,7-trien-3-ol | 1058 | C10H16O | 152 |
| 1562 | Dihydrodiplophylline | 1896 | C15H22O2 | 234 |
| 1563 | Diplophylline | 1965 | C15H20O2 | 232 |
| 1564 | Ginsensene | 1353 | C15H24 | 204 |
| 1565 | 2-Methyl-2,5-divinyltetrahydrofuran | 900 | C9H14O | 138 |
| 1566 | 5-Ethyl-2-methyl-2-vinyltetrahydrofuran | 893 | C9H16O | 140 |
| 1567 | (all-E)-1,7-Dimethylcyclodeca-1,4,7-triene | 1274 | C12H18 | 162 |
| 1568 | Salviadienol | 1545 | C15H24O | 220 |
| 1569 | Torilenol | 1599 | C13H20O | 192 |
| 1570 | Betaer-13-ene | 2040 | C20H32 | 272 |
| 1571 | Ethylbenzene | 843 | C8H10 | 106 |
| 1572 | 4-epi-11-Noraristola-9,11-diene | 1399 | C14H20 | 188 |
| 1573 | 4-epi-11-Noraristola-1,9,11-triene | 1419 | C14H18 | 186 |
| 1574 | 4-epi-11-Noraristola-1(10),11-diene | 1409 | C14H20 | 188 |
| 1575 | 4-Ethylguiacol | 1257 | C9H12O2 | 152 |
| 1576 | 2-Hydroxy-4-methoxyacetophenone | 1294 | C9H10O3 | 166 |
| 1577 | 4-Vinylanisol | 1134 | C9H10O | 134 |
| 1578 | p-Ethylanisol | 1099 | C9H12O | 136 |
| 1579 | 1-Acetoxy-4-ethylbenzene | 1238 | C10H12O2 | 164 |
| 1580 | Tetradecanal | 1596 | C14H28O | 212 |
| 1581 | 4-Ethylphenol | 1139 | C8H10O | 122 |
| 1582 | Dehydropinguisenol | 1800 | C15H20O2 | 232 |
| 1583 | Fusicocca-2,5-diene | 2020 | C20H32 | 272 |
| 1584 | Crispatanolide | 1760 | C15H22O2 | 234 |
| 1585 | (+)-Himachala-2,4-diene | 1433 | C15H24 | 204 |
| 1586 | Polygodial | 1839 | C15H22O2 | 234 |
| 1587 | 9-epi-Polygodial | 1960 | C15H22O2 | 234 |
| 1588 | Dihydrofrullanolide | 1874 | C15H22O2 | 234 |
| 1589 | Eudesma-3,11-dien-8-one | 1666 | C15H22O | 218 |
| 1590 | 5,8a-Dimethyl-3,4,4a,7,8,8a-hexahydro-1H-naphthalen-2-one | 1464 | C12H18O | 178 |
| 1591 | 8a-Hydroxyeudesma-3,11-diene | 1668 | C15H24O | 220 |
| 1592 | 6,11-Epoxyeudesmane | 1521 | C15H26O | 222 |
| 1593 | Eudesma-5,7(11)-diene | 1543 | C15H24 | 204 |
| 1594 | 6b-Hydroxyeudesm-11-ene | 1643 | C15H26O | 222 |
| 1595 | 6a-Hydroxyeudesm-11-ene | 1598 | C15H26O | 222 |
| 1596 | 6,7-seco-Eudesm-7(11)-en-6-al | 1615 | C15H26O | 222 |
| 1597 | Ipsenol | 1083 | C10H18O | 154 |
| 1598 | Phytane | 1808 | C20H42 | 282 |
| 1599 | Farnesane | 1375 | C15H32 | 212 |
| 1600 | b-n-Octyl-g-butanolide | 1655 | C12H22O2 | 198 |
| 1601 | Crocetane | 1810 | C20H42 | 282 |
| 1602 | Pristane | 1706 | C19H40 | 268 |
| 1603 | cis-Eudesma-4,11-dien-8-ol | 1648 | C15H24O | 220 |
| 1604 | Bisabola-1(6),2,10Z-trien-12-al | 1733 | C15H22O | 218 |
| 1605 | 8,9-Epoxyselina-4,11-diene | 1597 | C15H24O | 218 |
| 1606 | Eudesma-4(15),11-dien-5-ol | 1629 | C15H24O | 220 |
| 1607 | cis-Eudesma-4(15),11-dien-5-ol | 1623 | C15H24O | 220 |
| 1608 | Pentadecanal | 1702 | C15H30O | 226 |
| 1609 | 3-Methylbutanolide | 909 | C5H8O2 | 100 |
| 1610 | 2-n-Propyl-g-butanolide | 1100 | C7H12O2 | 128 |

TABLE 1-continued

List of exemplary terpenes

| No. | chemical name | RI (DB1) | formula | MW |
|---|---|---|---|---|
| 1611 | 2-n-Pentyl-g-butanolide | 1311 | C9H16O2 | 156 |
| 1612 | 2-Ethylbutanolide | 1000 | C6H10O2 | 114 |
| 1613 | 2-Methylbutanolide | 902 | C5H8O2 | 100 |
| 1614 | 4-Allyl-g-butanolide | 1090 | C7H10O2 | 126 |
| 1615 | d-Tetradecalactone | 1893 | C14H26O2 | 226 |
| 1616 | d-Tridecanolide | 1786 | C13H24O2 | 212 |
| 1617 | d-Dodecanolide | 1675 | C12H22O2 | 198 |
| 1618 | g-n-Tetradecyl-g-butanolide | 2720 | C18H34O2 | 282 |
| 1619 | d-Hexaolide | 1044 | C6H10O2 | 114 |
| 1620 | N-2-[(4-Hydroxyphenyl)-ethyl]-tiglamide | 2325 | C13H17O2N | 219 |
| 1621 | 4-Hydroxy-b-ionone | 1628 | C13H20O2 | 208 |
| 1622 | (E)-Megastigm-7-en-3,9-dione (t) | 1572 | C13H20O2 | 208 |
| 1623 | a-Helmiscapene | 1447 | C15H24 | 204 |
| 1624 | Methyl 2-(2-methylbutyroxy)-3-methylpentanoate | 1339 | C12H22O4 | 230 |
| 1625 | 7,8-Dihydro-b-ionol | 1431 | C13H24O | 196 |
| 1626 | Dodecyl acetate | 1585 | C14H28O2 | 228 |
| 1627 | (Z)-Heptadec-8-ene | 1666 | C17H34 | 238 |
| 1628 | cis-Dracunculifolione | 1500 | C15H24O | 220 |
| 1629 | Italicen-13-ol | 1670 | C15H24O | 220 |
| 1630 | 10-epi-cis-Dracunculifoliol | 1533 | C15H26O | 222 |
| 1631 | cis-Dracunculifoliol | 1534 | C15H26O | 222 |
| 1632 | trans-Dracunculifoliol | 1581 | C15H26O | 222 |
| 1633 | 3-Hydroxy-b-ionone | 1647 | C13H20O2 | 208 |
| 1634 | 3-Hydroxy-5,6-dihydro-b-ionone | 1609 | C13H22O2 | 210 |
| 1635 | (E)-b-Santalol | 1680 | C15H24O | 220 |
| 1636 | o-Cymene | 976 | C10H14 | 134 |
| 1637 | Methyl 11-methyltridecanoate | 1668 | C15H30O2 | 242 |
| 1638 | Libocedrol | 2326 | C22H30O4 | 358 |
| 1639 | Aristol-1(10)-en-12-ol | 1712 | C15H24O | 220 |
| 1640 | Costunolide | 1914 | C15H20O2 | 232 |
| 1641 | 7-Hydroxyeudesm-4-en-6-one | 1703 | C15H24O2 | 236 |
| 1642 | Aristol-1(10)-en-12-al | 1704 | C15H22O | 218 |
| 1643 | Methyl 10-methyldodecanoate | 1575 | C14H28O2 | 228 |
| 1644 | Dotriacontane | 3200 | C32H66 | 450 |
| 1645 | Eudesma-4(15),7(11),9-trien-12-olide | 1971 | C15H18O2 | 230 |
| 1646 | Isogermafurenolide | 1867 | C15H20O2 | 232 |
| 1647 | Chloranthalactone A | 1941 | C15H16O2 | 228 |
| 1648 | Ethyl decanoate | 1375 | C12H24O2 | 200 |
| 1649 | Ethyl palmitate | 1954 | C18H36O2 | 284 |
| 1650 | 7,11-Epoxymegastigm-5-en-9-one | 1551 | C13H20O2 | 208 |
| 1651 | Neoiso-isopulegol | 1164 | C10H18O | 154 |
| 1652 | b-Ionol | 1400 | C13H22O | 194 |
| 1653 | 8-Hydroxylinalyl tiglate | 1760 | C15H24O3 | 252 |
| 1654 | (Z)-Methyl 4-(geranyloxy)-cinnamate | 2334 | C20H26O3 | 314 |
| 1655 | (E)-Methyl 4-(geranyloxy)-cinnamate | 2461 | C20H26O3 | 314 |
| 1656 | Tetradecyl acetate | 1775 | C16H32O2 | 256 |
| 1657 | Benzyl 3-methylbutyrate | 1366 | C12H16O2 | 192 |
| 1658 | Benzyl 2-methylbutyrate | 1360 | C12H16O2 | 192 |
| 1659 | Decanoic acid | 1347 | C10H20O2 | 172 |
| 1660 | n-Octanoic acid | 1156 | C8H16O2 | 144 |
| 1661 | Dihydromayurone | 1591 | C14H22O | 206 |
| 1662 | Ethyl hexadecanoate | 1990 | C18H36O2 | 284 |
| 1663 | 8-Hydroxylinalyl propionate | 1551 | C13H22O3 | 226 |
| 1664 | 4-Acetoxy-3-methoxyacetophenone | 1434 | C11H12O4 | 208 |
| 1665 | o-Anisaldehyde | 1202 | C8H8O2 | 136 |
| 1666 | 2-Octanone | 964 | C8H16O | 128 |
| 1667 | (E)-trans-Bergamotol | 1680 | C15H24O | 220 |
| 1668 | Methyl 3-methylpentanoate | 853 | C7H14O2 | 130 |
| 1669 | Methyl 3,7-dimethyloctanoate | 1207 | C11H22O2 | 186 |
| 1670 | Methyl 4-methylhexanoate | 974 | C8H16O2 | 144 |
| 1671 | Muurolan-4,7-oxide | 1480 | C15H26O | 222 |
| 1672 | cis-Totarol | 2252 | C20H30O | 286 |
| 1673 | 4-Butyl-3-methyl-g-butanolide | 1252 | C9H16O2 | 156 |
| 1674 | Isosaccogynol | 1740 | C15H22O | 218 |
| 1675 | Isosaccogynone | 1744 | C15H20O | 216 |
| 1676 | Taylorione | 1617 | C15H22O | 218 |
| 1677 | 2-a-Acetoxy-11-methoxyamorpha-4,7-diene | 1846 | C18H28O3 | 292 |
| 1678 | 2-a-Acetoxyamorpha-4,7(11)-dien-8-one | 1963 | C17H24O3 | 276 |

TABLE 1-continued

List of exemplary terpenes

| No. | chemical name | RI (DB1) | formula | MW |
|---|---|---|---|---|
| 1679 | Neryl formate | 1265 | C11H18O2 | 182 |
| 1680 | Geranyl butyrate | 1534 | C15H26O2 | 238 |
| 1681 | Nerylpropionate | 1451 | C14H24O2 | 224 |
| 1682 | Geranyl tiglate | 1670 | C15H24O2 | 236 |
| 1683 | 2-Methylbutyl angelate | 1130 | C10H18O2 | 170 |
| 1684 | 3-Methylbutyl angelate | 1125 | C10H18O2 | 170 |
| 1685 | Methallyl angelate | 1040 | C9H14O2 | 154 |
| 1686 | 3-Methylbutyl methacrylate | 1018 | C9H16O2 | 156 |
| 1687 | 3-Methylbutyl isobutyrate | 994 | C9H18O2 | 158 |
| 1688 | 3-Methylpentyl isobutyrate | 1095 | C10H20O2 | 172 |
| 1689 | 3-Methylpentyl angelate | 1230 | C11H20O2 | 184 |
| 1690 | Butyl angelate | 1065 | C9H16O2 | 156 |
| 1691 | 10-Acetoxy-4-oplopanone | 1874 | C17H28O3 | 280 |
| 1692 | Butyl benzoate | 1556 | C11H14O2 | 178 |
| 1693 | Propyl benzoate | 1347 | C10H12O2 | 164 |
| 1694 | Phenylacetonitrile | 1085 | C8H7N | 117 |
| 1695 | Hexadecyl acetate | 1847 | C18H36O2 | 284 |
| 1696 | Octadecyl acetate | 2084 | C20H40O2 | 312 |
| 1697 | Octadecanal | 2012 | C18H36O | 268 |
| 1698 | Hexadecanal | 1782 | C16H32O | 240 |
| 1699 | Heptacosane | 2700 | C27H56 | 380 |
| 1700 | Docosanal | 2338 | C22H44O | 324 |
| 1701 | cis-b-Elemene | 1381 | C15H24 | 204 |
| 1702 | Eicosanal | 2170 | C20H40O | 296 |
| 1703 | 1-Methyl-3-(2-oxopropyl)-4-(1-methylethenyl)-cyclohexene | 1409 | C13H20O | 192 |
| 1704 | Ginsenol | 1621 | C15H26O | 222 |
| 1705 | 4-n-Propylanisol | 1254 | C10H14O | 150 |
| 1706 | n-Decyl acetate | 1390 | C12H24O2 | 200 |
| 1707 | Dimethyl-tetrasulfide | 1181 | C2H6S4 | 158 |
| 1708 | Dimethyl trisulfide | 942 | C2H6S3 | 126 |
| 1709 | S,S-Dimethyl dithiocarbonate | 935 | C3H6OS2 | 122 |
| 1710 | 2,5-Diethyltetrahydrofuran | 875 | C8H16O | 128 |
| 1711 | Neoiso-isopulegol acetate | 1366 | C12H20O2 | 196 |
| 1712 | Methyl 2-hydroxy-4-methoxy-6-methylbenzoate | 1555 | C10H12O4 | 196 |
| 1713 | 1-Octen-3-yl 3-methylbutyrate | 1315 | C13H24O2 | 212 |
| 1714 | 1-Octen-3-yl 2-methylbutyrate | 1310 | C13H24O2 | 212 |
| 1715 | Oct-1-en-3-yl butyrate | 1266 | C12H22O2 | 198 |
| 1716 | 1-Octen-3-yl isobutyrate | 1223 | C12H22O2 | 198 |
| 1717 | l-Octen-3-yl propanoate | 1181 | C11H20O2 | 184 |
| 1718 | 14-Hydroxy-4,5-dihydro-b-caryophyllene | 1692 | C15H26O | 222 |
| 1719 | 14-Hydroxy-b-caryophyllene | 1656 | C15H24O | 220 |
| 1720 | 4,5-Dihydro-b-caryophyllen-14-al (Isomer 1) | 1610 | C15H24O | 220 |
| 1721 | 4,5-Dihydro-b-caryophyllen-14-al (Isomer 2) | 1621 | C15H24O | 220 |
| 1722 | 4-Desmethylcaryophyll-8(14)-en-5-one | 1521 | C14H22O | 206 |
| 1723 | Isocaryophyllen-14-al (b-Betulenal) | 1630 | C15H22O | 218 |
| 1724 | 1-Angeloyloxyverbenone | 1694 | C15H20O3 | 248 |
| 1725 | 4-Hydroxy-2-methylacetophenone | 1254 | C9H10O2 | 150 |
| 1726 | 7-epi-1,2-Dehydrosesquicineole | 1460 | C15H24O | 220 |
| 1727 | 1,2-Dimethoxybenzene (Veratrol) | 1117 | C8H10O2 | 138 |
| 1728 | (E)-Isoelemicin | 1614 | C12H16O3 | 208 |
| 1729 | (Z)-Isoelemicin | 1559 | C12H16O3 | 208 |
| 1730 | 1,2,4-Trimethoxybenzene | 1330 | C9H12O3 | 168 |
| 1731 | p-Menth-1-en-9-al (Isomer 1) | 1188 | C10H16O | 152 |
| 1732 | p-Menth-1-en-9-al (Isomer 2) | 1190 | C10H16O | 152 |
| 1733 | (Methoxymethyl)-benzene | 964 | C8H10O | 122 |
| 1734 | 1,4-Dimethoxybenzene | 1132 | C8H10O2 | 138 |
| 1735 | 6,10,14-Trimethylpentadecan-2-one | 1817 | C18H36O | 268 |
| 1736 | (Z)-a-Damascone | 1343 | C13H20O | 192 |
| 1737 | Lilac alcohol (2R,2'R,5'S) | 1210 | C10H18O2 | 170 |
| 1738 | Lilac alcohol (2R,2'S,5'S)) | 1196 | C10H18O2 | 170 |
| 1739 | Lilac alcohol (2S,2'S,5'S) | 1185 | C10H18O2 | 170 |
| 1740 | Lilac aldehyde (2R,2'R,5'S) | 1146 | C10H16O2 | 168 |
| 1741 | Lilac aldehyde (2R,2'S,5'S) | 1133 | C10H16O2 | 168 |
| 1742 | Lilac aldehyde (2S,2'S,5'S) | 1124 | C10H16O2 | 168 |
| 1743 | Methyl citronellate | 1245 | C11H20O2 | 184 |
| 1744 | Myli-4(15)-ene | 1418 | C15H22 | 202 |
| 1745 | Maali-4(15)-en-1-ol | 1624 | C15H24O | 220 |
| 1746 | (E)-Taylopyran | 1530 | C15H22O | 218 |
| 1747 | 7-epi-Bourbon-3-ene 5,11-oxide | 1473 | C15H22O | 218 |

TABLE 1-continued

List of exemplary terpenes

| No. | chemical name | RI (DB1) | formula | MW |
|---|---|---|---|---|
| 1748 | Mylian-3-one | 1593 | C15H22O | 218 |
| 1749 | Myli-4(15)-en-3-one | 1610 | C15H20O | 216 |
| 1750 | 5,5-Dimethyl-1-vinylbicyclo-[2.1.1] hexane | 931 | C10H16 | 136 |
| 1751 | Cara-2,4-diene | 900 | C10H14 | 134 |
| 1752 | Eudesm-4(15)en-6-one | 1616 | C15H24O | 220 |
| 1753 | Eudesm-4-en-6-one | 1605 | C15H24O | 220 |
| 1754 | Guaia-3,9-diene 5,11-oxide | 1519 | C15H22O | 218 |
| 1755 | Guaia-3,10(14)-diene 5,11-oxide | 1555 | C15H22O | 218 |
| 1756 | 3-Ethylacetophenone | 1260 | C10H12O | 148 |
| 1757 | 4-Ethylacetophenone | 1240 | C10H12O | 148 |
| 1758 | (6Z,8E)-Megastigma-4,6,8-trien-3-one | 1553 | C13H18O | 190 |
| 1759 | (E,E)-Megastigma-4,6,8-trien-3-one | 1598 | C13H18O | 190 |
| 1760 | Aromadendra-1(10),4(15)-diene | 1506 | C15H22 | 202 |
| 1761 | Perfora-1,7-diene | 1543 | C15H24 | 204 |
| 1762 | Guaia-1(10),11-diene | 1516 | C15H24 | 204 |
| 1763 | Guaia-9,11-diene | 1522 | C15H24 | 204 |
| 1764 | Norpinguisone | 1600 | C14H18O2 | 218 |
| 1765 | Methyl norpinguisonate | 1776 | C15H18O4 | 262 |
| 1766 | Bisabola-1,3,5,7(14)-tetraene | 1484 | C15H22 | 202 |
| 1767 | Lemnalone | 1611 | C15H22O | 218 |
| 1768 | Methyl 2,4-Dimethoxy-6-methylbenzoate | 1588 | C11H14O4 | 210 |
| 1769 | Methyl 6-Methoxy-2-methyl-3,4-methylendioxybenzoate | 1661 | C11H12O5 | 224 |
| 1770 | Methyl 6-Hydroxy-2-methyl-3,4-methylendioxybenzoate | 1640 | C10H10O5 | 210 |
| 1771 | Methyl 3,4,6-trimethoxy-2-methylbenzoate | 1705 | C12H16O5 | 240 |
| 1772 | 4-Methoxyphenylacetaldehyde | 1255 | C9H10O2 | 150 |
| 1773 | Aromadendra-4,9-diene | 1534 | C15H22 | 202 |
| 1774 | Aromadendra-1(10),4-diene | 1462 | C15H22 | 202 |
| 1775 | Aromadendra-4,10(14)-diene | 1440 | C15H22 | 202 |
| 1776 | 5,6-Dihydro-1,4-dimethylazulene | 1428 | C12H14 | 158 |
| 1777 | 3,4,5,6-Tetrahydro-1,4-dimethylazulene | 1246 | C12H16 | 160 |
| 1778 | 2,3,3a,4,5,6-Hexahydro-1,4-dimethylazulen-3-ol | 1447 | C12H18O | 178 |
| 1779 | 3a-Acetoxyamorpha-4,7(11)-diene | 1780 | C17H26O2 | 262 |
| 1780 | Amorpha-2,4,7(11)-triene | 1449 | C15H22 | 202 |
| 1781 | Amorpha-4,7(11)-dien-2-one | 1645 | C15H22O | 218 |
| 1782 | 2a-Acetoxyamorpha-4,7(11)-diene | 1796 | C17H26O2 | 262 |
| 1783 | 2b-Acetoxyamorpha-4,7(11)-diene | 1722 | C17H26O2 | 262 |
| 1784 | 9a-Hydroxyamorpha-4,7(11)-diene | 1680 | C15H24O | 220 |
| 1785 | 7b-Hydroxyamorpha-4,11-diene | 1615 | C15H24O | 220 |
| 1786 | 3a-Hydroxyamorpha-4,7(11)-diene | 1665 | C15H24O | 220 |
| 1787 | Amorpha-4,7(11)-dien-3-one | 1677 | C15H22O | 218 |
| 1788 | Eudesma-4,11-dien-9-one | 1649 | C15H22O | 218 |
| 1789 | 2,8-Epoxyamorpha-4,7(11)-diene | 1597 | C15H22O | 218 |
| 1790 | 5,9-Epoxyamorpha-3,7(11)-diene | 1594 | C15H22O | 218 |
| 1791 | n-Tridecanal | 1493 | C13H26O | 198 |
| 1792 | (E)-Non-2-en-4-one 306 | 1098 | C9H16O | 140 |
| 1793 | (E)-3-Methylnon-2-en-4-one | 1190 | C10H18O | 154 |
| 1794 | Isotheaspirane (Isomer 1) | 1263 | C13H22O | 194 |
| 1795 | Isotheaspirane (Isomer 1) | 1279 | C13H22O | 194 |
| 1796 | Chiloscyphone | 1576 | C15H22O | 218 |
| 1797 | 2-Hydroxy-3,5-dimethoxy-9,10-dihydrophenanthrene | 2251 | C16H16O3 | 256 |
| 1798 | 4,5-Dihydroxy-3-methoxy-9,10-dihydrophenanthrene | 2330 | C15H14O3 | 242 |
| 1799 | Isozierene | 1556 | C15H22 | 202 |
| 1800 | Isogermacrene A | 1502 | C15H24 | 204 |
| 1801 | Iso-b-elemene | 1359 | C15H24 | 204 |
| 1802 | n-Decyl butanoate | 1567 | C14H28O2 | 228 |
| 1803 | g-Palmitolactone | 2081 | C16H30O2 | 254 |
| 1804 | n-Octyl butanoate | 1371 | C12H24O2 | 200 |
| 1805 | Benzyl butanoate | 1313 | C11H14O2 | 178 |
| 1806 | n-Butyl butyrate | 970 | C8H16O2 | 144 |
| 1807 | n-Heptyl butanoate | 1270 | C11H22O2 | 186 |
| 1808 | 2-Phenylethyl butyrate | 1412 | C12H16O2 | 192 |
| 1809 | Ethyl 2-phenylhexanoate | 1617 | C14H20O2 | 220 |
| 1810 | Methyl 4-hydroxybenzoate | 1414 | C8H8O3 | 152 |
| 1811 | n-Propyl 4-hydroxybenzoate | 1584 | C10H12O3 | 180 |
| 1812 | n-Octyl hexanoate | 1567 | C14H28O2 | 228 |

TABLE 1-continued

List of exemplary terpenes

| No. | chemical name | RI (DB1) | formula | MW |
|---|---|---|---|---|
| 1813 | 11-b-Hydroxykauren-15-a-yl acetate | 2459 | C22H34O3 | 346 |
| 1814 | a-Campholenic acid | 1304 | C10H16O2 | 168 |
| 1815 | 5-Acetoxybornan-2-one | 1399 | C12H18O3 | 210 |
| 1816 | n-Heptadecanal | 1908 | C17H34O | 254 |
| 1817 | Ventricos-7(13)-ene | 1357 | C15H24 | 204 |
| 1818 | Helminthogermacrene | 1503 | C15H24 | 204 |
| 1819 | allo-Aromadendra-4(15),10(14)-diene | 1457 | C15H22 | 202 |
| 1820 | Methyl 3-phenylpropanoate | 1242 | C10H12O2 | 164 |
| 1821 | Nepetalactone (Isomer 1) | 1331 | C10H14O2 | 166 |
| 1822 | (all-E)-Geranylcitronellol | 2160 | C20H36O | 292 |
| 1823 | Cyclooctatetraene | 837 | C8H8 | 104 |
| 1824 | 4-(4-Hydroxyphenyl)-butan-2-ol | 1518 | C10H14O2 | 166 |
| 1825 | Lowry's phenol | 1684 | C12H16O4 | 224 |
| 1826 | Platyphyllol | 1588 | C12H16O4 | 224 |
| 1827 | Eugenitine | 1944 | C12H12O4 | 220 |
| 1828 | Isoeugenitine | 1963 | C12H12O4 | 220 |
| 1829 | Dihydrocolumellarine | 1889 | C15H22O2 | 234 |
| 1830 | Myltaylenol | 1727 | C15H24O | 220 |
| 1831 | a-Gorgonene | 1490 | C15H24 | 204 |
| 1832 | Aromadendra-4(15),10(14)dien-1-ol | 1579 | C15H22O | 218 |
| 1833 | 10-epi-Dihydroagarofuran | 1520 | C15H26O | 222 |
| 1834 | 3,7-Dimethyl-3,7-dihydroxyoct-1-ene | 1198 | C10H20O2 | 172 |
| 1835 | Agarospirol | 1635 | C15H26O | 222 |
| 1836 | 10a-Hydroxy-12-prenylguai-11-ene | 2111 | C20H34O | 290 |
| 1837 | 5-Formyl-2-hydroxy-(3-methylbutyro)-phenone | 1617 | C12H14O3 | 206 |
| 1838 | 4-Hydroxybenzaldehyde | 1316 | C7H6O2 | 122 |
| 1839 | 1,3,5-Trimethyl-1,3,5-triazin-2,4,6-trione | 1327 | C6H9O3N3 | 171 |
| 1840 | 5-Formyl-2-hydroxy-(3-hydroxy-3-methylbutyro)-phenone | 1660 | C12H14O4 | 222 |
| 1841 | Octadecanoic acid | 2182 | C18H36O2 | 284 |
| 1842 | Longipinanol, high temp. | 1563 | C15H26O | 222 |
| 1843 | Artemiseol | 970 | C10H16O | 152 |
| 1844 | a-Cyclocitral | 1103 | C10H16O | 152 |
| 1845 | (3E,5Z)-Undeca-1,3,5-triene (Isomer 2) | 1133 | C11H18 | 150 |
| 1846 | Undeca-1,3,5-triene (Isomer 1) | 1117 | C11H18 | 150 |
| 1847 | 4-(4-Methoxyphenyl)-butan-2-one | 1453 | C11H14O2 | 178 |
| 1848 | Atranol | 1511 | C8H8O3 | 152 |
| 1849 | Chloroatranol | 1466 | C8H7O3Cl | 186 |
| 1850 | Myrtenyl methyl ether | 1145 | C11H18O | 166 |
| 1851 | 8,14-Cedrane oxide | 1536 | C15H24O | 220 |
| 1852 | Camphene hydrate | 1143 | C10H18O | 154 |
| 1853 | 6-Camphenone | 1082 | C10H14O | 150 |
| 1854 | Desmethoxyencecalin | 1617 | C13H14O2 | 202 |
| 1855 | Bisabola-1,3,5,7-tetraene | 1554 | C15H22 | 202 |
| 1856 | Myltayl-4-ene | 1383 | C15H24 | 204 |
| 1857 | Gorgon-11-en-4-ol | 1617 | C15H26O | 222 |
| 1858 | a-Taylorione | 1586 | C15H22O | 218 |
| 1859 | Taylocyclan | 1477 | C15H22O | 218 |
| 1860 | Taynudol | 1709 | C15H22O | 218 |
| 1861 | Taylofuran | 1635 | C15H24O2 | 236 |
| 1862 | 3-Acetoxytaylorione | 1918 | C17H24O3 | 276 |
| 1863 | Copalol | 2265 | C20H34O | 290 |
| 1864 | 3a-Acetoxybicyclogermacrene | 1769 | C17H26O2 | 262 |
| 1865 | Plagiooxide | 1420 | C15H26O | 222 |
| 1866 | Gymnomitr-3(15)-en-5b-ol | 1653 | C15H24O | 220 |
| 1867 | 5b-Acetoxy-gymnomitr-3(15)-ene | 1758 | C17H26O2 | 262 |
| 1868 | 4b,5b-Diacetoxygymnomitr-3(15)-ene | 1943 | C19H28O4 | 320 |
| 1869 | 15-Acetoxygymnomitr-3-ene | 1797 | C17H26O2 | 262 |
| 1870 | 3,15-b-Epoxy-4b-acetoxygymnomitrane | 1875 | C17H26O3 | 278 |
| 1871 | 3,15-a-Epoxy-4b-acetoxygymnomitrane | 1887 | C17H26O3 | 278 |
| 1872 | Iso-a-humulene | 1474 | C15H24 | 204 |
| 1873 | cis-Anethol | 1230 | C10H12O | 148 |
| 1874 | Cadina-4,11-dien-15-al | 1704 | C15H22O | 218 |
| 1875 | Cadina-4,11-dien-15-ol | 1713 | C15H26O | 222 |
| 1876 | a-Barbatenal | 1659 | C15H22O | 218 |
| 1877 | 15-Nor-3-gymnomitrone | 1609 | C14H22O | 206 |

TABLE 1-continued

List of exemplary terpenes

| No. | chemical name | RI (DB1) | formula | MW |
|---|---|---|---|---|
| 1878 | Bergaptene | 2023 | C12H8O4 | 216 |
| 1879 | Peucedanin | 2243 | C15H14O4 | 258 |
| 1880 | syn-Copalol | 2165 | C20H34O | 290 |
| 1881 | Melanene | 1455 | C15H24 | 204 |
| 1882 | Panaxene | 1312 | C15H24 | 204 |
| 1883 | Panaginsene | 1336 | C15H24 | 204 |
| 1884 | Iso-g-bisabolene | 1523 | C15H24 | 204 |
| 1885 | Viscida-4,9,14-triene | 1862 | C20H32 | 272 |
| 1886 | Trichodiene | 1523 | C15H24 | 204 |
| 1887 | 2-Methyl-3-(4-methoxyphenyl)-prop-2-ene | 1324 | C11H14O | 162 |
| 1888 | Gymnomitr-3(15)-en-12-oic acid | 1790 | C15H22O2 | 234 |
| 1889 | 12-Acetoxygymnomitr-3(15)-ene | 1795 | C17H26O2 | 262 |
| 1890 | Gymnomitr-3(15)-en-12-al | 1627 | C15H22O | 218 |
| 1891 | Scapanol | 1586 | C15H26O | 222 |
| 1892 | Hydroxycitronellal | 1263 | C10H20O2 | 172 |
| 1893 | 2-(2-Ethoxyethoxy)-ethanol | 985 | C6H14O3 | 134 |
| 1894 | Di-(2-hydroxypropyl)-ether | 1003 | C6H14O3 | 134 |
| 1895 | Benzyl propionate | 1231 | C10H12O2 | 164 |
| 1896 | 2-Methyl-3-(4-isopropylphenyl)-propanal | 1433 | C13H18O | 190 |
| 1897 | (Z)-b-Curcumen-12-ol | 1732 | C15H24O | 120 |
| 1898 | (Z)-b-Phenylethyl cinnamate | 2006 | C17H16O2 | 152 |
| 1899 | (E)-b-Phenylethyl cinnamate | 1123 | C17H16O2 | 252 |
| 1900 | Phenylethyl benzoate | 1815 | C15H14O2 | 126 |
| 1901 | Phenyl ethyl phenylacetate | 1868 | C16H16O2 | 240 |
| 1902 | Phenyl ethyl propionate | 1468 | C11H14O2 | 178 |
| 1903 | 2-(4-Methoxyphenyl)-5-methoxy-2,3-dihydrobenzo[b]furan | 2237 | C16H16O3 | 256 |
| 1904 | (Z)-Coriandrin | 1234 | C12H15ONS2 | 153 |
| 1905 | (Z)-Coridrin | 1708 | C10H9ONS | 191 |
| 1906 | (E)-Coridrin | 1784 | C10H9ONS | 191 |
| 1907 | 2-Methylene-6,6-dimethylcyclohex-3-ene-1-carbaldehyde | 1092 | C10H14O | 150 |
| 1908 | 1-p-Menthan-8-thiol | 1196 | C10H20S | 172 |
| 1909 | 1-p-Menthen-8-thiol | 1279 | C10H18S | 170 |
| 1910 | 5,5-Dimethylcyclohex-2-en-1,4-dione | 1002 | C8H10O2 | 138 |
| 1911 | Neoisomenthol | 1176 | C10H20O | 156 |
| 1912 | Menth-2-en-1,4-diol | 1269 | C10H18O2 | 170 |
| 1913 | Carvone hydrate | 1388 | C10H16O2 | 168 |
| 1914 | Carvone hydrate acetate | 1528 | C12H18O3 | 210 |
| 1915 | 8-Hydroxylinalyl isobutyrate | 1588 | C14H24O3 | 240 |
| 1916 | Lyral | 1637 | C13H22O2 | 210 |
| 1917 | Lyral (Isomer) | 1625 | C13H22O2 | 210 |
| 1918 | 2-(4-tert-butylbenzyl)-propione aldehyde | 1501 | C14H20O | 204 |
| 1919 | Methyl 2-octynoate | 1177 | C9H14O2 | 154 |
| 1920 | Caparapidiol | 1686 | C15H28O2 | 240 |
| 1921 | Jaeschkeanadiol | 1754 | C15H26O2 | 238 |
| 1922 | 2,8-Epithio-cis-p-menthane | 1242 | C10H18S | 170 |
| 1923 | Gorgona-1,4(15),11-triene | 1426 | C15H22 | 202 |
| 1924 | Aromadendra-1(10),3-diene | 1509 | C15H22 | 202 |
| 1925 | 8-Hydroxylinalyl 2-methylbutyrate | 1688 | C15H26O3 | 254 |
| 1926 | trans-Pinane | 951 | C10H18 | 138 |
| 1927 | 4b-Acetoxygymnomitr-3(15)-ene | 1739 | C17H26O2 | 262 |
| 1928 | 1,8-Dimethyl-3-ethyl-2,9-dioxabicyclo[3.3.1]non-7-en-6-one | 1344 | C11H16O3 | 196 |
| 1929 | 2,6-Diethyl-2,3-dihydro-4H-pyran-4-one | 1221 | C9H14O2 | 154 |
| 1930 | Frontaline | 907 | C8H14O2 | 142 |
| 1931 | endo-Brevicomin | 1039 | C9H16O2 | 156 |
| 1932 | cis-Pinane | 963 | C10H18 | 138 |
| 1933 | Chalcograne (Isomer 1) | 1051 | C9H16O | 140 |
| 1934 | Chalcograne (Isomer 2) | 1055 | C9H16O | 140 |
| 1935 | Lineatine | 1102 | C10H16O2 | 168 |
| 1936 | Methyl n-propyl trisufide | 1121 | C4H10S3 | 154 |
| 1937 | (E)n-Propyl 1-propenyl disulfide | 1063 | C6H12S2 | 148 |
| 1938 | Di-n-propyl trisulfide | 1302 | C6H14S3 | 182 |
| 1939 | Methyl n-propyl disulfide | 900 | C4H10S2 | 122 |
| 1940 | Di-n-propyl disulfide | 1081 | C6H14S2 | 150 |
| 1941 | Di-n-propyl tetrasulfide | 1558 | C6H14S4 | 214 |
| 1942 | 5-Pentyl-3,4,5-trimethyl-5H-furan-2-one | 1474 | C12H20O2 | 196 |
| 1943 | Plagiochilline T | 1665 | C15H20O | 216 |

TABLE 1-continued

List of exemplary terpenes

| No. | chemical name | RI (DB1) | formula | MW |
|---|---|---|---|---|
| 1944 | Plagiochilline U | 1625 | C15H22O | 218 |
| 1945 | 5-Methylcyclohex-2-en-1-one | 935 | C7H10O | 110 |
| 1946 | 3-Ethylcyclohexanone | 1020 | C8H14O | 126 |
| 1947 | Methyl 3-ethyl-4-methylpentanoate | 1021 | C9H18O2 | 158 |
| 1948 | 2,4-Diethyloct-1-ene | 1106 | C12H24 | 168 |
| 1949 | Methyl trans-Dihydrojasmonate | 1623 | C13H22O3 | 226 |
| 1950 | cis-Methyl dihydrojasmonate | 1651 | C13H22O3 | 226 |
| 1951 | 1,7-Dioxaspiro[5.5]undecane | 1108 | C9H16O2 | 156 |
| 1952 | (2Z,4E)-Methyl abscisate | 2076 | C16H22O4 | 278 |
| 1953 | (2Z,4E)-Methyl phaseate | 2141 | C16H22O5 | 294 |
| 1954 | (2E,4E)-Methyl abscisate | 2164 | C16H22O4 | 278 |
| 1955 | Pityol | 945 | C8H16O2 | 144 |
| 1956 | 6-Ethyl-2-methyl-2,3-dihydro-4H-pyran-2-one | 1117 | C8H12O2 | 140 |
| 1957 | n-Nonyl acetate | 1283 | C11H22O2 | 186 |
| 1958 | 4-epi-Maaliol | 1549 | C15H26O | 222 |
| 1959 | Plagiochiline H | 1807 | C17H24O3 | 276 |
| 1960 | 5-Methyloctahydrofuro [3,2-b]oxepine | 1028 | C9H16O2 | 156 |
| 1961 | Methyl 2-hydroxyhexanoate | 993 | C7H14O3 | 146 |
| 1962 | Methyl 2-hydroxytetradecanoate | 1838 | C15H30O3 | 258 |
| 1963 | Seudenol | 941 | C7H12O | 112 |
| 1964 | 2,8-Dimethyl-1,7-dioxaspiro[5.5]undecane (Isomer 1) | 1121 | C11H20O2 | 184 |
| 1965 | 2,8-Dimethyl-1,7-dioxaspiro[5.5]undecane (Isomer 2) | 1189 | C11H20O2 | 184 |
| 1966 | 4-Methyl-2-buten-4-olide | 869 | C5H6O2 | 98 |
| 1967 | Methyl 2-methyltetradecanoate | 1758 | C16H32O2 | 256 |
| 1968 | Methyl 3-methylpentanoate | 840 | C7H14O2 | 130 |
| 1969 | Methyl 2-methylundecanoate | 1509 | C13H26O2 | 214 |
| 1970 | Methyl 2-methyldodecanoate | 1550 | C14H28O2 | 228 |
| 1971 | Methyl 2-hydroxyisopentanoate | 845 | C6H12O3 | 132 |
| 1972 | Methyl 2-hydroxypentanoate | 894 | C6H12O3 | 132 |
| 1973 | 4a-Methyloctahydronaphthalen-2-one | 1369 | C11H18O | 166 |
| 1974 | Methyl madelate | 1245 | C9H10O3 | 166 |
| 1975 | Methyl 2-hydroxydodecanoate | 1627 | C13H26O3 | 230 |
| 1976 | 1-Phenylethanol | 1037 | C8H10O | 122 |
| 1977 | 2,3,5-Trimethylvalerolactone | 1158 | C8H14O2 | 142 |
| 1978 | 10-Methyldecalin-2,7-dione | 1520 | C11H16O2 | 180 |
| 1979 | 6-Hexyl-5,6-dihydropyran-2-one | 1551 | C11H18O2 | 182 |
| 1980 | Methyl 2-methylpentadecanoate | 2195 | C17H34O2 | 270 |
| 1981 | 2,3-Epoxycinnamyl alcohol | 1309 | C9H10O2 | 150 |
| 1982 | Methyl 2-methylhexadecanoate | 1972 | C18H36O2 | 284 |

An exemplary therapeutic compound conforming with any of the disclosed embodiments may comprise for instance a compound including at least two of delta-9-tetrahydrocannabinol or tetrahydrocannabinolic acid, and cannabidiol and optionally at least one of the listed terpenes Still further an exemplary therapeutic compound conforming with any of the disclosed embodiments may comprise for instance a compound including 20 mg of delta-9-tetrahydrocannabinol and 10 mg of cannabidiol preferably administered every δ-8 hours as needed. Still further an exemplary therapeutic compound conforming with any of the disclosed embodiments may comprise for instance a compound including 10 mg of delta-9-tetrahydrocannabinol and 5 mg of cannabidiol preferably administered every δ-8 hours as needed. Still further an exemplary therapeutic compound conforming with any of the disclosed embodiments may comprise for instance a compound including 20 mg of delta-9-tetrahydrocannabinol and 20 mg of cannabidiol preferably administered every δ-8 hours as needed. Still further an exemplary therapeutic compound conforming with any of the disclosed embodiments may comprise for instance a compound including 10 mg of delta-9-tetrahydrocannabinol and 10 mg of cannabidiol preferably administered every δ-8 hours as needed. Still further an exemplary therapeutic compound conforming with any of the disclosed embodiments may comprise for instance a compound including 15 mg of delta-9-tetrahydrocannabinol and 10 mg of cannabidiol preferably administered every δ-8 hours as needed.

Further, enumerated embodiments are described below.

Embodiment 1. A pharmaceutical composition comprising: (a) tetrahydrocannabinol (THC) and cannabidiol (CBD) in a THC:CBD ratio of from 1:1.5 to 3:1 by weight; and (b) one or more terpenes listed in Table 1.

Embodiment 2. The pharmaceutical composition of embodiment 1, wherein the THC:CBD ratio is about: 1:1.5, 1:1.4, 1:1.3, 1:1.2, 1:1.1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, or 3:1.

Embodiment 3. The pharmaceutical composition of embodiment 1, wherein the THC:CBD ratio is from 1.5:1 to 2:1.

Embodiment 4. The pharmaceutical composition of embodiment 1, wherein the THC:CBD ratio is about 1.5:1.

Embodiment 5. The pharmaceutical composition of any one of embodiments 1-4, wherein the pharmaceutical composition comprises: 1-50 mg, 5-40 mg, 7.5-30 mg, 10-20 mg, or 12.5-17.5 mg tetrahydrocannabinol (THC) per dose.

Embodiment 6. The pharmaceutical composition of any one of embodiments 1-4, wherein the pharmaceutical composition comprises about: 1 mg, 2.5 mg, 5 mg, 7.5 mg, 10 mg, 12.5 mg, 15 mg, 17.5 mg, 20 mg, 25 mg, 30 mg, 35 mg, 40 mg, 45 mg, or 50 mg tetrahydrocannabinol (THC) per dose.

Embodiment 7. The pharmaceutical composition of any one of embodiments 1-4, wherein the pharmaceutical composition comprises about 10-20 mg tetrahydrocannabinol (THC) per dose.

Embodiment 8. The pharmaceutical composition of any one of embodiments 1-4, wherein the pharmaceutical composition comprises about 15-20 mg tetrahydrocannabinol (THC) per dose.

Embodiment 9. The pharmaceutical composition of any one of embodiments 1-8, wherein the pharmaceutical composition comprises: 1-35 mg, 2.5-30 mg, 5-25 mg, δ-14 mg, 10-12 mg cannabidiol (CBD) per dose.

Embodiment 10. The pharmaceutical composition of any one of embodiments 1-8, wherein the pharmaceutical composition comprises about: 1 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 17.5 mg, 20 mg, 22.5 mg, 25 mg, 27.5 mg, or 30 mg cannabidiol (CBD) per dose.

Embodiment 11. The pharmaceutical composition of any one of embodiments 1-8, wherein the pharmaceutical composition comprises δ-14 mg cannabidiol (CBD).

Embodiment 12. The pharmaceutical composition of any one of embodiments 1-8, wherein the pharmaceutical composition comprises 10-12 mg cannabidiol (CBD).

Embodiment 13. The pharmaceutical composition of any one of embodiments 1-12, wherein the one or more terpenes comprise β-myrcene, β-caryophyllene, ocimene, α-pinene, α-humulene, linalool, p-cymene, camphene, cis-nerolidol, terpinolene, isopulegol, caryophyllene oxide, δ-limonene, geraniol, guaiol, α-bisabolol, 3-carene, β-pinene, γ-terpinene, or a combination thereof.

Embodiment 14. The pharmaceutical composition of any one of embodiments 1-12, wherein the one or more terpenes comprise β-myrcene, β-caryophyllene, ocimene, α-pinene, α-humulene, linalool, p-cymene, and camphene.

Embodiment 15. The pharmaceutical composition of any one of embodiments 1-12, wherein the one or more terpenes comprise β-myrcene, β-caryophyllene, ocimene, α-pinene, and α-humulene.

Embodiment 16. The pharmaceutical composition of any one of embodiments 1-12, wherein the one or more terpenes comprise β-myrcene, ocimene, cis-nerolidol, terpinolene, isopulegol, caryophyllene oxide, δ-limonene, geraniol, guaiol, and α-bisabolol.

Embodiment 17. The pharmaceutical composition of any one of embodiments 1-12, wherein the one or more terpenes comprise β-myrcene, ocimene, cis-nerolidol, terpinolene, isopulegol, caryophyllene oxide, δ-limonene, geraniol, guaiol, α-bisabolol, and 3-carene.

Embodiment 18. The pharmaceutical composition of any one of embodiments 1-12, wherein the one or more terpenes comprise β-myrcene, β-caryophyllene, ocimene, α-humulene, linalool, p-cymene, camphene, 3-carene, R-pinene, and γ-terpinene.

Embodiment 19. The pharmaceutical composition of any one of embodiments 1-12, wherein the one or more terpenes comprise β-myrcene, β-caryophyllene, ocimene, α-pinene, α-humulene, linalool, ρ-cymene, camphene, 3-carene, β-pinene, and γ-terpinene.

Embodiment 20. The pharmaceutical composition of any one of embodiments 1-19, wherein the one or more terpenes comprise β-myrcene, and wherein the pharmaceutical composition comprises 1-100 mg, 20-80 mg, 30-60 mg, 40-50 mg, 1-10 mg, 1.5-7.5 mg, or 2-5 mg of β-myrcene per dose.

Embodiment 21. The pharmaceutical composition of any one of embodiments 1-19, wherein the one or more terpenes comprise β-myrcene, and wherein the pharmaceutical composition comprises about: 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.5 mg, 5 mg, 6 mg, 7 mg, 8 mg, 9 mg, or 10 mg of β-myrcene per dose.

Embodiment 22. The pharmaceutical composition of any one of embodiments 1-19, wherein the one or more terpenes comprise β-myrcene, and wherein the pharmaceutical composition comprises about: 25 mg, 30 mg, 35 mg, 40 mg, 45 mg, 50 mg, 55 mg, or 60 mg of β-myrcene per dose.

Embodiment 23. The pharmaceutical composition of any one of embodiments 1-19, wherein the one or more terpenes comprise β-myrcene, and wherein the pharmaceutical composition comprises 1.5-7.5 mg of β-myrcene per dose.

Embodiment 24. The pharmaceutical composition of any one of embodiments 1-19, wherein the one or more terpenes comprise β-myrcene, and wherein the pharmaceutical composition comprises 30-60 mg of β-myrcene per dose.

Embodiment 25. The pharmaceutical composition of any one of embodiments 1-24, wherein the one or more terpenes comprise β-caryophyllene, and wherein the pharmaceutical composition comprises 1-20 mg, 2-10 mg, 2.5-5 mg, or 3-8 mg of β-caryophyllene per dose.

Embodiment 26. The pharmaceutical composition of any one of embodiments 1-24, wherein the one or more terpenes comprise β-caryophyllene, and wherein the pharmaceutical composition comprises about 1 mg, 1.5 mg, 2 mg, 2.25 mg, 2.5 mg, 2.75 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.25 mg, 4.5 mg, 4.75 mg, 5 mg, 5.5 mg, 6 mg, 6.5 mg, 7 mg, 7.5 mg, 7.6 mg, 8 mg, 9 mg, 10 mg, 12.5 mg, 15 mg, or 20 mg of β-caryophyllene per dose.

Embodiment 27. The pharmaceutical composition of any one of embodiments 1-24, wherein the one or more terpenes comprise β-caryophyllene, and wherein the pharmaceutical composition comprises 2.5-5 mg of β-caryophyllene per dose.

Embodiment 28. The pharmaceutical composition of any one of embodiments 1-27, wherein the one or more terpenes comprise ocimene, and wherein the pharmaceutical composition comprises 1-20 mg, 2-10 mg, 2.3-4.7 mg, or 3-8 mg of ocimene per dose.

Embodiment 29. The pharmaceutical composition of any one of embodiments 1-27, wherein the one or more terpenes comprise ocimene, and wherein the pharmaceutical composition comprises about 1 mg, 1.1 mg, 1.5 mg, 2 mg, 2.1 mg, 2.3 mg, 2.5 mg, 2.75 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.2 mg, 4.5 mg, 4.7 mg, 5 mg, 5.5 mg, 6 mg, 6.5 mg, 7 mg, 7.5 mg, 7.6 mg, 8 mg, 9 mg, 10 mg, 12.5 mg, 15 mg, or 20 mg of ocimene per dose.

Embodiment 30. The pharmaceutical composition of any one of embodiments 1-27, wherein the one or more terpenes comprise ocimene, and wherein the pharmaceutical composition comprises 2.3-4.7 mg of ocimene per dose.

Embodiment 31. The pharmaceutical composition of any one of embodiments 1-30, wherein the one or more terpenes comprise α-pinene, and wherein the pharmaceutical composition comprises 0.1-10 mg, 0.5-5 mg, or 1.1-2.1 mg of α-pinene per dose.

Embodiment 32. The pharmaceutical composition of any one of embodiments 1-30, wherein the one or more terpenes comprise α-pinene, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.75 mg, 3 mg, 3.5 mg, 4 mg, 4.5 mg, 5 mg, 7.5 mg, or 10 mg of α-pinene per dose.

Embodiment 33. The pharmaceutical composition of any one of embodiments 1-30, wherein the one or more terpenes comprise α-pinene, and wherein the pharmaceutical composition comprises 1.1-2.1 mg of α-pinene per dose.

Embodiment 34. The pharmaceutical composition of any one of embodiments 1-33, wherein the one or more terpenes comprise α-humulene, and wherein the pharmaceutical composition comprises 0.1-5 mg, 0.5-3.5 mg, or 0.8-1.6 mg of α-humulene per dose.

Embodiment 35. The pharmaceutical composition of any one of embodiments 1-33, wherein the one or more terpenes comprise α-humulene, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.5 mg, 4 mg, 4.5 mg, or 5 mg of α-humulene per dose.

Embodiment 36. The pharmaceutical composition of any one of embodiments 1-33, wherein the one or more terpenes comprise α-humulene, and wherein the pharmaceutical composition comprises 0.8-1.6 mg of α-humulene per dose.

Embodiment 37. The pharmaceutical composition of any one of embodiments 1-36, wherein the one or more terpenes comprise linalool, and wherein the pharmaceutical composition comprises 0.1-2 mg, 0.2-1.5 mg, or 0.3-0.9 mg of linalool per dose.

Embodiment 38. The pharmaceutical composition of any one of embodiments 1-36, wherein the one or more terpenes comprise linalool, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2 mg of linalool per dose.

Embodiment 39. The pharmaceutical composition of any one of embodiments 1-36, wherein the one or more terpenes comprise linalool, and wherein the pharmaceutical composition comprises 0.3-0.9 mg of linalool per dose.

Embodiment 40. The pharmaceutical composition of any one of embodiments 1-39, wherein the one or more terpenes comprise p-cymene, and wherein the pharmaceutical composition comprises 0.1-20 mg, 0.25-10 mg, 5-10 mg, or 0.5-0.9 mg of p-cymene per dose.

Embodiment 41. The pharmaceutical composition of any one of embodiments 1-39, wherein the one or more terpenes comprise p-cymene, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.5 mg, 3 mg, 4 mg, 5 mg, 5.5 mg, 6 mg, 6.5 mg, 6.75 mg, 7 mg, 7.1 mg, 7.2 mg, 7.3 mg, 7.4 mg, 7.5 mg, 8 mg, 9 mg, 10 mg, 12.5 mg, 15 mg or 20 mg of p-cymene per dose.

Embodiment 42. The pharmaceutical composition of any one of embodiments 1-39, wherein the one or more terpenes comprise p-cymene, and wherein the pharmaceutical composition comprises 0.5-0.9 mg of p-cymene per dose.

Embodiment 43. The pharmaceutical composition of any one of embodiments 1-42, wherein the one or more terpenes comprise camphene, and wherein the pharmaceutical composition comprises 0.01-2 mg, 0.02-1 mg, 0.03-0.5 mg, or 0.05 to 0.15 mg of camphene per dose.

Embodiment 44. The pharmaceutical composition of any one of embodiments 1-42, wherein the one or more terpenes comprise camphene, and wherein the pharmaceutical composition comprises about 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.3 mg, 0.4 mg, 0.5 mg, 0.6 mg, 0.7 mg, 0.8 mg, 0.9 mg, 1 mg, 1.25 mg, 1.5 mg, 1.75 mg, or 2 mg of camphene per dose.

Embodiment 45. The pharmaceutical composition of any one of embodiments 1-42, wherein the one or more terpenes comprise camphene, and wherein the pharmaceutical composition comprises 0.05-0.15 mg of camphene per dose.

Embodiment 46. The pharmaceutical composition of any one of embodiments 1-45, wherein the one or more terpenes comprise cis-nerolidol, and wherein the pharmaceutical composition comprises 0.5-20 mg, 1-10 mg, or 1.5 to 5 mg of cis-nerolidol per dose.

Embodiment 47. The pharmaceutical composition of any one of embodiments 1-45, wherein the one or more terpenes comprise cis-nerolidol, and wherein the pharmaceutical composition comprises about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.25 mg, 2.5 mg, 3 mg, 4 mg, 4.5 mg, 4.8 mg, 5 mg, 6 mg, 7 mg, 8 mg, 9 mg 10 mg, 15 mg, or 20 mg of cis-nerolidol per dose.

Embodiment 48. The pharmaceutical composition of any one of embodiments 1-45, wherein the one or more terpenes comprise cis-nerolidol, and wherein the pharmaceutical composition comprises 1.5-5 mg of cis-nerolidol per dose.

Embodiment 49. The pharmaceutical composition of any one of embodiments 1-48, wherein the one or more terpenes comprise terpinolene, and wherein the pharmaceutical composition comprises 0.5-10 mg, 1-5 mg, or 1.2 to 3 mg of terpinolene per dose.

Embodiment 50. The pharmaceutical composition of any one of embodiments 1-48, wherein the one or more terpenes comprise terpinolene, and wherein the pharmaceutical composition comprises about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.25 mg, 2.5 mg, 3 mg, 4 mg, 4.5 mg, 4.8 mg, 5 mg, 6 mg, 7 mg, 8 mg, 9 mg 10 mg, 15 mg, or 20 mg of terpinolene per dose.

Embodiment 51. The pharmaceutical composition of any one of embodiments 1-48, wherein the one or more terpenes comprise terpinolene, and wherein the pharmaceutical composition comprises 1.2-3 mg of terpinolene per dose.

Embodiment 52. The pharmaceutical composition of any one of embodiments 1-51, wherein the one or more terpenes comprise isopulegol, and wherein the pharmaceutical composition comprises 0.1-5 mg, 0.5-3.5 mg, or 0.8 to 2.3 mg of isopulegol per dose.

Embodiment 53. The pharmaceutical composition of any one of embodiments 1-51, wherein the one or more terpenes comprise isopulegol, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.3 mg, 2.5 mg, 3 mg, 3.5 mg, 4 mg, 4.5 mg, 4.8 mg, or 5 mg of isopulegol per dose.

Embodiment 54. The pharmaceutical composition of any one of embodiments 1-51, wherein the one or more terpenes comprise isopulegol, and wherein the pharmaceutical composition comprises 0.8-2.3 mg of isopulegol per dose.

Embodiment 55. The pharmaceutical composition of any one of embodiments 1-54, wherein the one or more terpenes comprise caryophyllene oxide, and wherein the pharmaceutical composition comprises 0.1-5 mg, 0.5-3.5 mg, or 0.8 to 2.2 mg of caryophyllene oxide per dose.

Embodiment 56. The pharmaceutical composition of any one of embodiments 1-54, wherein the one or more terpenes comprise caryophyllene oxide, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.2 mg, 2.5 mg, 3 mg, 3.5 mg, 4 mg, 4.5 mg, 4.8 mg, or 5 mg of caryophyllene oxide per dose.

Embodiment 57. The pharmaceutical composition of any one of embodiments 1-54, wherein the one or more terpenes comprise caryophyllene oxide, and wherein the pharmaceutical composition comprises 0.8-2.2 mg of caryophyllene oxide per dose.

Embodiment 58. The pharmaceutical composition of any one of embodiments 1-57, wherein the one or more terpenes comprise δ-limonene, and wherein the pharmaceutical composition comprises 0.1-5 mg, 0.5-3.5 mg, or 0.8 to 1.6 mg of δ-limonene oxide per dose.

Embodiment 59. The pharmaceutical composition of any one of embodiments 1-57, wherein the one or more terpenes comprise δ-limonene, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.2 mg, 2.5 mg, 3 mg, 3.5 mg, 4 mg, 4.5 mg, 4.8 mg, or 5 mg of δ-limonene per dose.

Embodiment 60. The pharmaceutical composition of any one of embodiments 1-57, wherein the one or more terpenes comprise δ-limonene, and wherein the pharmaceutical composition comprises 0.8-1.6 mg of δ-limonene per dose.

Embodiment 61. The pharmaceutical composition of any one of embodiments 1-60, wherein the one or more terpenes comprise geraniol, and wherein the pharmaceutical composition comprises 0.1-3 mg, 0.2-1.5 mg, or 0.4 to 0.9 mg of geraniol per dose.

Embodiment 62. The pharmaceutical composition of any one of embodiments 1-60, wherein the one or more terpenes comprise geraniol, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.2 mg, 2.5 mg, or 3 mg of geraniol per dose.

Embodiment 63. The pharmaceutical composition of any one of embodiments 1-60, wherein the one or more terpenes comprise geraniol, and wherein the pharmaceutical composition comprises 0.4-0.9 mg of geraniol per dose.

Embodiment 64. The pharmaceutical composition of any one of embodiments 1-63, wherein the one or more terpenes comprise guaiol, and wherein the pharmaceutical composition comprises 0.1-5 mg, 0.2-3.5 mg, or 0.4 to 3.2 mg of guaiol per dose.

Embodiment 65. The pharmaceutical composition of any one of embodiments 1-63, wherein the one or more terpenes comprise guaiol, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.2 mg, 2.4, 2.5 mg, 2.75, 3 mg, 3.2 mg, 3.5 mg, 4 mg, 4.5 mg, or 5 mg of guaiol per dose.

Embodiment 66. The pharmaceutical composition of any one of embodiments 1-63, wherein the one or more terpenes comprise guaiol, and wherein the pharmaceutical composition comprises 0.4-3.2 mg of guaiol per dose.

Embodiment 67. The pharmaceutical composition of any one of embodiments 1-66, wherein the one or more terpenes comprise α-bisobolol, and wherein the pharmaceutical composition comprises 0.1-3 mg, 0.2-1.5 mg, or 0.3 to 0.7 mg of α-bisobolol per dose.

Embodiment 68. The pharmaceutical composition of any one of embodiments 1-66, wherein the one or more terpenes comprise α-bisobolol, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.2 mg, 2.5 mg, or 3 mg of α-bisobolol per dose.

Embodiment 69. The pharmaceutical composition of any one of embodiments 1-66, wherein the one or more terpenes comprise α-bisobolol, and wherein the pharmaceutical composition comprises 0.3-0.7 mg of α-bisobolol per dose.

Embodiment 70. The pharmaceutical composition of any one of embodiments 1-69, wherein the one or more terpenes comprise 3-carene, and wherein the pharmaceutical composition comprises 0.1-3 mg, 0.2-1.5 mg, or 0.4 to 0.9 mg of 3-carene per dose.

Embodiment 71. The pharmaceutical composition of any one of embodiments 1-69, wherein the one or more terpenes comprise 3-carene, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.2 mg, 2.5 mg, or 3 mg of 3-carene per dose.

Embodiment 72. The pharmaceutical composition of any one of embodiments 1-69, wherein the one or more terpenes comprise 3-carene, and wherein the pharmaceutical composition comprises 0.4-0.9 mg of 3-carene per dose.

Embodiment 73. The pharmaceutical composition of any one of embodiments 1-72, wherein the one or more terpenes comprise β-pinene, and wherein the pharmaceutical composition comprises 0.1-5 mg, 0.3-3 mg, or 0.6 to 2.0 mg of β-pinene per dose.

Embodiment 74. The pharmaceutical composition of any one of embodiments 1-72, wherein the one or more terpenes comprise β-pinene, and wherein the pharmaceutical composition comprises about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.2 mg, 2.4, 2.5 mg, 2.75, 3 mg, 3.2 mg, 3.5 mg, 4 mg, 4.5 mg, or 5 mg of β-pinene per dose.

Embodiment 75. The pharmaceutical composition of any one of embodiments 1-72, wherein the one or more terpenes comprise β-pinene, and wherein the pharmaceutical composition comprises 0.6-2.0 mg of β-pinene per dose.

Embodiment 76. The pharmaceutical composition of any one of embodiments 1-75, wherein the one or more terpenes comprise γ-terpinene, and wherein the pharmaceutical composition comprises 0.05-1.6 mg, 0.1-0.8 mg, or 0.2 to 0.4 mg of γ-terpinene per dose.

Embodiment 77. The pharmaceutical composition of any one of embodiments 1-75, wherein the one or more terpenes comprise γ-terpinene, and wherein the pharmaceutical composition comprises about 0.05 mg, 0.06 mg, 0.07 mg, 0.08 mg, 0.09 mg, 0.1 mg, 0.11 mg, 0.12 mg, 0.13 mg, 0.14 mg, 0.15 mg, 0.16 mg, 0.17 mg, 0.18 mg, 0.19 mg, 0.20 mg, 0.21 mg, 0.22 mg, 0.23 mg, 0.24 mg, 0.25 mg, 0.26 mg, 0.27 mg, 0.28 mg, 0.29 mg, 0.3 mg, 0.31 mg, 0.32 mg, 0.33 mg, 0.34 mg, 0.35 mg, 0.36 mg, 0.37 mg, 0.38 mg, 0.39 mg, 0.4 mg, 0.45 mg, 0.5 mg, 0.55 mg, 0.6 mg, 0.75 mg, 1.0 mg, 1.1 mg, 1.2 mg, 1.3 mg, 1.4 mg, 1.5 mg, or 1.6 mg of γ-terpinene per dose.

Embodiment 78. The pharmaceutical composition of any one of embodiments 1-75, wherein the one or more terpenes comprise γ-terpinene, and wherein the pharmaceutical composition comprises 0.2-0.4 mg of γ-terpinene per dose.

Embodiment 79. The pharmaceutical composition of any one of embodiments 1-78, wherein the one or more terpenes comprise β-myrcene, β-caryophyllene, ocimene, α-pinene, α-humulene, or a combination thereof, and wherein the pharmaceutical composition comprises about 30-60 mg of the β-mycene, about 2.5-5 mg of the β-caryophyllene, about 2.3-4.7 mg of the ocimene, about 1.1-2.1 mg of the α-pinene, about 0.8-1.6 mg of the α-humulene, or a combination thereof per dose.

Embodiment 80. The pharmaceutical composition of any one of embodiments 1-78, wherein the one or more terpenes comprise β-myrcene, β-caryophyllene, ocimene, α-pinene, and α-humulene; and wherein the pharmaceutical composition comprises about 30-60 mg of the β-mycene, about 2.5-5 mg of the β-caryophyllene, about 2.3-4.7 mg of the ocimene, about 1.1-2.1 mg of the α-pinene, and about 0.8-1.6 mg of the α-humulene per dose.

Embodiment 81. The pharmaceutical composition of any one of embodiments 1-80, wherein the pharmaceutical composition is formulated as a liquid, a pill, a gel capsule, a vaporizable liquid, a vaporizable solid, a transdermal ointment or salve, or a transdermal patch.

Embodiment 82. The pharmaceutical composition of any one of embodiments 1-80, wherein the pharmaceutical composition is formulated as a liquid.

Embodiment 83. The pharmaceutical composition of embodiment 82, wherein the liquid comprises citric acid, blue agave, glycerine, one or more lorann oils, food coloring, or a combination thereof.

Embodiment 84. The pharmaceutical composition of embodiment 82, wherein the liquid comprises: (a) about 1% to 7% w/w citric acid; (b) about 40% to 49% w/w blue agave; (c) about 40% to 49% w/w glycerin; (d) about 0.1% to 1.5% w/w lorann oils; (e) about 0.01 to 0.4% food coloring; (f) or a combination thereof.

Embodiment 85. The pharmaceutical composition of embodiment 82, wherein the liquid comprises: (a) about 1% to 7% w/w citric acid; (b) about 40% to 49% w/w blue agave; (c) about 40% to 49% w/w glycerin; (d) about 0.1% to 1.5% w/w lorann oils; and (e) about 0.01 to 0.4% food coloring.

Embodiment 86. The pharmaceutical composition of embodiment 82, wherein the liquid comprises: (a) about 3-5% w/w citric acid; (b) about 45-49% w/w blue agave; (c) about 45-49% w/w glycerin; (d) about 0.7-0.9% w/w lorann oils; and (e) about 0.1-0.3% food coloring.

Embodiment 87. The pharmaceutical composition of any one of embodiments 1-86, for use in the treatment of opioid addiction.

Embodiment 88. The pharmaceutical composition of any one of embodiments 1-86, for use in the treatment of pain.

Embodiment 89. The pharmaceutical composition of any one of embodiments 1-86, for use in the treatment of chemotherapy-induced nausea and vomiting.

Embodiment 90. A method of treating opioid addition, the method comprising administering an effective amount of a pharmaceutical composition comprising one or more cannabinoids to a subject in need thereof.

Embodiment 91. The method of embodiment 90, wherein the pharmaceutical composition is the pharmaceutical composition of any one of embodiments 1-86.

Embodiment 92. The method of embodiment 90 or 91, wherein the pharmaceutical composition is administered every 1, 2, 3, 4, 5, 6, 7, 8, 9, 10, 11, 12, 13, 14, 15, 16, 17, 18, 19, 20, 21, 22, 23, or 24 hours.

Embodiment 93. The method of embodiment 90 or 91, wherein the pharmaceutical composition is administered every 6, 8 or 12 hours.

Embodiment 94. The method of any one of embodiment 90-93, wherein the subjects opioid use decreases by at least 50% within 5 weeks of beginning treatment as determined by morphine equivalency of opioids used.

Example 1 —Exemplary Formulation Preparation

This example details the production of an exemplary cannabinoid formulation that can be used in the methods disclosed herein.

Briefly, 400 g citric acid, 5000 g blue agave, and 5000 g glycerin are mixed and heated to 150° C. Separately, 300 g ethanol is heated and mixed with THC oil and CBD isolate until complete dissolution. Then, both mixtures are combined, flavoring (80 g Lorann Oils, e.g., watermellon, cherry) and coloring (20 g food coloring) are added, and the resulting mixture is sonicated until ingredients are thoroughly incorporated.

The final product is aliquoted to bottles, each containing about 5.5 oz. A single dose is about 12 mL.

The final product can contain, for example, about 15-20 mg THC and about 10-12 mg CBD per dose. The final product can also contain terpenes; for example, 30-60 mg 0-myrcene (e.g., about 45 mg), 2.5-5 mg β-caryophyllene (e.g., about 3.7 mg), 2.3-4.7 mg ocimene (e.g., about 3.5), 1.1-2.1 mg α-pinene (e.g., about 1.6), 0.8-1.6 mg α-humulene (e.g, about 1.2 mg), or a combination thereof. Table 2 contains an exemplary recipe.

TABLE 2

Exemplary formulation recipe
Batch Size: 10,000 g
16 g formulation = 12 mL volume = 1 dose

| Component | Amount Added | Percent by Weight | mg/g | mg/dose |
|---|---|---|---|---|
| Carriers/Excipients | | | | |
| Citric Acid | 393.27 g | 3.933% | | |
| Blue Agave | 4729.13 g | 47.291% | | |
| Glycerine | 4729.13 g | 47.291% | | |
| Flavor: Lorann Oils | 78.65 g | 0.787% | | |
| Food Coloring | 19.66 g | 0.197% | | |
| Cannabinoids | | | | |
| THC | 9.38 g | 0.094% | 0.9375 mg/g | 15 mg/dose |
| CBD | 6.25 g | 0.063% | 0.625 mg/g | 10 mg/dose |
| Terpenes | | | | |
| β-myrcene | 28.13 g | 0.281% | 2.8125 mg/g | 45 mg/dose |
| β-Caryophyllene | 2.31 g | 0.023% | 0.23125 mg/g | 3.7 mg/dose |
| Ocimene | 2.19 g | 0.022% | 0.21875 mg/g | 3.5 mg/dose |
| α-pinene | 1.00 g | 0.010% | 0.1 mg/g | 1.6 mg/dose |
| α-humulene | 0.75 g | 0.008% | 0.075 mg/g | 1.2 mg/dose |

Example 2

Over the last 150 years the perceived and reported medicinal effects or benefits associated with the consumption of products derived from the *cannabis* plant have fluctuated as much as the most volatile stock market period in history. Periodically, the benefits have been held out to be Olympian in nature, virtually a cure all for all conditions while at other times use of the *cannabis* has been associated with "reefer madness"; including suicidal ideation, sexual promiscuity, and in general uncontrolled impulses. The truth, as usual lies somewhere in between. Add in a dose of world politics and posturing; difficulty in conducting trials; an error in taxonomy; the radically different effect ascribed to the two main components of the plant, Delta-9 tetrahydrocannabinol (THC) and Cannabidiol (CBD) consumed in a variety of ways; a less than clear understanding of the metabolism of the compounds and the endocannabinoid system; and the inability to link a specific plant profile to a specific outcome have all made it even more difficult in separating the flower from the trim, as it pertains to *cannabis Sativa* and its medicinal effects.

For the purposes of this forum the historic marketing of *cannabis* and its by-products will be left to an excellent reference as will references to reefer madness type publications. Regarding world and US politics, our present-day situation, for the most part, is governed nationally by the Nixon administration ignoring the recommendations of the National Commission of Marihuana and Drug Abuse (The Schafer Commission) and its appendix both published in 1972, which overall called for decriminalization of personal possession and use of *cannabis*. Even this report was not without controversy. To paraphrase a report issued by the Committee on Public Health of the New York Academy of Medicine, it recommended that a government agency investigate the feasibility of control and distribution of marihuana through a government agency, while a New England Journal editorial suggested that legalization offered the best promise for effective control of marihuana. Nahas and Greenwood published a detailed rebuttal to the Shafer Commission report and ultimately the administration ignored the Commission's recommendations. Currently 28 states, the District of Columbia and a few of the over 500 recognized Indian tribal nations have passed laws regulating the sale of *cannabis* either for medical or both medical and recreational use and the laws enacted by each of these government(s) or their legislation are at odds with federal statute. The recent rescinding of the Cole memorandum by Attorney General Sessions has added fuel to the fires of confusion which unfortunately will not be solved here but all should be left with the warning of "buyer beware".

Now onto the science. Like staging systems for each cancer, we can all argue the merits of the specifics defining each stage, but none would argue against the need for uniformity. For without it, discussion of results and therefore evaluation of new treatments would be rendered impossible. *Cannabis*, was taxonomically divided into three species in the 1970s; *C. indica, C. sativa*, and *C. ruderalis*. Adding to the confusion, yet ultimately clarifying was the work of McPartland wherein he proved on a genetic basis that these were all the same species, just different subspecies. More importantly he found that *C. sativa* originated in India and should have been classified as *C. indica; C. indica* originated in Afghanistan and should have been identified as *C. afghanica*; and *C. ruderalis* is most properly classified as *C. sativa*. Until this nomenclature is standardized comparing research results will be near impossible.

Since Mechooulam's group identified and synthesized both cannabidiol (CBD) and delta-9 tetrahydrocannabinol (THC) the psychoactive component in the *cannabis* plant there have been over 60 phytocannabinoids the identified in addition to approximately 400 other components of the *cannabis* plant including a large number of terpenes that account for the associated aroma and may contribute to the entourage effects of *cannabis*. Research efforts have logically been based upon our understanding of the cannabinoid receptors so far identified throughout the body, but particularly in the brain and metabolism via the cytochrome P450 pathways. Left to further study is the molecular basis for the therapeutic effect of associated with cannabidiol (CBD) as it has little affinity for the CB1 and CB2 receptors. Of most importance at this time has been the identification of CBD acting as a negative allosteric modulator thereby changing the shape of the CB1 receptor and thus dampens the psychoactive effect associated with the consumption of THC when taken in combination with CBD.

Much of our collective knowledge regarding the clinical effects of cannibinoids arises from case reports and observational and retrospective studies. There are few prospective randomized trials reported. Many that pertain to clinical oncology involve the use of dronabinol for the relief of chemotherapy-induced nausea and vomiting and pain. May and Giode have thoroughly reviewed much of this literature. Dronabinol has offered little relief over available anti-emetic regimens. Additional prospective studies have been conducted using oromucosal nabiximols (THC:CBD of 1:1) for intractable spasticity in patients with multiple sclerosis (MS) and those results led to the FDA ultimately granting GW Pharmaceuticals (London UK, Carlsbad CA) approval for this indication. Trials using the same product, designed to determine its effectiveness in cancer-associated pain, was not found to be better than placebo. Maccarrone et al have reviewed results of trials involving oromucosal nabiximols. Russo similarly has provided an excellent review on the matter of trial design and other controversies associated with research in this area, including issues involving clinical trial approval and design. Highlighted by Russo are the difficulties encountered when attempting to undertake research involving *cannabis*, in particular the need to either use *cannabis* provided exclusively by the University of Mississippi or apply to cultivate and supply your study drug.

In Nevada, efforts to conduct federally-approved research undertaken with the intent of filing a new drug application a has been thwarted as the Institutional Review Board (IRB) at the University Medical Center (UMC) requires DEA assurance before considering any protocol containing *cannabis* in a treatment arm, yet to obtain federal permission one needs IRB approval of the study of concern.

Addressing the opiate crisis in this country has led to a number of studies being conducted using *cannabis*-based therapy as an alternative means of managing chronic and cancer-related pain. Despite Nabiximols not appearing to be statistically superior when compared to placebo in controlling pain in cancer patients, there are other randomized placebo controlled trials demonstrating the efficacy of using *cannabis* for pain control. There is also significant evidence that a *cannabis*-opioid interaction exists that results in improved pain control. All of the studies to date have either used pain scales or patient interview results to determine the success or failure of the *cannabis* intervention. Given the increasing availability of legal *cannabis*, there will be fewer opportunities to study a *cannabis* naïve population use as it is clear from the work of Bachhuber et al. that patients are self-treating with *cannabis* in order to reduce if not eliminate their dependence on narcotics. This is reflected by the 24% reduction in opiate-related deaths in states with legalized medical marijuana programs as compared to those without.

We, a group of physicians in Nevada, are licensed to cultivate, produce and sell *cannabis*-related products and have recently undertaken a randomized, placebo controlled study using a guava-based syrup with a THC:CBD ratio of about 2:1 and a placebo containing only the flavored guava-based syrup. As a proof of concept 25 patients with a history of at least 3 years of chronic opiate use were enrolled in a single arm study with the endpoint being a 30% reduction of opiate intake determined by weekly pill count.

The population of subjects in this study included 14 women and 11 men. The average age of participants was about 55 years old, with the youngest being 21 and the oldest being 77. The median age was about 58 years old. According to their medical histories, 4 participants had a history of gynecologic or breast cancer; 11 participants have had spine surgery; 5 participants have had a hysterectomy; 4 participants reported hypertension; 2 participants reported coronary artery disease, 2 participants had diabetes; 11 participants used tobacco; 6 participants used alcohol; and 3 participants reported drug abuse.

A morphine equivalent calculation was adopted for this study to account for the varying opiates used by the study participants. Hydrocodone alone was used by 9 participants; hydrocodone plus morphine sulfate was used by 1 participant; hydromorphone alone was used by 2 participants; hydromorphone plus methadone was used by 1 participant; oxycodone alone was used by 6 participants; oxycodone plus methadone was used by 1 participant; oxycodone plus morphine sulfate was used by 2 participants; and Percocet was used by 3 participants.

Figure 1B:
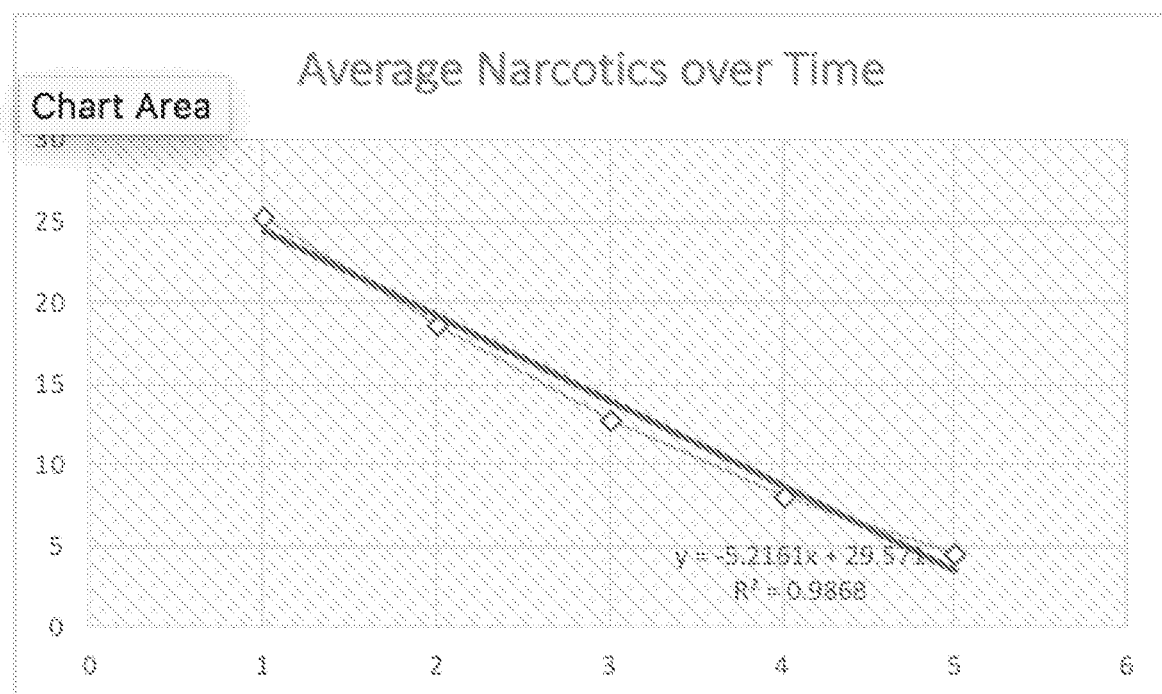
Figures 2A, 2B:
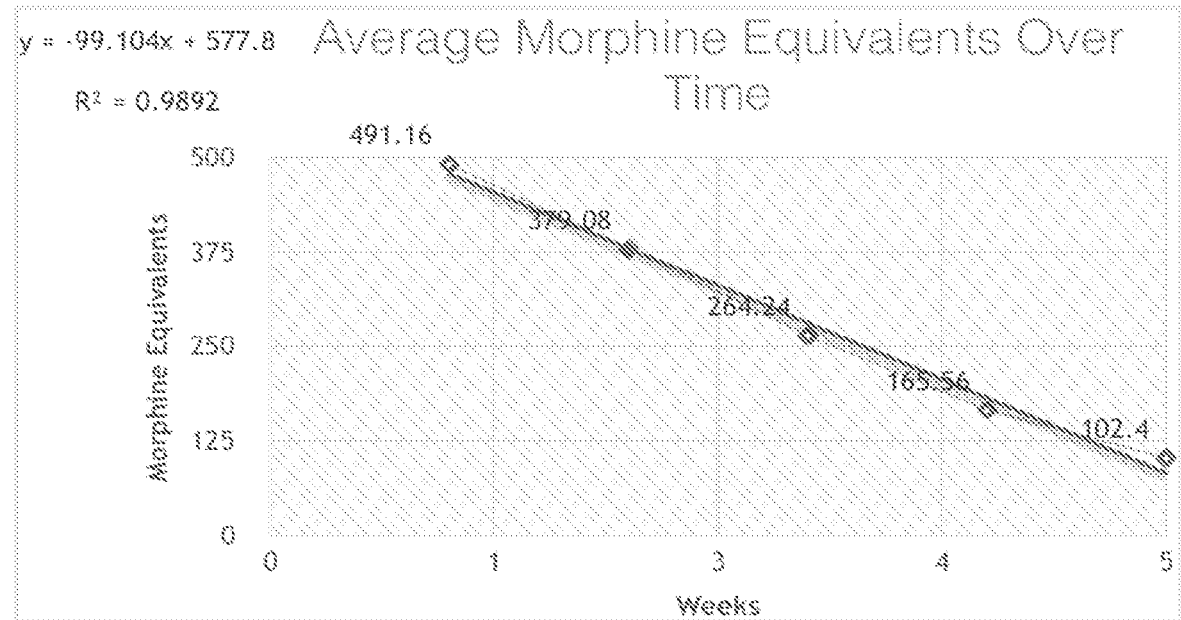
FIGS. 2a & b illustrates weekly pill counts in morphine equivalents in tabular form (FIG. 2a) and graph form with regression analysis (FIG. 2b).

23 of the 25 patients reduced their opiate intake by greater than 50%. The average weekly pill count is charted in FIG. 1*a* with regression analysis shown in FIG. 1*b*. The average weekly pill counts after conversion to morphine equivalents is shown in FIG. 2*a* with regression analysis shown in FIG. 2*b*. These results provide an objective basis to evaluate the potential of *cannabis* to replace to reduce the opiate consumption across the US. We have also opened a trial to evaluate the effectiveness of this syrup with some slight modifications in the terpene profile, in controlling chemotherapy-induced nausea and vomiting (CINV).

References, each of which is incorporated by reference in its entirety:

Mills M. Moguls and Mexicans: The American history of *cannabis* legalization. The New Econom Mar. 27, 2015. theneweconomy.com.

National Commission on Marihuana and Drug Abuse: Marihuana: A Signal of Misunderstanding: First Report of the National Commission on Marihuana and Drug Abuse. Washington D.C., Govt. Print. Off. 1972.

National Commission on Marihuana and Drug Abuse: Marihuana: A Signal of Misunderstanding: Technical papers, Appendix, vols. 1 and 2. Washington D.C., Govt. Print. Off. 1972.

Wechsler H. Marihuana, alcohol and public policy. New Eng. J. Med. 287:516-17, 1972

Nahas G G, Greenwood A. The first report of the National Commission on marihuana (1972): signal of misunderstanding or exercise in ambiguity. Bull N Y Acad Med. 1974 Jan; 50(1):55-75.

McPartland J M. "*Cannabis sativa* and *Cannabis* indica versus "*Sativa*" and "Indica"." In *Cannabis sativa* L.—Botany and Biotechnology, edited by Chandra S, Lata H and ElSohly M A, pp 101-121. Switzerland: Springer International Publishing, 2017.

Micholaum R and Shvo Y. Hasish. I. The structure of cannabidiol.Tetrahedron. 1963 Dec; 19(12): 2073-8

Gaoni Y and Micholaum R. Isolation, Structure, and Partial Synthesis of an Active Constituent of Hashish.J. Am. Chem. Soc., 1964, 86 (8), pp 1646-1647.

Howlett A C1, Barth F, Bonner T I, Cabral G, Casellas P, Devane W A, Felder C C, Herkenham M, Mackie K, Martin B R, Mechoulam R, Pertwee R G. International Union of Pharmacology. XXVII. Classification of cannabinoid receptors. Pharmacol Rev. 2002 Jun; 54(2):161-202.

Breivogel C S1, Childers S R. The functional neuroanatomy of brain cannabinoid receptors. Neurobiol Dis. 1998 December; 5(6 Pt B):417-31

Russo E B. Taming THC; potential *cannabis* synergy and phytocannabinoid=terpenoid entourage effects. Br J Pharmacol. 2011 August; 163 (7):1344-1364.

Lapairie R B, Bagher, A M, Kelly, M E Denovan-Wright, E M. Cannabidiol is a negative allosteric modulator of the cannabinoid CB1 receptor. Br J Pharmacol. 2015 October; 172(20): 4790-4805.

May M B and Glode A E. Dronabinol for chemotherapy-induced nausea and vomiting unresponsive to anti-emetics. Cancer Manag Res. 2016; 8: 49-55.

Maccarrone M, Maldanado R, Casas M, Henze T, and Centonze D. Cannabinoids therapeutic use: what is our current understanding following the introduction of THC, THC:CBD oromucosal spray and others? Expert Review of Clinical Pharmacology. 2017; 10: 443-55.

Russo E B. Current Therapeutic Cannabis Controversies and Clinical Trial Design Issues. Front Pharmacol. 2016; 7: 309-339.

Lichtman A H, Lux E A, McQuade R, Rossetti s, Sanchez R, Sun W. Wright S, Kornyeyeva E, Fallon M T. Results of a double-blind, randomized, placebo-controlled study of Nabiximols oromucosal spray as an adjunctive therapy in advanced cancer patients with chronic uncontrolled pain.nJ Pain Symptom Manage. 2018; 55: 179-188.

Abrams D I, Couey P, Shader S B, Kelly M E, Benowitz N I. Cannabinoid-opioid Interaction in chronic pain. Clin. Pharmacol. Ther. 2011; 90; 844-851.

Miller G. Pot and Pain. Hints are emerging that cannabis could be an alternative to opioid painkillers. Science. 2016: 354; 566-568

Whiting P F, Wolff R E, Deshpande S, Di Niso M, Duffy S, Hemandez A V, Keurentjes J C, Lang S, Misso K, Rider s, Schmidkofer S, Westwood M, Kleijnen J. Cannabinoids for Medical Use: A systematic review and meta-analysis. JAMA. 2015; 313; 2456-2473.

Bachhuber M A, Saloner B, Cunningham C O, Barry C L. Medicinal cannabis laws and opioid analgesic overdose mortality in the United States, 1999-2010. JAMA Intern. Med. 2014 174; 1668-1673.

EXAMPLE 3 a Phase III Double-Blind, Randomized, Placebo Controlled (with Crossover) Trial of Medical Marijuana Versus Placebo for the Reduction of Opiate Consumption in Patients with Chronic Pain

| Arm I: Placebo | Arm II: THC/CBD (strain specific) |
|---|---|
| If no improvement ↓ Double the Dose ↓ If no improvement, Cross-over to Arm II | If no improvement ↓ Double the Dose ↓ If no improvement, Cross-over to Arm I |

Objectives

Primary Objective: To determine if the number of patients consuming opiates for chronic pain treate d with medicinal cannabis (15-20 mg THC/10-12 mg CBD-strain specific) in an agave-based syrup that are able to eliminate their opiate consumption is not reduced by 300% when compared to an identical agave-based syrup without cannabis.

Secondary Objective: To determine the incidence of adverse events associated with both regimens. Common Terminology for Adverse Events (CTAE ver. 4) will be used to scale adverse events.

Background and Rationale

The available literature on the medicinal effects of cannabis is sparse and for the most part lacks critical aspects of study design including prospective design and randomization. The reasons for this are varied, but primarily they are based on the fact that cannabis remains a schedule 1 drug and its production and ingestion are against federal law. Most studies have evaluated synthetics, nabilone or dronabinol, with few evaluating THC derived from plant. Internationally, over 30 countries have approved its use either recreationally or medicinally. Some countries such as Paraguay and Chile have legalized cultivation and production of cannabis products. Over half of the states and the District of Columbia have legalized the use of cannabis medicinally and some have approved its use recreationally. In the last few years, research into the underlying neurophysiology associated with cannabis has led to an increased understanding of the different active components and the biochemical pathways responsible for the associated therapeutic effects. The constituents seemingly responsible for the claimed medicinal effects of the cannabis plant can include delta-9-tetrahydrocannabinol (THC) and cannabidiol (CBD).

The purported beneficial medicinal effects associated with cannabis ingestion are quite diverse. Of the claims made, the most studied are in patients with multiple sclerosis, where a beneficial effect on muscle spasticity and pain are well-documented, but not necessarily as consistently as one might like. Cannabis can also be effective in treating seizures, anorexia, chronic pain, and nausea and vomiting that is associated with chemotherapy. Cannabidiols may also have a therapeutic effect of inflammation, diabetes, cancer, and neurodegenerative diseases. On the other hand THC ingestion has been associated with less than desirable side effects such as agitation; panic disorder; depression and even psychosis.

Perhaps as importantly, the political landscape is changing as rapidly as is the understanding of the underlying mechanisms of action associated with cannabis. Indications of this are the increasing number of states that have legalized the medicinal use of cannabis and the call by some states, such as Nevada, to undertake research to evaluate the clinical benefits associated with the use of cannabis.

The opiate epidemic continues to be associated with over 100 deaths daily in the United States. Couple this with the estimated total annual cost of pain-related health of approximately $600 billion and perhaps this figure is even higher for the nations in European Union (EU) and therein is born the impetus to evaluate virtually any therapy that may thwart these related problems. This estimate includes the actual costs related to the medical care as well as the economic losses which contribute to approximately one-half of these costs. Economic losses include claimed disability, loss of productivity and lost wages. Medical care including physician time, hospitalization, surgical procedures, diagnostic testing and prescription drugs all contribute to the costs associated with the treatment of pain, as well the costs associated with the adverse effects associated with their utilization. Unfortunately, one of the adverse effects associated with prescription painkillers is death. Overdose deaths secondary to prescription opioids were five times higher in 2016 than 2000 and sales of these prescription drugs have quadrupled. That being said, the number of deaths dues to prescription opioids has remained relative stable at approximately 14,000 to 16,000 deaths per year. Much of the increase in mortality related to opioid consumption is due the rapid rise in those associated with the use of synthetic opioids. Of importance is the fact that in state with either medical marijuana or both medical and retail marijuana programs in place there was a 24.8% lower mean annual opiod overdose mortality rate (95% CI, −37.5% to −9.5%: P=0.003) compared with states without medical marijuana laws.

Addressing the opiate crisis in this country has led to a number of studies being conducted using *cannabis*-based therapy as an alternative means of managing chronic and cancer-related pain. Despite Nabiximols not appearing to be superior when compared to placebo in controlling pain in cancer patients, *cannabis* may have efficacy for pain control. A *cannabis*-opioid interaction may also result in improved pain control.

*Cannabis* contains at least 63 cannabinoids but two are best understood studied. The first, delta-9 tetrahydrocannabinol (THC), is thought to be responsible for the psychoactive effects that are widely associated with *cannabis*. The other main active component, cannabidiol (CBD), has no known psychoactive effect associated with its consumption but is thought to possibly provide anti-neoplastic, analgesic and antineuroleptic effects. Even though both cannabinoids are present in every plant, the interactions with the cerebral endocannabinoid receptor system are quite different. CBD binds as an antagonist to the cannabinoid receptor CB1 but the bond between THC and the same receptor is at least 100 times stronger. CBD also antagonizes the action on the cannabinoid G protein-coupled receptor GPR55, which is thought to be responsible the different neuromodulatory actions as the CB1 receptor. Claims of the subjective effects associated with *cannabis* ingestion include improvement in mood; relaxation; and increased sensitivity. On the other hand THC ingestion has been associated with less than desirable adverse effects such as agitation; panic disorder; depression and even psychosis.

Cannabinoids can have an effect on serotonergic systems, including increasing cerebral production of 5-hydroxytryptamine (5-HT), serotonin while decreasing its uptake at the synapse level. THC may also have dopaminergic antagonistic actions which may contribute to its beneficial profile regarding pain control.

Other phytocannabinoids such as cannabichromene (CBC), cannabigerol (CBG) as well as a number of terpenoids may contribute its analgesic effect. CBD, cannabinol (CBN),CBC and CBG can have anti-inflammatory and analgesic effects over and beyond that associated with THC. B-caryophyllene may be a selective CB2 agonist and other terpenes such as linalool and α-Pinene may have analgesic and anti-inflamatory effects respectively. Myrcene on the other hand may have analgesic effects mediated through an opioid-like action. This may lead to another avenue as to how *cannabis* and it component parts may prevent opiate withdrawal and allow for the use of lesser amounts of opioids while preventing the development of tolerance. Used in combination with opioid pain medications, *cannabis* can lower opioid side effects, cravings, and withdrawal severity, as well as enhance the analgesic effects of opioids, thereby allowing for lower doses and less risk of overdose.

All of the studies to date have either used pain scales or patient interview results to determine the success or failure of the *cannabis* intervention.

We have recently undertaken a phase II feasibility trial using a guava-based syrup with a THC:CBD ratio of 1.5:1 to 2:1 derived from a specific *cannabis* plant with a unique profile of other phytocannabinoids such as CBC, CBN, and CBG as well as a number of terpenoids which likely contribute to its analgesic effect. Each dose of syrup contained 15-20 mg of THC and 10-12 mg of CBD as well as a unique profile associated with one specifically bred *cannabis* plant. A proof of concept trial of 25 patients with a history of at least 3 years of chronic opiate use were enrolled in a single arm study with the target for success being a 30% reduction of opiate intake determined by weekly pill count.

Using a morphine equivalent conversion of all of the various opiates consumed by the study population it was determined that there was a reduction in opiate consumption of approximately 75% and 8/25 patients (40%) were able to replace their prescription opiates with the agave-based THC-CBD syrup. This provides an objective basis to evaluate the potential of *cannabis* to reduce if not eliminate a significant amount of the opiate consumption across the US. As explained above the actions of THC, CBD, and associated terpenes are potentially complementary and the recent feasibility trial provides substantial evidence of potential benefit of using them together for patients with chronic pain.

That being said another important consideration in administering *cannabis* to patients is the potential drug-to-drug interactions and adverse effects associated with its use and potential withdrawal. THC is metabolized via the Cytochrome P450 pathway and more specifically it is thought that the CYP2C9 enzyme is responsible for the first pass metabolism of THC. The CYP3A4 enzyme may also have a role in its metabolism. Coumadin effect on prothrombin time (PT) is significantly enhanced by the use of THC/CBD. Theophylline levels may be adversely affected. There have been reported adverse events when *cannabis* is used with sildenafil, including a myocardial infarction. Since THC is a CNS depressant its use with alcohol, barbiturates, antihistamines, narcotics, and BZD, theoretically could amplify the effects of both drugs. It should be noted there has not been any clinical trial documenting these interactions. Similarly, adverse events need to be carefully documented. In this context cannabinoid receptors are not located in the brainstem as are opioid receptors and therefore do not have the associated risk of respiratory depression and death. Adverse effects including, but not limited to tachycardia and hypotension, anxiety and nervousness, hyperactivity, muscle relaxation, decreased bowel motility, and bronchodilatation have been documented.

The addictive potential of cannabinoids is thought to be lower than opiates and its derivatives as well as other frequently abused substances. Interestingly, as cannabinoids are stored in adipose, excretion takes place over a relatively long-time thus preventing precipitous declines in the plasma concentration and potentially explaining the lack of acute withdrawal symptoms associated with the cessation of *cannabis* use. Nevertheless, there have been documented symptoms associated with withdrawal including, but not limited to, nausea and vomiting, increased activity, nervousness, irritability, insomnia, and vasomotor symptoms.

This overall safety profile of the cannabinoids made them an excellent candidate to be studied as an opiate substitute. A recently completed pilot study demonstrated in 25 patients, a 75% reduction in opiate ingestion over a 4-5 week period, with 8/25 patients completely discontinuing their opiate use. The same formulation used in that study will be studied here.

Inclusion of Women and Minorities

No potential subject will be excluded from participating in this or any study solely on the basis of ethnic origin or socioeconomic status. Every attempt will be made to enter all eligible patients into this protocol and therefore address the study objectives in a patient population representative of the entire population currently consuming opiates for over three years.

PATIENT ELIGIBILITY AND EXCLUSIONS

Eligible Patients Criteria
1) Patients currently consuming opiates chronically for a minimum of 3 years.
2) Patients who can read understand and write English or have a translator available to do so.
3) Patients who are able to complete the assessments.
4) Patients who are able to comply with treatment regimen and be seen on a weekly basis at the study site to have their medications counted and an assessment completed.
5) Patient must hold a valid Nevada Medical Marijuana Card or be qualified by reciprocity as defined by Nevada Statute.

Ineligible Patients Criteria
1) Patients who, in the opinion of their physician, have any condition that may contradict potential withdrawal symptoms associated potential reduction of opiate ingestion.
2) Patients known to have had a hypersensitivity reaction to any of the drugs to be received as part of this trial.
3) Patients currently taking warfarin or similar products.
4) Patients taking Tadalafil (Cialis T M), Sildenafil (Viagra), or Theophylline.
5) Pregnant patients or patients on oral contraceptives who are not willing to use another form of back up birth control in addition to the pill.
6) Patients who have used *cannabis* within the last one month.

Study Modalities

Tetrahydrocannabinol: Cannabidiol (THC:CBD) agave based syrup (20 mg THC/10 mg CBD) vs control agave-based syrup.

Each bottle will contain either 150-200 mg:100-120 mg (THC:CBD) in an agave based syrup with reconstituted terpene profile or the agave-based syrup alone. The emulsification process renders the material virtually odorless allowing for the patient to be blinded.

Storage and Stability: store vials at 2-8° C. (36-46° F.).
Preparation: emulsified solution.
How Supplied: in glass jars with increments and doses labeled on each bottle.
Administration: both are to be administered on a q6 to q8 hour basis (e.g., every 6 to 8 hours) by either direct administration or the syrup is to be mixed with 7-up with care being taken to chew the ice. If ineffective, the patient will double the dose. If there is no improvement then the patient will be crossed-over.
Adverse Events: THC ingestion has been associated with adverse effects such as agitation; panic disorder; depression and even psychosis and all adverse events will be chronicled based on version 4.

*Cannabis*

DESCRIPTION

Tetrahydrocannabinol: Cannabidiol (THC:CBD) agave based syrup (15-20 mg THC/10-12 mg CBD) with reconstituted terpene profile versus control agave-based syrup.

*Cannabis* is intended for use as a psychoactive drug or as a medicine. The main psychoactive part of *cannabis* is tetrahydrocannabinol (THC); it is one of at least 421 known compounds in the plant, including at least 61 other cannabinoids, such as cannabidiol (CBD), cannabinol (CBN), and tetrahydrocannabivarin (THCV).

Researchers have subsequently confirmed that THC exerts its most prominent effects via its actions on two types of cannabinoid receptors, the CB1 receptor and the CB2 receptor, both of which are G-protein coupled receptors. The CB1 receptor is found primarily in the brain as well as in some peripheral tissues, and the CB2 receptor is found primarily in peripheral tissues, but is also expressed in neuroglial cells THC appears to alter mood and cognition through its agonist actions on the CB1 receptors, which inhibit a secondary messenger system (adenylate cyclase) in a dose dependent manner. These actions can be blocked by the selective CB1receptor antagonist SR141716A (rimonabant), which has been shown in clinical trials to be an effective treatment for smoking cessation, weight loss, and as a means of controlling or reducing metabolic syndrome risk factors. However, due to the dysphoric effect of CB1 antagonists, this drug is often discontinued due to these side effects. Via CB1 activation, THC indirectly increases dopamine release and produces psychotropic effects. Cannabidiol also acts as an allosteric modulator of the mu and delta opioid receptors. THC also potentiates the effects of the glycine receptors. The role of these interactions in the "marijuana high" remains elusive.

The high lipid-solubility of cannabinoids results in their persisting in the body for long periods of time. Even after a single administration of THC, detectable levels of THC can be found in the body for weeks or longer (depending on the amount administered and the sensitivity of the assessment method). A number of investigators have suggested that this is an important factor in marijuana's effects, perhaps because cannabinoids may accumulate in the body, particularly in the lipid membranes of neurons.

In comparison to smoking and inhalation, after oral ingestion, systemic absorption is relatively slow resulting in maximum $\Delta 9$-THC plasma concentration within 1-2 hours which could be delayed by few hours in certain cases. In some subjects, more than one plasma peak was observed. Extensive liver metabolism probably reduces the oral bioavailability of $\Delta 9$-THC by 4-12%. After oral administration, maximum $\Delta 9$-THC plasma concentration was 4.4-11 ng/mL for 20 mg and 2.7-6.3 ng/mL for 15 mg. Much higher concentration of 11-OH THC was produced after ingestion than inhalation. Following assimilation via the blood, $\Delta 9$-THC rapidly penetrates in to fat tissues and highly vascularized tissues including brain and muscle resulting in rapid decrease in plasma concentration. This tissue distribution is followed by slow redistribution of it from the deep fat deposits back into the blood stream. It should be noted that the residual $\Delta 9$-THC levels are maintained in the body for a long time following abuse. The half-life of it for an infrequent user is 1.3 days and for frequent users 5-13 days. After smoking a cigarette containing 16-34 mg of $\Delta 9$-THC, THC—COOH is detectable in plasma for 2-7 days. A clinical study carried out among 52 volunteers showed that THC—COOH was detectable in serum from 3.5 to 74.3 hours. Initial concentration was between 14-49 ng/mL. This was considerably less than the THC—COOH detection time of 25 days in a single chronic user.

$\Delta 9$-THC is metabolized in the liver by microsomal hydroxylation and oxidation catalyzed by enzymes of cytochrome P450 (CYP) complex. The average plasma clearance rates have been reported to be 11.8±3 L/hour for women and 14.9±3.7 L/hour for men. Others have determined approximately 36 L/hour for naïve *cannabis* users and 60 L/hour for regular *cannabis* users. More than 65% of *cannabis* is excreted in the feces and approximately 20% is excreted in urine. Most of the *cannabis* (80-90%) is excreted within 5 days as hydroxylated and carboxylated metabolites. There are eighteen acidic metabolites of *cannabis* identified in urine and most of these metabolites form a conjugate with glucuronic acid, which increases its water solubility. Among the major metabolites (A9-THC,11-OH-THC, and THC-COOH), THCCOOH is the primary glucuronide conjugate in urine, while 11-OH-THC is the predominant form in feces. Since A9-THC is extremely soluble in lipids, it results in tubular re-absorption, leading to low renal excretion of unchanged drug. Urinary excretion half-life of THCCOOH was observed to be approximately 30 hours after seven days and 44-60 hours after twelve days of monitoring. After smoking approximately 27 mg of A9-THC in a cigarette, 11-OH-THC peak concentration was observed in the urine within two hours in the range of 3.2-53.3 ng/mL, peaking at 77.0±329.7 ng/mL after 3 hours and THCCOOH peaking at 179.4 ng/mL±146.9 after 4 hours.

Stability and Storage

Store at room temperature in a colored bottle to avoid decomposition of the THC.

Preparation

The syrup is prepared using CO2 extracted THC which is then decarboxylated. The syrup is composed of agave syrup, glycerin, citric acid, lecithin, THC/CBD oil, coloring and flavoring. Each bottle, marked on the sides in 12 millimeter increments, will contain a total of 150-200 mg of THC and approximately 100-120 mg of CBD and will provide ten doses of medicine. The placebo will be the identical mixture without the addition of THC/CBD oil.

Administration

The patient will ingest 12 ml of either placebo or medicinal *cannabis* containing approximately 15-20 mg of THC and 10-12 mg CBD with the plant-specific terpenes reconsituted on a QID basis. The patients will be allowed to double the dose if symptoms to do not resolve.

Adverse Events

Short-term adverse effects include alterations in short-term memory, sense of time, sensory perception, attention span, problem solving, verbal fluency, reaction time, and psychomotor control. Some users report positive feelings such as mild euphoria and relaxation, while others, particularly naïve users, report anxiety, paranoia, and panic reactions. Depression and anxiety have also been reported as short-term adverse events. The short-term effects of marijuana last approximately 1-4 hours, depending on potency of the marijuana, the route of administration, and the tolerance of the user. Furthermore, there have been reports of adverse cardiac events including arrhythmias associated with a prolonged Q-T interval; hypertension and hypotension; tachycardia; and myocardial infarction. It is much more difficult to assess long-term adverse effects that may be attributable to the consumption of medicinal *cannabis*. While there is no question that marijuana causes short-term impairments in brain function, the degree to which these impairments are reversible with chronic use is less clear. Some studies have shown that brain function recovers over time, while others demonstrate persistence of subtle, but important, impairments. There is some suggestion that schizophrenia may be associated with long-term usage of *cannabis*. Lastly, there are the general concerns of smoking associated with *cannabis* use although that is not of concern as it relates to this study as the *cannabis* will be ingested and not inhaled.

Drug Interactions

A 9-THC is metabolized in the liver by microsomal hydroxylation and oxidation catalyzed by enzymes of cytochrome P450 (CYP) complex. As a result any drug that is similarly metabolized may be affected. Particular attention must be given to warfarin or similar products; tadalafil or similar products; and anti-depressants.

Treatment Plan and Entry

IRB Approval and IRB-Approved Informed Consent

Patient Entry and Registration

Treatment Plan

This is a double-blind phase III prospective randomized two-arm study which will be conducted in patients with chronic pain with a history of at least 3 years use of opiates for analgesia. Patients will be randomized using a computer based randomization program off-site and overseen by the independent observer. Patients will start the study within 2 days of filling their opiate prescription and verification through the Nevada State Prescription Monitoring Program that the patient is receiving narcotics from only a single source. The total morphine milligram equivalents (MME) used weekly by the subject will be calculated based on the CDC conversion table. Subjects will be given a diary to record time and amount of study medication used on a daily basis in addition to recording any adverse events. Diaries will be collected weekly. Patients will be given physician phone number in order to report any adverse event.

Week 1. Patients are to use syrup (A or B) as directed on a q 6 hour basis and use their opiates only for breakthrough pain. The patient will be seen at the end of each week and a pill count will be done to determine the quantity of opiate (MME) consumed by the subject and recorded.

Weeks 2-7. At the end of week 2 if there has been no improvement as determined by at least a 20% reduction in total MME used compared to the baseline, the patient will crossed over and continued on the new syrup for a minimum of two additional weeks and if no reduction of at least 20% in total MME study treatment will be discontinued. If the patient's consumption of MME decreases by more than 20% within the first two weeks after initial drug assignment or after two weeks after being crossed-over, the patient will continue on the study drug for at least 4 additional weeks. The patient will be followed through the end of the study with collection of all study data.

Treatment Modifications

Before cross-over has taken place if there is no improvement from the patient's baseline assessment the dose of either the placebo or THC/CBD will be doubled. Within two weeks after cross-over should the total MME used not decrease by at least 20% the subject will be recorded as a failure of study treatment.

Study Parameters

Observations and Tests

The following observations and tests are to be performed and recorded on the

| PARAMETER | Baseline or Day 1 | Day 2 | Day 3 | Day 4 | Day 5 | Day 6 | Day 7 | Days 8, 15, 22, 29, 36, 43 |
|---|---|---|---|---|---|---|---|---|
| History & Physical | 1 | | | | | | | |
| Medication diary | X** | X | X | X | X | X | X | 2 |
| Pill count and MME calculation | X** | X | X | X | X | X | X | 2 |
| Gen Chemistry Panel: Electrolytes: CBC c diff: PT/INR | 1 | | | | | | | 3 |
| Toxicity Diary & Assessment | X | X | X | X | X | X | X | 2 |

1. The baseline History and Physical done will be used if performed within 30 days of entry.
2. Patients will return the Medication Diary weekly. The toxicity assessment will be completed daily by the patient and tabulated weekly unless grade 3 or greater toxicity occurs.
3. Additional blood work will be ordered by the treating physician as needed.

Evaluation Criteria

The MME calculated at study entry, weekly and then at completion will be used to determine treatment course as well as the success or failure of the study drug.

The patients will complete a daily medication and toxicity diary and will be assessed weekly.

Parameters of Response

Amount of opiate consumed by pill count and MME will be recorded in the medication diary and by the physicians conducting the study. The primary outcome is the complete elimination of opiate used to control the subject's symptoms.

Secondary outcome is the percentage reduction of opiate used to control the subject's symptoms as measured by pill count and MME.

Adverse events will be documented by the study subjects and verified by the physicians conducting the study Duration of Study The duration of the study will be 4 weeks at a minimum unless subject withdraws voluntarily or is caused to withdraw secondary to an adverse event deemed severe enough either by the patient or treating physician to warrant the subject's withdrawal from the protocol prescribed treatment plan.

Study Monitoring and Reporting Procedures

Adverse Event Reporting For A Commercial Agent

Definition of Adverse Events (AE)

An adverse event (AE) is any unfavorable and unintended sign (including an abnormal laboratory finding), symptom, or disease that occurs in a patient administered a medical treatment, whether the event is considered related or unrelated to the medical treatment. The descriptions and grading scales found in the revised NCI Common Terminology Criteria for Adverse Events (CTCAE) version 4.0 will be utilized for AE reporting. All appropriate treatment areas should have access to a copy of the CTCAE version 4.0.

Definition of Serious Adverse Event (SAE)

A Serious Adverse Event (SAE) is defined as any untoward medical occurrence that at any dose:
1. Results in death
2. Is life threatening (i.e., the subject was, in the opinion of the investigator, at immediate risk of death from the event as it occurred); it does not refer to an event which hypothetically might have caused death if it were more severe
3. Requires or prolongs inpatient hospitalization
4. Results in persistent or significant disability/incapacity (i.e., the event causes a substantial disruption of a person's ability to conduct normal life functions)
5. Results in a congenital anomaly/birth defect
6. Requires intervention to prevent permanent impairment or damage
7. Is an important and significant medical event that may not be immediately life threatening or resulting in death or hospitalization but, based upon appropriate medical judgment, may jeopardize the patient/subject or may require intervention to prevent one of the other outcomes listed above.

Reporting Expedited Adverse Events

An AE report may need to reach multiple destinations. All expedited AEs will be reported to the IRB or the supervising body overseeing this study. Reporting will be modeled after AdEERS submissions. All adverse reactions will be immediately directed to the Study Chair for further action.

Note: All deaths on study require both routine and expedited reporting regardless of causality. Attribution to treatment or other cause must be provided.

Expedited AE reporting timelines defined:

"24 hours; 3 calendar days"—The investigator must initially report the AE within 24 hours of learning of the event followed by a complete report within 3 calendar days of the initial 24-hour report.

"7 calendar days"—A complete report on the AE must be submitted within 7 calendar days of the investigator learning of the event. Any medical event equivalent to CTCAE grade 3, 4, or 5 that hospitalization (or prolongation of existing hospitalization) must be reported regardless of attribution and designation as expected or unexpected with the exception of any events identified as protocol-specific expedited adverse event reporting exclusions.

AEs should be reported by the investigator.

Pilot Trials Utilizing a Commercial Agent: AdEERS Expedited Reporting Requirements for Adverse Events That Occur Within 30 Days of the Last Dose of Any Study Agent Reporting Requirements for Adverse Events that occur within 30 Days of the Last Dose of the Commercial Agent on Pilot Trials—GUIDELINES TO BE FOLLOWED regarding reporting of AEs to the Principal Investigator and the IRB

|  | Grade 1 Unexpected and Expected | Grade 2 Unexpected | Grade 2 Expected | Grade 3 Unexpected With Hospitalization Without Hospitalization | Grade 3 Expected With Hospitalization Without Hospitalization | | Grades 4 & 5[2] Unexpected | Grades 4 & 5[2] Expected |
|---|---|---|---|---|---|---|---|---|
| Unrelated Unlikely | Not Required | Not Required | Not Required | 7 Calendar Days | Not Required | 7 Calendar Days | Not Required | 7 Calendar Days | 7 Calendar Days |
| Possible Probable Definite | Not Required | 7 Calendar Days | Not Required | 7 Calendar Days | 7 Calendar Days | 7 Calendar Days | Not Required | 24-Hrs; 3 Calendar Days | 7 Calendar Days |

[1] Adverse events with attribution of possible, probable, or definite that occur greater than 30 days after the last dose of treatment with a commercial agent require reporting as follows: AdEERS 24-hour notification followed by complete report within 3 calendar days for: Grade 4 and Grade 5 unexpected events AdEERS 7 calendar day report:. Grade 3 unexpected events with hospitalization or prolongation of hospitalization and Grade 5 expected events
[2] Although an AdEERS 24-hour notification is not required for death clearly related to progressive disease, a full report is required as outlined in the table. Please see exceptions below under the section entitled, "Additional Instructions or Exceptions to AdEERS Expedited Reporting Requirements for Pilot Trials Utilizing a Commercial Agent." March 2005

Any event that results in persistent or significant disabilities/incapacities, congenital anomalies, or birth defects must be reported to the Study Chair if the event occurs following treatment with a commercial agent.

Additional Instructions or Exceptions to AdEERS Expedited Reporting Requirements for Pilot Trials Utilizing a Commercial Agent will be applied to this study:

In rare cases, pregnancy might occur in clinical trials. Any pregnancy occurring in association with the use of the study medication and the pregnancy outcome must be reported within five days of first awareness.

The event of overdose of aprepitant is considered an SAE by the manufacturer. In the event that there is an overdose of aprepitant, report the overdose and any clinical consequences that occur in association with an overdose.

Procedures for Expedited Adverse Event Reporting:

Expedited Reports: Expedited reports are to be submitted to the study Chair and the IRB using reports similar to the AdEERS.

Data Management Forms

The following forms must be completed for all patients and must be received in the study office in accordance with the schedule below.

Primary Endpoints:
Primary efficacy endpoint: cessation of opioids for at least 7 days as determined by the treating physician.
Primary safety endpoint: Common Terminology Criteria for Adverse Events (CTCAE)—version 4.0.
Secondary Endpoints:
Weekly morphine equivalency does (MED).
Pain Numeric Score (PNS)
Enrollment and Target Sample Size The target enrollment for this study is 64 subjects. The estimated accrual rate is 6 subjects per month. At this rate the enrollment period for this study is expected to require at most 1 year.

In order to account for the loss in power due to non-compliance, the target sample size will be increased by 2 subjects for each subject who withdraws from the study prior to completing at least 4 weeks of treatment or cannot be adequately evaluated for opioid usage.

Study Hypotheses
Null Hypotheses for Primary Efficacy Endpoint:
Ho: THC/CBD does not increase the probability of stopping opioids within 5 weeks of starting THC/CBD compared to placebo.

| Form± | Due within Weeks | Event | Copies* | Comments |
|---|---|---|---|---|
| History and Physical[1] | 4 | Registration | 1 | |
| Consent | 4 | Registratiom | 1 | Submit to study co-ordinator |
| Patient Symptom Diary | 4 | weekly | 1 | Submit to study co-ordinator |
| Pill count and MME log | 2 | weekly | 1 | Submit to study co-ordinator |
| T (Toxicity) Form | 2 | weekly | 1 | Submit to study co-ordinator |
| AE report | | See protocol | 1 | Submit to study co-ordinator |
| Form R | 2 | Registration | 1 | Submit to study co-ordinator |

[1]The History and Physical It is not necessary to repeat for this study.

Statistical Considerations
Study Design

This is a randomized, 2-arm, double-blind, placebo-controlled phase III clinical trial evaluating THC/CBD as an aid to stopping opioid patients who are taking opioids due to chronic pain.

The overall objective of this study is to evaluate the probability of stopping opioid use within 5 weeks for patients diagnosed with chronic pain and treated with THC/CBD compared to those receiving placebo.

Treatment allocation and Emergency Unblinding

The subjects enrolled into this study will receive either daily THC/CBD or a placebo. The study treatments will be sequentially allocated from predetermined lists consisting of randomly permuted study treatments within blocks. This allocation procedure will tend to allocate each of the study regimens to nearly an equal number of the enrollees. Other than blocking the treatments, the randomization procedure will not be otherwise constrained to provide an equal number of subjects in each treatment group. The randomized treatment for each individual will remain concealed unless there arises a need for emergency unblinding. Emergency unblinding occurs when the appropriate clinical care of the subject requires knowledge of her study treatment. The study's Principle Investigator will be responsible for reviewing and approving requests for emergency unblinding. An independent statistician will be responsible for revealing the study treatment.

Measures of Efficacy and Safety

The principal observation for evaluating the therapeutic efficacy and safety of the study regimens are:

Type I Error Allocation

The type I error for the primary efficacy hypothesis will be 0.025 for a one-tail test.

Analytic Procedures for Testing Hypothesis (HO)
Primary Analysis:

For the primary analysis subjects will be group according to their randomly assigned treatment and they will be included in the analysis, regardless of their compliance with their assigned treatment plan. Individuals who withdraw early from the study without stopping opioids will be classified in the analysis of the primary endpoint as treatment failures (i.e., not stopping opioids).

Inferences regarding the clinical significance of THC/CBD will be made based on a Fisher's exact test of the primary study hypothesis.

Secondary and Exploratory analyses:

A logistic model will be used to assess whether the subject's initial morphine equivalency dose (MED), age or other clinical or demographic factors are treatment effect modifiers.

A linear mixed model will be used to model the patients' weekly morphine equivalency dose over time for women randomized to placebo vs those randomized to THC.

Statistical Power

With 32 subjects treated on each of the study regimens, this design provides 82% chance of rejecting the primary null hypothesis for efficacy when the true probabilities of stopping opioids within 5 weeks are 5% and 35% for placebo and active, respectively.

Interim Analyses

An interim futility analysis will be performed when there are at least 16 subjects treated and evaluated in each of the randomized treatment groups. If the proportion of the subjects randomly assigned to placebo who stopped all opioid usage within 5 weeks is greater than or equal to the proportion of subjects on THC/CBD, then consideration will be given to stopping the study. Otherwise, the study will continue to accrue until the target enrollment has been attained. If the study is stopped early due to this stopping boundary, then the conclusion of the study will be that it is unlikely that THC/CBD increases the probability of stopping opioid use in patients with chronic pelvic pain If the true probability stopping opioids on THC/CBD is equal to placebo, then there is a 64% chance that this stopping boundary will recommend stopping the study early. On the other hand, if the true probabilities for stopping opioids are 5% and 35% on placebo and THC/CBD, respectively, then this stopping boundary decreases the statistical power of the study by less than 0.5%.

Interim and final reports will include an accounting of all subjects registered onto the study, regardless of their eligibility status or compliance to their assigned treatment.

The Data Monitoring Committee (DMC) is responsible for reviewing the results of interim analyses. The decision to terminate accrual to the study or to release study results early includes consideration of adverse events, treatment compliance, as well as results from external studies.

REFERENCES, EACH OF WHICH IS INCORPORATED BY REFERENCE IN ITS ENTIRETY

May M B and Glode A E. Dronabinol for chemotherapy-induced nausea and vomiting unresponsive to anti-emetics. Cancer Manag Res. 2016; 8: 49-55.

Maccarrone M, Maldanado R, Casas M, Henze T, and Centonze D. Cannabinoids therapeutic use: what is our current understanding following the introduction of THC, THC:CBD oromucosal spray and others? Expert Review of Clinical Pharmacology. 2017; 10: 443-55.

Russo E B. Current Therapeutic Cannabis Controversies and Clinical Trial Design Issues. Front Pharmacol. 2016; 7: 309-339.

Lichtman A H, Lux E A, McQuade R, Rossetti s, Sanchez R, Sun W. Wright S, Kornyeyeva E, Fallon M T. Results of a double-blind, randomized, placebo-controlled study of Nabiximols oromucosal spray as an adjunctive therapy in advanced cancer patients with chronic uncontrolled pain.nJ Pain Symptom Manage. 2018; 55: 179-188.

Svendsen K B, jensen T S, Bach F W. Does the cannabinoid dronabinol reduce central pain in multiple sclerosis? Randomized doubleblind placebocontrolled crossover trial. BMJmj. 2004: 329; 253.

Vermersch P. Sativex® (tetrahydrocannabinol+cannabidiol) and endocannabinoid system modulator: basic features and main clinical data. Expert Rev Neurother. 2011; 114 (Supp): 15-19.

Ware M A, Wang T, Shapiro S, Collet Jpand the COMPASS study team. Cannabis for the management of pain: Asessment of safety study (COMPASS). J Pain; 2015 Dec 16 (12): 1233-1242.

Perron Be, Bohnert K, Perone A K, Bonn-Miller M O and Ilgen M. Use of prescription pain medications among medical cannabis patients: comparisons of pain levels, functioning, and patterns of alcohol and other drug use. J Stud Alcohol Drugs. 2015; 76(3); 406-13.

Lucas P and Walsh Z. Medical cannabis access, use, and substitution for prescription opioids and other substances: A survey of authorized medical cannabis patients. Int J Drug Policy. 2017; 42:30-35.

de Vrol ies M, van Rickevorsel D C M, Vissers K C P, Wilder-Smith O H G, van Goor H, Pain and Nociception Neuroscience Research Group. Clin Gastroenterol Hepatol. 2017; 15(7): 1079-1086.

Boehnke K F, Litinas E and Clauw D J. Medical cannabis use is associated with decreased opiate medication use in a retrospective cross-sectional survey of patients with chronic pain. J Pain. 2016; 17 (6): 739-44.

Mills M. Moguls and Mexicans: The American history of cannabis legalization. The New Econom Mar. 27, 2015. theneweconomy.com.

Micholaum R and Shvo Y. Hasish. I. The structure of cannabidiol.Tetrahedron. 1963 Dec; 19(12): 2073-8.

Gaoni Y and Micholaum R. Isolation, Structure, and Partial Synthesis of an Active Constituent of Hashish.J. Am. Chem. Soc., 1964, 86 (8), pp 1646-1647.

Howlett AC1, Barth F, Bonner T I, Cabral G, Casellas P, Devane W A, Felder C C, Herkenham M, Mackie K, Martin B R, Mechoulam R, Pertwee R G. International Union of Pharmacology. XXVII. Classification of cannabinoid receptors. Pharmacol Rev. 2002 Jun; 54(2):161-202.

Breivogel CS1, Childers S R. The functional neuroanatomy of brain cannabinoid receptors. Neurobiol Dis. 1998 December; 5(6 Pt B):417-31.

Whiting P F, Wolff R E, Deshpande S, Di Niso M, Duffy S, Hemandez A V, Keurentjes J C, Lang S, Misso K, Rider s, Schmidkofer S, Westwood M, Kleijnen J. Cannabinoids for Medical Use: A systematic review and meta-analysis. JAMA. 2015; 313; 2456-2473.

Abrams D I, Couey P, Shader S B, Kelly M E, Benowitz N I. Cannabinoid-opioid Interaction in chronic pain. Clin. Pharmacol. Ther. 2011; 90; 844-851.

Miller G. Pot and Pain. Hints are emerging that cannabis could be an alternative to opioid painkillers. Science. 2016: 354; 566-568.

Gaskin D J. Richard P. Institute of Medicine Committee on Advancing Pain Research, Care, and Education. Relieving Pain in America: A Blueprint for Transforming Prevention, Care, Education and Research.Washington, DC: The National Academies Press; 2011. Appendix C: The economic costs of pain in the United States; pp. 301-37.

Gaskin D J. Richard P. The Economic Costs of Pain in the United States. Journal of Pain. 2012; 13(8):715-24.

Whiting P F, Wolff R F, Deshpande S, Di Nisio M, Duffy S, Hemandez A V, Keurenjtes J C, Lang S, Misso K, Ryder S, Schmidkofer S, Westwood M, and Kleijnen J. Cannabinoids for medical use: A systematic review and meta-analysis. JAMA. 2015; 313(24):2456-2473.

Rudd R A1, Aleshire N, Zibbell J E, Gladden R M. Increases in Drug and Opioid Overdose Deaths—United States, 2000-2014.MMWR Morb Mortal Wkly Rep. 2016 Jan. 1; 64(50-51):1378-82.

Bachhuber M A, Saloner B, Cunningham C O, Barry C L. Medicinal cannabis laws and opioid analgesic overdose mortality in the United States, 1999-2010. JAMA Intern. Med. 2014 174; 1668-1673.

Mechoulam R. Plant cannabinoids: a neglected pharmacological treasure trive. Br J Pahrmacol. 2005: 146:913-15.

Appendino G, Chianese G, Taglialatela-Scafati O. Cannabinoids: occurrence and medicinal chemistry. Curr Med Chem. 2011; 18:1085-1099.

Mackie K. Cannabinoid receptors as therapeutic targets. Ann Rev Pharmacol Toxicol. 2006; 46:101-22.

Price M R, Baille G L, Thomas A, Stevenson L A, Easson M, Goodwin R, McLean A, McIntosh L, Goodwin G, Walker G, Westwood P, Marrs J, Thomson F, Cowley P, Christopoulos A, Pertwee R G, and Ross R A. Allosteric modulation of the cannabinoid CB1 receptor. Mol Pharmacol. 2005; 68: 1484-1495.

Gorzalka B B, Hill M N and Hillard C J. Regulation of endocannabinoid signaling by stress: implications for stress-related affective disorders. Neurisci Biobehav Rev. 2008; 32: 1152-1160.

Izzo A A, Borrelli F, Capasso R, et al. Non-psychotropic plant cannabinoids: new therapeutic opportunities from an ancient herb. Trends Pharmacol Sci. 2009; 30:515-527.

Maione S, Costa B, Di Marzo V. Endocannabinoids: a unique opportunity to develop multitarget analgesics. Pain. 2013; 154:S87-S93.

Costa B, Trovato A E, Comelli F, et al. The non-psychoactive cannabis constituent cannabidiol is an orally effective therapeutic agent in rat chronic inflammatory and neuropathic pain. Eur J Pharmacol. 2007; 556:75-83.

Evans F. Cannabinoids:the separation of central from peripheral effects on a structural basis. Planta Med. 1991; 57:S60-S67.

Qin N, Neeper M P, Liu Y, et al. TRPV2 is activated by cannabidiol and mediates CGRP release in cultured rat dorsal root ganglion neurons. J Neurosci. 2008; 28:6231-6238

Wirth P W, Watson E S, ElSohly M, et al. Anti-inflammatory properties of cannabichromene. Life Sci. 1980; 26:1991-1995.

Izzo A A, Capasso R, Aviello G, et al. Inhibitory effect of cannabichromene, a major non-psychotropic cannabinoid extracted from Cannabis sativa, on inflammation-induced hypermotility in mice. Br J Pharmacol. 2012; 166:1444-1460.

Maldonado R, Banos J E, Cabanero D. The endocannabinoid system and neuropathic pain. Pain. 2016; 157:S23-S32

La Porta C, Bura S A, Llorente-Onaindia J, et al. Role of the endocannabinoid system in the emotional manifestations of osteoarthritis pain. Pain. 2015; 156:2001-2012.

Paula-Freire L I G, Andersen M L, Molska G R, and Kohn D O. Evaluation of the Antinociceptive Activity of Ocimum gratissimumL. (Lamiaceae) Essential Oil and its isolated Active Principles in Mice. Phytother Res. 2013; 27:1220-1224.

Lemberger L, Silberstein S D, Axelrod J and Kopin I J. Marihuana: Studies on the disposition and metabolism of delta-9-tetrahydrocannabinol in man. Science. 2014; 170: 1320-22

Yamamoto I, Watanabe K Narimatsu S, and Yoshimura H. Recent advances in the metabolism of cannabinoids. Int J Biochem Cell Biol. 1995; 27: 741-746.

Bellnier T, Brown G W, Ortega T R. Preliminary evaluation of the efficacy, safety, and costs associated with the treatment of chronic pain with medical cannabis. Ment Health Clin [Internet]. 2018; 8(3):110-5.

Rong C, Carmona N E, Lee Y L, Ragguett R M, Pan Z, Rosenblat J D, Subramaniapillai M, Shekotikhina M, Almatham F, Alageel A, Mansur R, Ho R C, McIntyre R S. Drug-drug interactions as a result of co-administering Δ9-THC and CBD with other psychotropic agents. Expert Opin Drug Saf. 2018 January; 17(1):51-54.

Nicholson A N, Turner C, Stone B M, and Robson P J. Effect of delta-9 tetrahydrocannabinol and cannabidiol on nocturnal sleep and early morning behavior in young adults. J Clin Psychopharmacol. 2004; 24: 305-323.

Russo R B. Current therapeutic cannabis controversies and clinical trial design issues. (Review) Frontiers in Pharmacology. 2016; 7: 1-30.

Jones R T, Benowitz N, and Bachman J. Clinical studies of cannabis tolerance and dependence. Ann NY Acad Sci. 1976; 282: 221-239.

Nutt D, King L A, Saulsbury W, and Blakemore C. Development of a rational scale to assess the harm of drugs of potential misuse. Lancet 2007; 369: 1047-1053.

Adams I B, Martin B R. Cannabis: pharmacology and toxicology in animals and humans. Addiction. 1996; 91; 1585-614.

Grotenhermen F, Russo E. eds.: Cannabis and Cannabinoids: Pharmacology, Toxicology and Therapeutic Potential. Binghampton, N Y: The Haeworth Press, 2002.

Sutton I R, Daeninck P: Cannabinoids in the management of intractable chemotherapy-induced nausea and vomiting and cancer-related pain. J Support Oncol. 2006; 4 (10): 531-5.

Guzman M. Cannabinoids: potential anticancer agents. Nat Rev Cancer. 2003; 3(10):745-55.

Sink K, Segovia K, Sink J, et al. Potential anxiogenic effects of cannabinoid CB1 receptor anagonists/inverse agonists in rats: Comparisons between AM4113, AM251, and the benzodiazepine inverse agonist FG-7142. Eur Neuropsychopharm. 2010; 20:112-122.

Christensen R, Kristensen P K, Bartels E M et al. Efficacy and safety of the weight-loss drug rimonabant: a meta-analysis of randomized trials. Lancet. 2007; 370: 1706-13.

Hudson B D, Hebert T E, M Kelly M E. Ligand and Heterodimer-Directed Signaling of the CB1 Cannabinoid Receptor. Molecular Pharmacology 2010; 77: 1-9.

McHugh D, Hu S S J, Rimmerman N et al. N-arachidonoyl glycine, an abundant endogenous lipid, potently drives directed cellular migration trough GPR18, the putative abnormal cannabidiol receptor. Bmc Neuroscience 2010; 11:11-44.

Huestis M A. Pharmacokinetics and metabolism of the plant cannabinoids, delta9-tetrahydrocannabinol, cannabidiol and cannabinol. Handb Exp Pharmacol 2005: 657-90.

Hollister L E, Gillespie H K, Ohlsson A et al. Do plasma concentrations of delta 9-tetrahydrocannabinol reflect the degree of intoxication? J Clin Pharmacol 198; 21: 171-1775.

Lemberger L, Axelrod J, Kopin I J. Metabolism and disposition of delta-9-tetrahydrocannabinol in man. Pharmacol Rev 1971; 23: 371-80.

Law B, Mason P A, Moffat A C et al. Forensic aspects of the metabolism and excretion of cannabinoids following oral ingestion of cannabis resin. J Pharm Pharmacol. 1984; 36: 289-94.

Karschner E L, Schwilke E W lowe R H et al. Implications of plasma delta-9-tetrahydrocannabinol, 11-hydroxy-THC and 11-nor-9-carboxy-THC concentrations in chronic cannabis smokers. J Anal Toxicol. 2009; 33: 469-77.

Owen S M, McBAy A J, Reisner H M, et al. 1251 radioimmunoassay of delta-9-tetrahydrocannabinol in blood and plasma with a solid-phase second-antibody separation method. Clin Chem. 1981; 27: 619-24.

Chiarotti M, Costamagna L. Analysis of 11-nor-9-carboxy-delta (9)-tetrahydrocannabinol in biological samples by gas chromatography tandem mass spectrometry (GC/MS-MS). Forensic Scilnt. 2000; 114:1-6.

Kogan N M, Mechoulam R. Cannabinoids in health and disease. Dialogues Clin Neurosci. 2007; 9: 413-30.

Haggerty G C, Deskin R, Kurtz P J et al. The pharmacological activity of the fatty acid conjugate 11 palmitoyxy-delta 9-tetrahydrocannabinol. Toxicol Appl Pharmacol. 1986; 84: 599-606.

Smith-Kielland A, Skuterud B, Morland J. Urinary excretion of 11-nor-9-carboxy-delta 9-tetrahydrocannabinol and cannabinoids in frequent and infrequent drug users. J Anal Toxicol. 1999; 23: 323-332.

Huestis M A, Henningfield J E, Cone E J. Blood cannabinoids. I. Absorption of THC and formation of 11-OH-THC and THCCOOH during and after smoking marijuana. J Anal Toxicol. 1992; 16: 276-82.

Reiter A, Hake J, Meissner C et al. Time of drug elimination in chronic drug abusers. Case study of 52 patients in a "low-step" detoxification ward. Forensic SciInt. 2001; 119: 248-253.

Lowe R H, Abraham T T, Darwin W D et al. Extended urinary Delta9-tetrahydrocannabinol excretion in chronic *cannabis* users precludes use as a biomarker of new drug exposure. Drug Alcohol Depend. 2009; 105:24-32.

Goulle J P, Saussereau E, Lacroix C. Delta-9-tetrahydrocannabinol pharmacokinetics. Ann Pharm Fr. 2008; 66:232-244.

Halldin M M, Andersson L K, widman M et al. Further urinary metabolites of deltal-tetrahydrocannabinol in man. Arzneimittelforschung 1982; 32: 1135-1138.

Huestis M A, Cone E J. Urinary excretion half-life of 11-nor-9-carboxy-delta-9-tetrahydrocannabinol in humans. Ther Drug Monit. 1998; 20: 570-576.

Kelly P, Jones R T. Metabolism of tetrahydrocannabinol in frequent and infrequent marijuana users. J Anal Toxicol. 1992; 16: 228-235.

Johanson E K, Hollister L E, Halldin M M. Urinary elimination half-life of delta-1-tetrahydrocannabinol-7-oic acid in heavy marijuana users after smoking. NIDA Res Monogr. 1989; 95: 457-458.

Manno J E, Manno B R, Kemp P M et al. Temporal indications of marijuana use can be estimated from plasma and urine concentrations of delta-9-tetrahydrocannabinol, 11-hydroxy-delta9-tetrahydrocannabinol, and 11-nor-delta9-tetrahydrocannabinol-9-carboxylic acid. J Anal Toxicol. 2001; 25: 538-549.

Iverson L., *Cannabis* and the brain. Brain. 2003; 126: 1252-70.

Hall W. and Degenhardt L. Adverse health effects of non-medical *cannabis* use. Lancet. 2009; 374: 1383-91.

Solowij N, Stephens R S, Roffman R A et al. Cognitive functioning of long-term heavy *cannabis* users seeking treatment. JAM. 2002; 287: 1123-31. Erratum in JAMA 2002; 287: 1651.

National Governors Association Policy Academy Drug Abuse Prevention. "State of Nevada Plan to Reduce Prescription Drug Abuse". Nevada 2017. (pp 3-56)

Centers for Disease Control and Prevention, National Center for Injury and Prevention Control, Division of Unintentional Injury Prevention. Atlanta, Georgia. U.S. Department of Health and Human Services. "Calculating Total Daily Doses of Opioids for Safer Dosage". www.cdc.gov/drugoverdose/prescribing/guideline.html. Atlanta, Georgia 2017. (pp1-2)

National Cancer Institute: Common Terminology Criteria for adverse Events (CTCAE), Version 4.0 Bethesda, Md. U.S. Department of Health and Human Services, National Institutes of Health, 2010.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating opioid addiction, the method comprising orally administering to a subject in need thereof an effective amount of a liquid pharmaceutical composition in unit dose form to treat the opioid addiction comprising tetrahydrocannabinol (THC) and cannabidiol (CBD) and a terpene, wherein the liquid pharmaceutical composition comprises 15-20 mg of the THC per dose, and 10-12 mg of the CBD per dose and wherein the terpene is selected from the group consisting of β-myrcene, β-caryophyllene, ocimene, α-pinene, and α-humulene, wherein the subject's opioid use decreases by greater than or equal to 50% within 5 weeks of beginning treatment as determined by morphine equivalency of opioids used.

2. The method of claim 1, wherein the liquid pharmaceutical composition is administered every 1, 2, 3, 4, 5, 6, 7, 8, 9, 10, 11, 12, 13, 14, 15, 16, 17, 18, 19, 20, 21, 22, 23, or 24 hours.

3. The method of claim 1, wherein the liquid pharmaceutical composition is administered every 6, 8, or 12 hours.

4. The method of claim 1, wherein the liquid pharmaceutical composition further comprises a citric acid, a blue agave, a glycerine, a food coloring, or any combination thereof.

5. The method of claim 1, wherein the method further comprises treating a pain.

* * * * *